United States Patent
Rosen et al.

(10) Patent No.: US 9,974,635 B2
(45) Date of Patent: May 22, 2018

(54) INTRA-VAGINAL DEVICES AND METHODS FOR TREATING FECAL INCONTINENCE

(71) Applicant: Pelvalon, Inc., Sunnyvale, CA (US)

(72) Inventors: Miles Harris Rosen, Palo Alto, CA (US); Steven Lawrence Herbowy, Palo Alto, CA (US); Jared Goor, Sunnyvale, CA (US); Narvel M. Brooks, III, Palo Alto, CA (US)

(73) Assignee: Pelvalon, Inc., Sunnyvale, CA (US)

( * ) Notice: Subject to any disclaimer, the term of this patent is extended or adjusted under 35 U.S.C. 154(b) by 708 days.

(21) Appl. No.: 14/181,576

(22) Filed: Feb. 14, 2014

(65) Prior Publication Data

US 2014/0275744 A1    Sep. 18, 2014

Related U.S. Application Data

(60) Provisional application No. 61/764,960, filed on Feb. 14, 2013.

(51) Int. Cl.
*A61F 2/00*    (2006.01)

(52) U.S. Cl.
CPC ............ *A61F 2/0031* (2013.01); *A61F 2/005* (2013.01); *A61F 2/0027* (2013.01); *A61F 2250/0007* (2013.01)

(58) Field of Classification Search
CPC ........................................ A61F 2/0004–2/0054
USPC .......................... 600/29–31, 37; 128/834–841
See application file for complete search history.

(56) References Cited

U.S. PATENT DOCUMENTS

| | | |
|---|---|---|
| 186,469 A | 1/1877 | Fowler |
| 1,282,881 A | 10/1918 | Landis |
| 2,475,071 A | 7/1949 | Thomas |
| 2,638,093 A | 12/1952 | George |
| 3,554,184 A | 1/1971 | Habib |
| 3,646,929 A | 3/1972 | Bonnar |
| 3,675,656 A | 7/1972 | Hakim |
| 3,705,575 A | 12/1972 | Edwards |
| 3,709,215 A | 1/1973 | Richmond |
| 3,797,478 A | 3/1974 | Walsh et al. |
| 3,831,583 A | 8/1974 | Edmunds, Jr. et al. |
| 3,841,304 A | 10/1974 | Jones |
| 3,866,611 A | 2/1975 | Baumrucker |
| 3,882,852 A | 5/1975 | Sinnreich |
| 3,903,894 A | 9/1975 | Rosen et al. |
| 4,019,499 A | 4/1977 | Fitzgerald |
| 4,031,886 A | 6/1977 | Morhenn |
| 4,307,716 A | 12/1981 | Davis |
| 4,428,365 A | 1/1984 | Hakky |
| 4,587,954 A | 5/1986 | Haber |

(Continued)

FOREIGN PATENT DOCUMENTS

| | | |
|---|---|---|
| DE | 2438691 | 8/1974 |
| EP | 0068318 | 1/1983 |

(Continued)

OTHER PUBLICATIONS

International Search Report and Written Opinion, PCT/US2014/016609, dated May 1, 2014, 16 pages.

(Continued)

*Primary Examiner* — Catherine B Kuhlman
(74) *Attorney, Agent, or Firm* — Fish & Richardson P.C.

(57) ABSTRACT

Disclosed herein are devices and methods for intra-vaginal bowel control.

98 Claims, 55 Drawing Sheets

(56) References Cited

U.S. PATENT DOCUMENTS

| | | |
|---|---|---|
| 4,669,478 A | 6/1987 | Robertson |
| 4,686,985 A | 8/1987 | Lottick |
| 4,786,276 A | 11/1988 | Haber |
| 4,823,814 A | 4/1989 | Drogendjik et al. |
| 4,846,818 A | 7/1989 | Keldahl et al. |
| 4,854,990 A | 8/1989 | David |
| 4,946,449 A | 8/1990 | Davis, Jr. |
| 4,981,470 A | 1/1991 | Bombeck, IV |
| 5,007,894 A | 4/1991 | Enhoming |
| 5,041,077 A | 8/1991 | Kulick |
| 5,147,301 A | 9/1992 | Ruvio |
| 5,224,494 A | 7/1993 | Enhoming |
| 5,306,226 A | 4/1994 | Salama |
| 5,370,690 A | 12/1994 | Barrett |
| 5,474,518 A | 12/1995 | Velazquez |
| 5,520,606 A | 5/1996 | Schoolman et al. |
| 5,545,176 A | 8/1996 | Murtfeldt |
| 5,593,443 A | 1/1997 | Carter et al. |
| 5,603,685 A | 2/1997 | Tutrone, Jr. |
| 5,611,768 A | 3/1997 | Tutrone, Jr. |
| 5,702,421 A | 12/1997 | Schneidt et al. |
| 5,733,230 A | 3/1998 | Sawchuck et al. |
| 5,782,745 A | 7/1998 | Benderev |
| 5,884,629 A | 3/1999 | O'Brien |
| 6,013,023 A | 1/2000 | Klingenstein |
| 6,030,338 A | 2/2000 | Benderev |
| 6,048,306 A | 4/2000 | Spielberg |
| 6,090,038 A | 7/2000 | Zunker et al. |
| 6,090,098 A | 7/2000 | Zunker et al. |
| 6,096,057 A | 8/2000 | Klingenstein |
| 6,110,099 A | 8/2000 | Benderev |
| 6,135,945 A | 10/2000 | Sultan |
| 6,142,928 A | 11/2000 | Zunker et al. |
| 6,216,698 B1 | 4/2001 | Regula |
| 6,319,191 B1 | 11/2001 | Sayet et al. |
| 6,418,930 B1 | 7/2002 | Fowler |
| 6,428,467 B1 | 8/2002 | Benderev |
| 6,470,890 B1 | 10/2002 | Diokno et al. |
| 6,482,145 B1 | 11/2002 | Forsell |
| 6,503,190 B1 | 1/2003 | Ulmsten et al. |
| 6,558,370 B2 | 5/2003 | Moser |
| 6,569,078 B2 | 5/2003 | Ishikawa et al. |
| 6,645,137 B2 | 11/2003 | Ulmsten et al. |
| 6,676,594 B1 | 1/2004 | Zunker et al. |
| 6,682,473 B1 | 1/2004 | Matsuura et al. |
| 6,723,040 B2 | 4/2004 | Brady |
| 6,752,754 B1 | 6/2004 | Feng et al. |
| 6,770,025 B2 | 8/2004 | Zunker |
| 6,786,861 B1 | 9/2004 | Pretorius |
| 6,808,485 B2 | 10/2004 | Zunker |
| 6,843,766 B1 | 1/2005 | Nemir et al. |
| 6,913,573 B1 | 7/2005 | Viscomi et al. |
| 6,915,165 B2 | 7/2005 | Forsell |
| 6,939,289 B2 | 9/2005 | Zunker et al. |
| 6,976,950 B2 | 12/2005 | Connors et al. |
| 7,074,178 B2 | 7/2006 | Connors et al. |
| 7,083,569 B2 | 8/2006 | Boulanger et al. |
| 7,144,391 B1 | 12/2006 | Kreutz et al. |
| 7,235,044 B2 | 6/2007 | Forsell |
| 7,258,661 B2 | 8/2007 | Davies et al. |
| 7,306,586 B2 | 12/2007 | Beaufore et al. |
| 7,311,661 B2 | 12/2007 | Heinrich |
| 7,360,544 B2 | 4/2008 | Levien |
| 7,445,598 B2 | 11/2008 | Orban, III |
| 7,540,876 B2 | 6/2009 | Connors et al. |
| 7,553,273 B2 | 6/2009 | Ferguson et al. |
| 7,628,155 B2 | 12/2009 | Carey |
| 7,628,156 B2 | 12/2009 | Astani et al. |
| 7,658,196 B2 | 2/2010 | Ferreri et al. |
| 7,673,631 B2 | 3/2010 | Astani et al. |
| 7,691,051 B2 | 4/2010 | Connors et al. |
| 7,695,427 B2 | 4/2010 | Kugler et al. |
| 7,717,892 B2 | 5/2010 | Bartning et al. |
| 7,722,583 B2 | 5/2010 | Kim et al. |
| 7,771,344 B2 | 8/2010 | Ziv |
| 7,771,346 B2 | 8/2010 | Burton et al. |
| 7,775,215 B2 | 8/2010 | Hassler, Jr. et al. |
| 7,775,966 B2 | 8/2010 | Dlugos et al. |
| 7,794,385 B2 | 9/2010 | Rosenblatt |
| 7,819,821 B2 | 10/2010 | Forte et al. |
| 7,828,713 B2 | 11/2010 | Ziv et al. |
| 7,828,714 B2 | 11/2010 | Feng et al. |
| 7,828,715 B2 | 11/2010 | Haverfield |
| 7,828,716 B2 | 11/2010 | Burton et al. |
| 7,844,342 B2 | 11/2010 | Dlugos, Jr. et al. |
| 7,892,163 B2 | 2/2011 | Bartning et al. |
| 7,927,270 B2 | 4/2011 | Dlugos et al. |
| 7,927,320 B2 | 4/2011 | Goldwasser et al. |
| 8,740,766 B2 | 6/2014 | Rosen et al. |
| 8,740,767 B2 | 6/2014 | Rosen et al. |
| 2002/0183833 A1 | 12/2002 | Stevens et al. |
| 2004/0030217 A1* | 2/2004 | Yeung ............ A61B 17/06066 600/31 |
| 2006/0025798 A1 | 2/2006 | Cook et al. |
| 2006/0211911 A1 | 9/2006 | Jao et al. |
| 2007/0203429 A1 | 8/2007 | Ziv |
| 2008/0033231 A1 | 2/2008 | Bartning et al. |
| 2009/0111671 A1 | 4/2009 | Campbell et al. |
| 2009/0192346 A1 | 7/2009 | Rosenblatt |
| 2009/0216071 A1 | 8/2009 | Zipper |
| 2009/0266367 A1* | 10/2009 | Ziv .................. A61F 2/005 128/834 |
| 2009/0283099 A1 | 11/2009 | Harmanli |
| 2011/0015474 A1 | 1/2011 | Forsell |
| 2012/0116415 A1 | 5/2012 | Forsell |
| 2013/0012764 A1 | 1/2013 | Herbowy et al. |
| 2013/0138135 A1* | 5/2013 | Rosen .............. A61B 17/12 606/197 |
| 2013/0144112 A1 | 6/2013 | Rosen et al. |
| 2013/0150661 A1 | 6/2013 | Rosen et al. |

FOREIGN PATENT DOCUMENTS

| | | |
|---|---|---|
| EP | 1518514 | 3/2005 |
| EP | 1587464 | 8/2007 |
| EP | 1587465 | 11/2007 |
| EP | 160944 | 7/2008 |
| EP | 1734895 | 7/2008 |
| EP | 1734892 | 3/2011 |
| EP | 1990023 | 9/2012 |
| FR | 2843700 | 2/2004 |
| GB | 2352181 | 1/2001 |
| WO | WO1993/016659 | 9/1993 |
| WO | WO1996/001084 | 1/1996 |
| WO | WO2001/045487 | 6/2001 |
| WO | WO2002/053235 | 7/2002 |
| WO | WO2002/098323 | 12/2002 |
| WO | WO2005/082276 | 9/2005 |
| WO | WO2008/085825 | 7/2008 |
| WO | WO2009/046996 | 4/2009 |
| WO | WO2009/046997 | 4/2009 |
| WO | WO2009/060437 | 5/2009 |
| WO | WO2011/008167 | 1/2011 |
| WO | WO2011/116108 | 9/2011 |
| WO | WO 2011116108 A1 * | 9/2011 ........... A61F 2/0009 |

OTHER PUBLICATIONS

Sokol et al; Clinical Anatomy of the Vulva, Vagina, Lower Pelvis, and Perineum; Global Library of Women's Medicine; 14 pgs.; Sep. 2008 (printed from http://www.glowm.com/section_view/heading/Clinical%20Anatomy%200f%20the%20V on Dec. 23, 2013).

Viera et al.; Practical use of the pessary; Am Fam Physician; 61(9); pp. 2719-2726; May 1, 2000 (downloaded Mar. 8, 2013 from: http://www.aafp.org/afp/2000/0501/p2719.html?printable=afp).

* cited by examiner

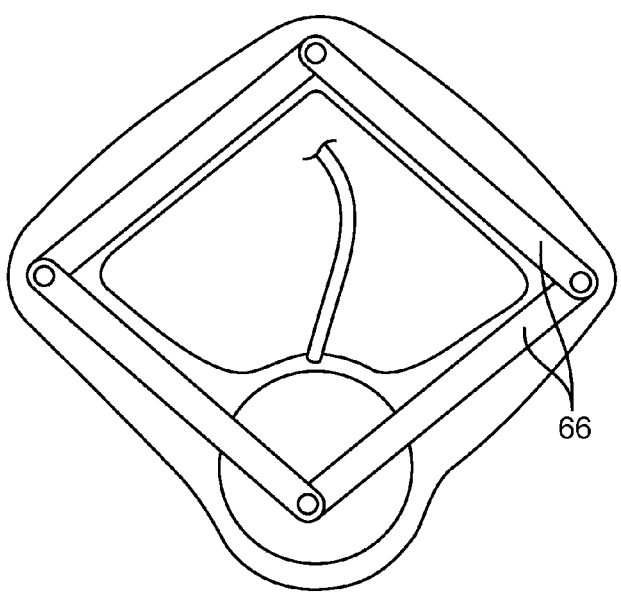
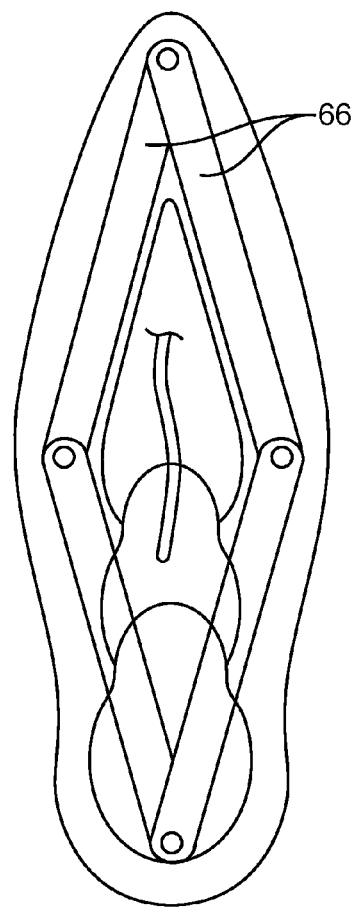
FIG. 5A
FIG. 5B

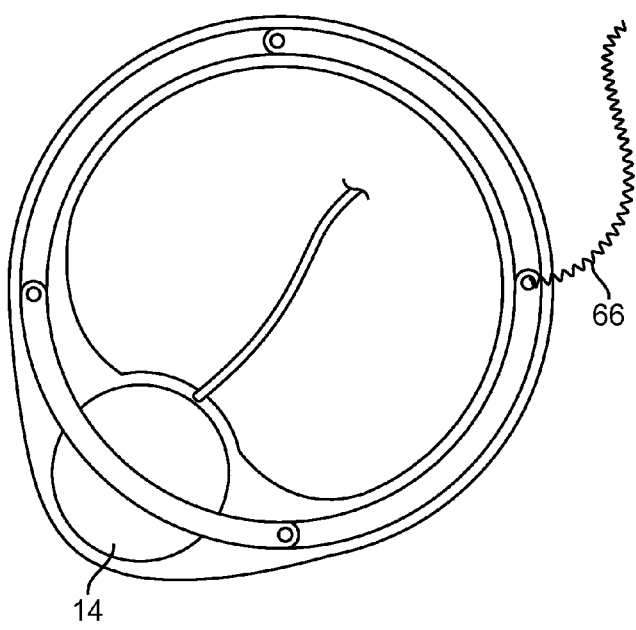
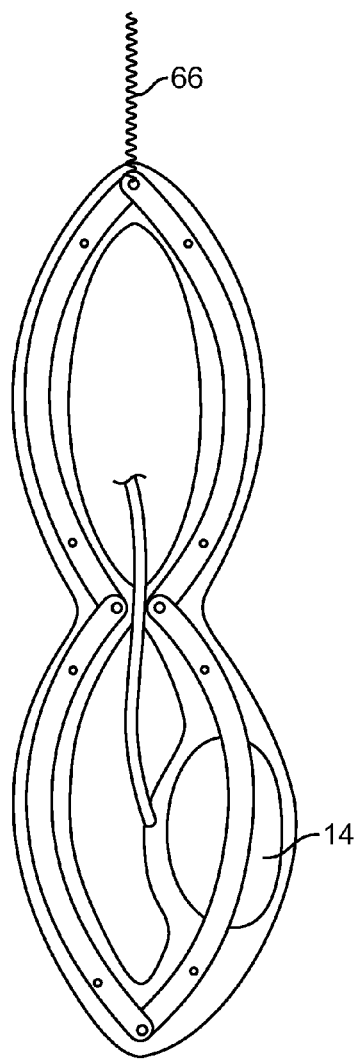
FIG. 8A
FIG. 8B

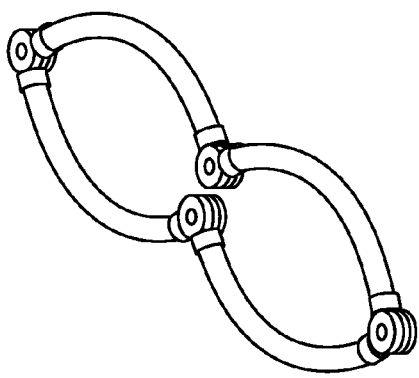
FIG. 20C
FIG. 20B
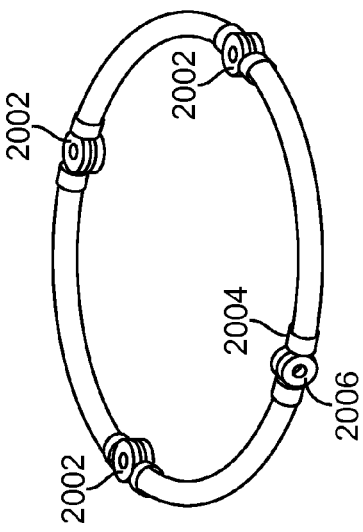
FIG. 20A

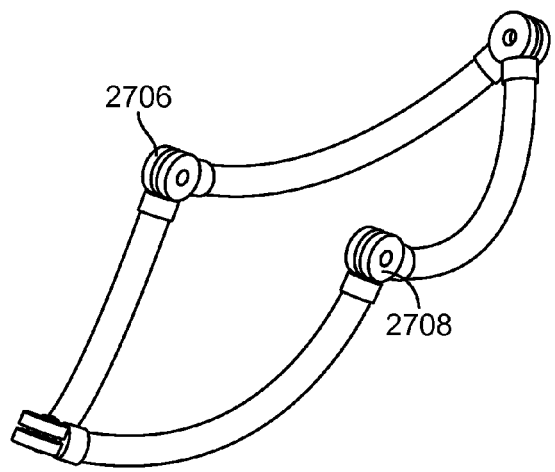
FIG. 27D
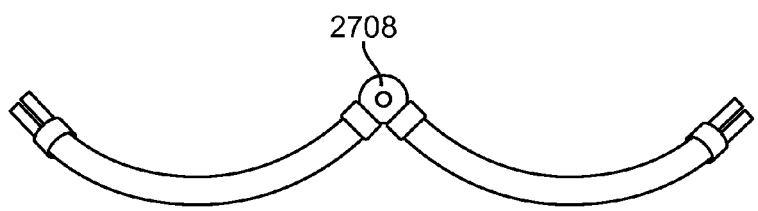
FIG. 27E
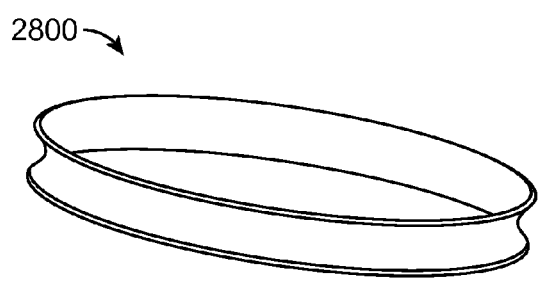
FIG. 28A
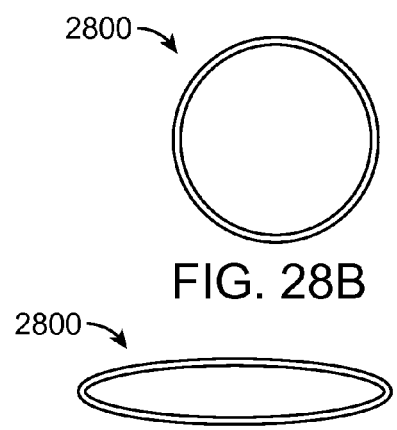
FIG. 28B
FIG. 28C $X_1 = X_2$ $X_1 > X_2$

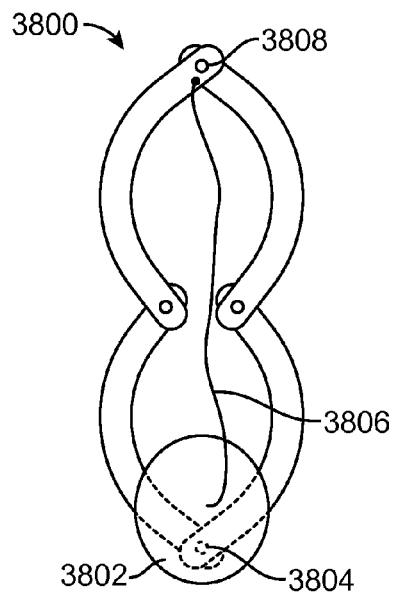
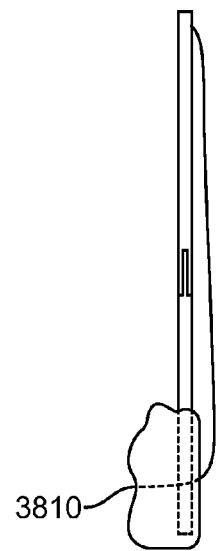
FIG. 38A
FIG. 38B
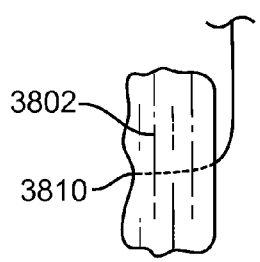
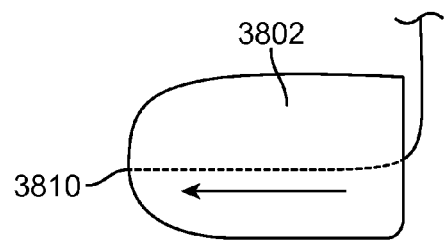
FIG. 38C
FIG. 38D
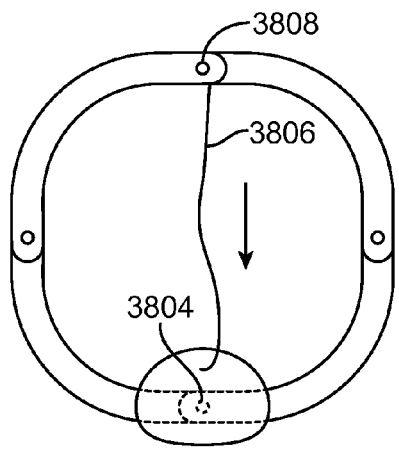
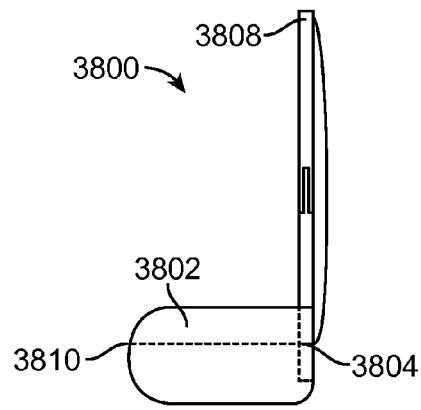
FIG. 38E
FIG. 38F

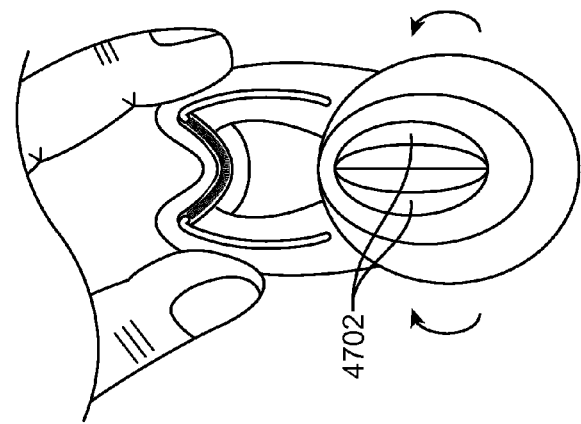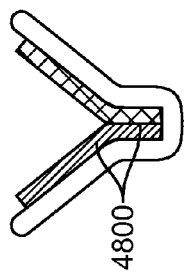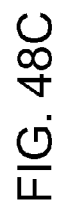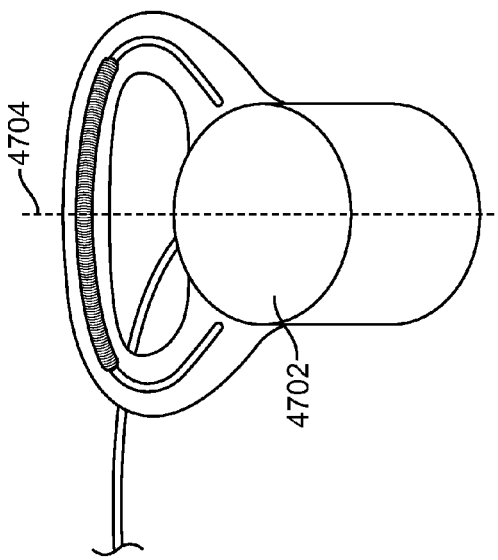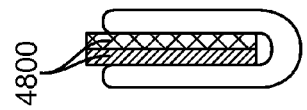

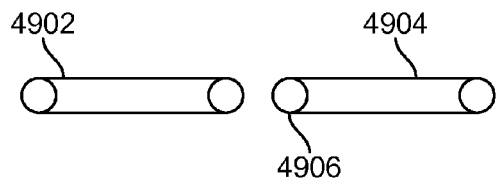
FIG. 49A
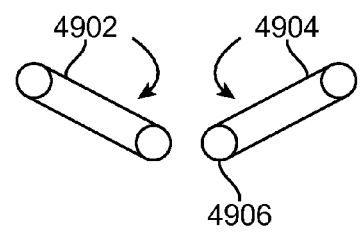
FIG. 49B
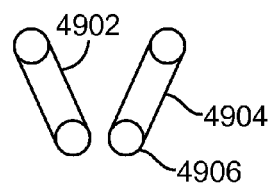
FIG. 49C
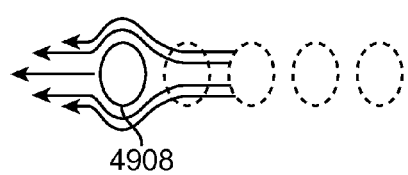
FIG. 49D
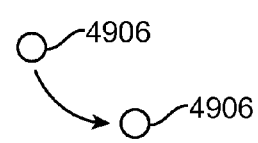
FIG. 49E
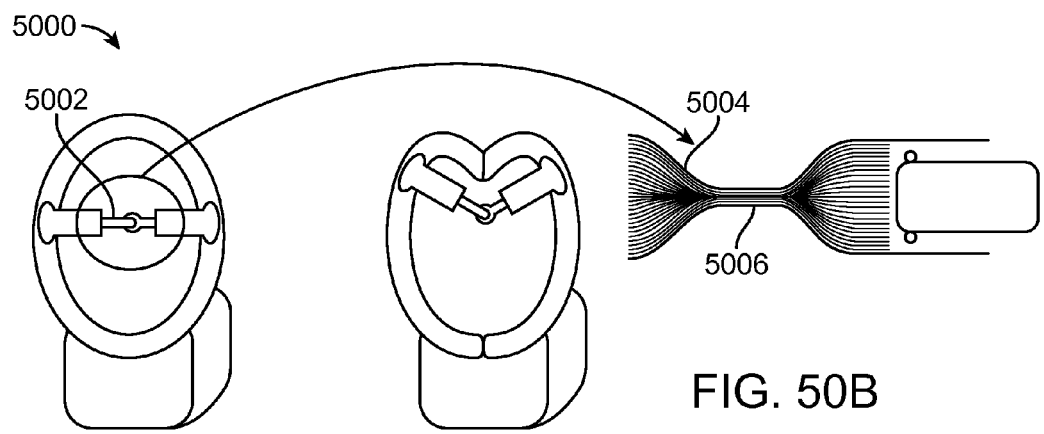
FIG. 50A
FIG. 50B

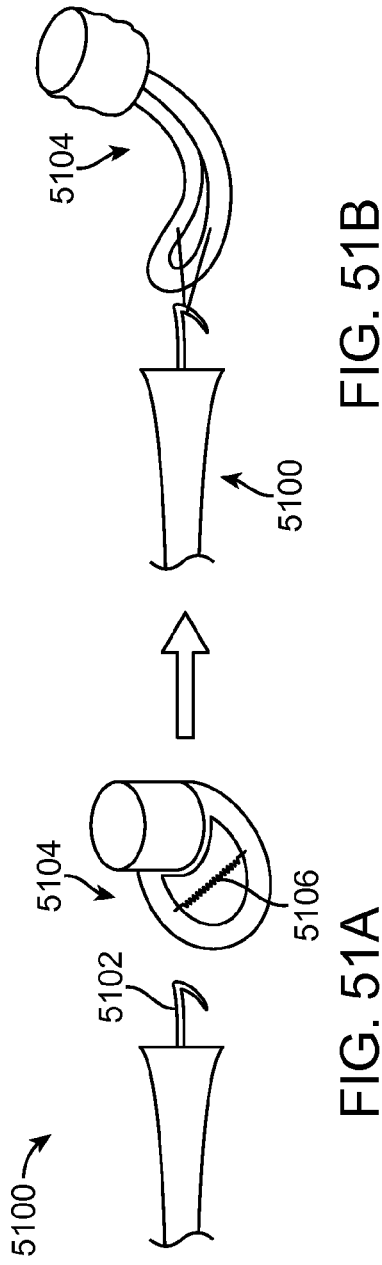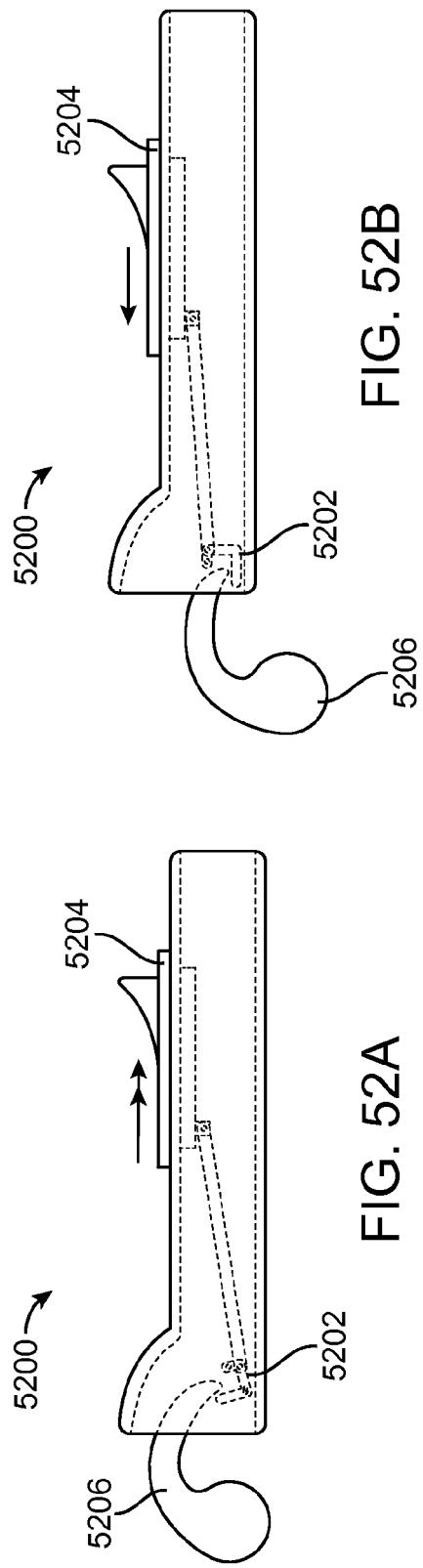

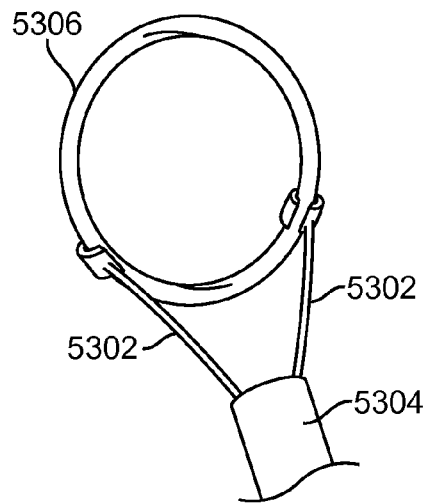
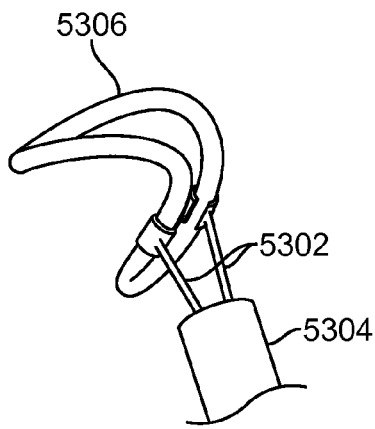
FIG. 53A    FIG. 53B
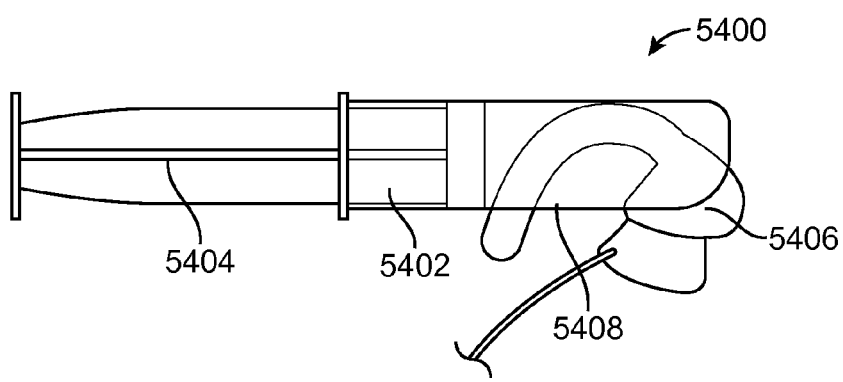
FIG. 54A
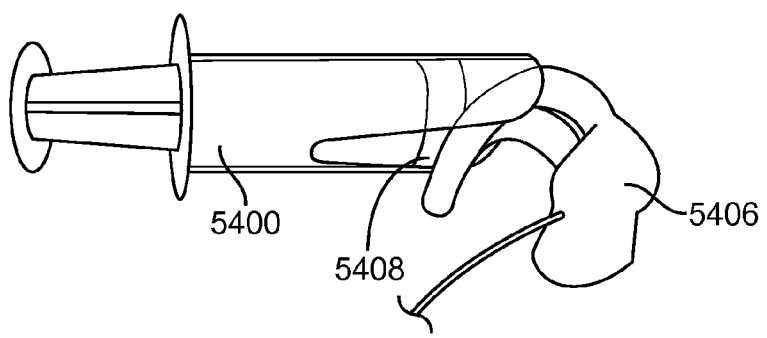
FIG. 54B

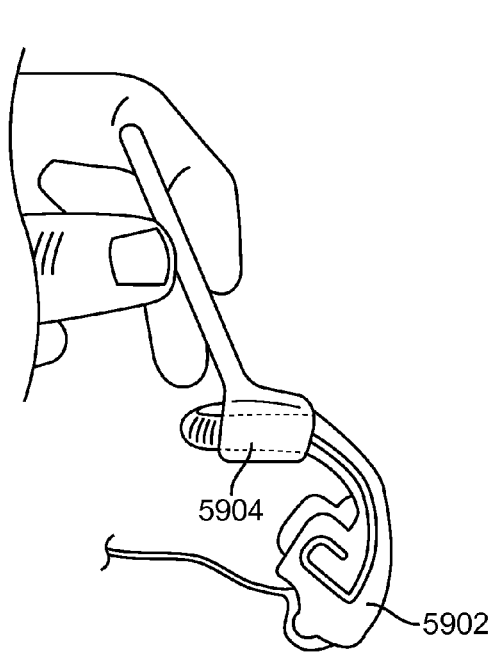
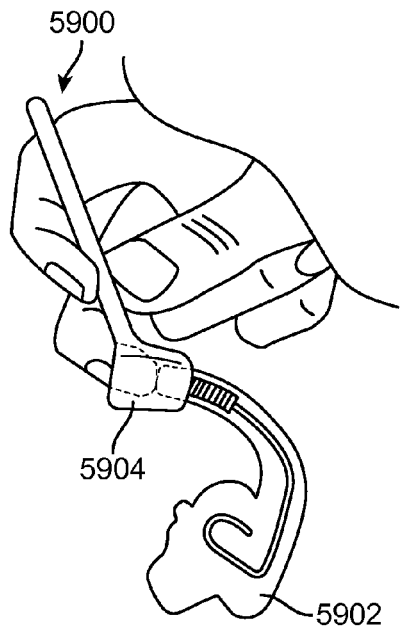
FIG. 59D
FIG. 59E
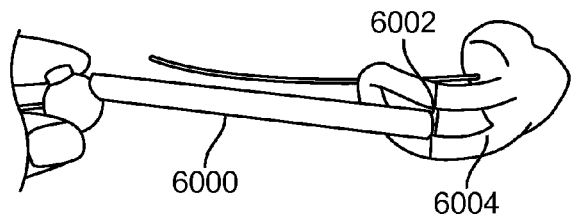
FIG. 60A
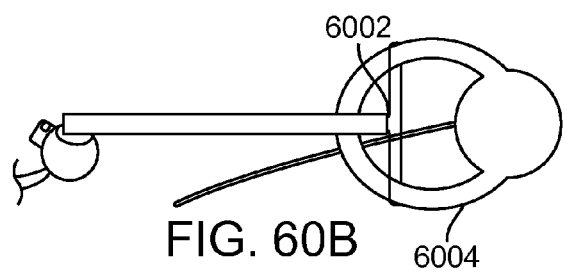
FIG. 60B
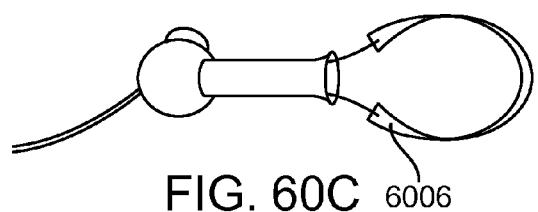
FIG. 60C

INTRA-VAGINAL DEVICES AND METHODS FOR TREATING FECAL INCONTINENCE

CROSS REFERENCE TO RELATED APPLICATIONS

This application claims the benefit of U.S. Provisional Application No. 61/764,960, filed Feb. 14, 2013, and entitled "VAGINAL BOWEL CONTROL DEVICES AND METHODS OF USE".

INCORPORATION BY REFERENCE

All publications and patent applications mentioned in this specification are herein incorporated by reference to the same extent as if each individual publication or patent application was specifically and individually indicated to be incorporated by reference.

FIELD

This application relates to the field of intra-vaginal devices for the treatment of fecal incontinence.

BACKGROUND

Fecal incontinence (FI) is one of the most common health problems in women. The prevalence of FI is not well understood, primarily because the stigma surrounding the condition and the lack of viable treatments have deterred many women from seeking medical care. Recent general population surveys indicate the prevalence of FI at 9% to 12% and as high as 24% in older women. These studies have also shown that, although prevalence increases somewhat with age, younger women have surprisingly high prevalence rates. The condition is both physically limiting and emotionally devastating. Those afflicted are often forced to withdraw from social and professional activities and often face problems in their private personal relationships.

The cause of FI is multifactorial and not completely understood. Often times, women with FI have a history of damage to the pelvic floor stemming from pregnancy and childbirth. Damage can involve the internal and external anal sphincters, pelvic floor muscles, and associated nerves (e.g., pudendal nerve). Puerperal damage to these structures may not manifest until later in life, possibly due to age-related changes in rectal sensation, compliance, and volume, in addition to further weakening of the sphincters and pelvic floor muscles. Many women with FI have multiple defects in their continence system, making effective treatment particularly difficult.

Existing treatments include conservative management, surgical procedures, and permanent implants. These treatments all have limitations in efficacy and morbidity and most of the women with fecal incontinence go untreated. There is the need for a new therapy that is low-risk and offers a high degree of benefit. Disclosed in this application is a new way of treating fecal incontinence. Described is a non-surgical intravaginal device that can protrude into the rectum and prevent accidental bowel leakage.

SUMMARY OF THE DISCLOSURE

In one aspect, an intravaginal device for the control of stool passage is provided. The device comprises a collapsible stabilizing body including a plurality of segments interconnected by joints and configured to modulate between an open state and a collapsed state by movement of the segments about the joints; an occluding portion positioned above the stabilizing body, the occluding body configured to provide a non-extended state and a extended state, the occluding body configured to occlude the rectum by pushing against a recto-vaginal septum of a user in the extended state; and a locking mechanism configured to maintain the collapsible stabilizing body in the open state upon engagement of the locking mechanism and permit the collapsible stabilizing body to collapse upon disengagement of the locking mechanism.

In some embodiments, the interconnected segments, in the open state, form a loop with a generally oval shape. In some embodiments, the interconnected segments, in the collapsed state, form a loop with multiple generally oval shapes. In some embodiments, in the collapsed state the segments have a lengthwise mid-point that is approximately half-way between a distal joint and proximal joint, wherein a width at this midpoint in the collapsed state is narrower than a width of a space spanned by the segments both proximal and distal to the midpoint. In some embodiments, in the collapsed state, the approximate lengthwise midpoint forms a local minimum in the profile of the device. In some embodiments, the occluding portion is configured to protrude into the rectum by pushing against a recto-vaginal septum of a user in the extended state. In some embodiments, in the open state, the device has a first width, a first length, and a first height; and in the collapsed state, the device has a second width, a second length, and a second height, the second width being 50% less than the first width, the second length being greater than the first length, and the second height being substantially the same as the first height. In some embodiments, the stabilizing body is comprised of multiple interconnected segments that are joined together to form a loop. In some embodiments, the stabilizing body comprises multiple interconnected segments that are joined by joints, wherein at least one of the joints comprises an elastomeric material. In some embodiments, at least a portion of at least some of the plurality of segments have an arcuate shape. In some embodiments the plurality of segments is arranged symmetrically about an axis that extends between the locking mechanism and the occluding portion. In some embodiments, a portion of the collapsible stabilizing body has an arcuate shape and a portion of the collapsible stabilizing body has a linear shape. In some embodiments, the occluding portion is an inflatable balloon, extending from the joint in a generally perpendicular direction from a plane of the interconnected segments, wherein the joint is located between the balloon and a soft cushion material. In some embodiments, the occluding portion is positioned above the linearly shaped portion of the collapsible stabilizing body. In some embodiments, the occluding portion is attached to the periphery. In some embodiments, the collapsible stabilizing body is configured to provide an interconnected frame solely forming a structural perimeter of the device. In some embodiments, the interconnected frame is comprised of metal segments, joined together and surrounded by a soft cushioning material. In some embodiments, at least 3 of the interconnected joints are configured to be constrained to one degree of freedom of angular motion. In some embodiments, the collapsible stabilizing body is configured to resist out-of-plane bending. In some embodiments, joints of the interconnected segments are configured to constrain the interconnected segments to rotational motion in a plane of the frame. In some embodiments, the occluding portion is positioned above a joint between interconnected segments. The occluding portion can be coupled to the collapsible stabilizing body by a flexible coupling. The occluding portion can be positioned above a joint located opposite to the locking mechanism. The occluding portion can comprise a support member that is connected to the collapsible stabilizing body, wherein the support member spans less than 50% of a distance across a longitudinal span of the stabilizing body in the open state. In some embodiments, in the open state, the collapsible stabilizing body has a first width and a first length; and in the collapsed state, the collapsible stabilizing body has a second width and a second length, the second width being less than the first width and the second length being greater than the first length. In some embodiments, in the open state, the device has a first width, a first length, and a first height; and in the collapsed state, the device body has a second width, a second length, and a second height, the second width being less than the first width, the second length being greater than the first length, and the second height being substantially the same as the first height. The plurality of segments can comprise at least six segments. In some embodiments, the plurality of segments comprises at least four segments. In some embodiments, the stabilizing body comprises an outer profile, and wherein the interconnected segments deviate from the outer profile at a proximal portion of the stabilizing body. In some embodiments, the devices comprises an encapsulating material disposed around the collapsible stabilizing body, the encapsulating material having a first thickness between the interconnected segments and an exterior surface of the stabilizing body in regions disposed away from the occluding portion and a second thickness between the interconnected segments and an exterior surface of the stabilizing body in regions disposed proximate to the occluding portion, the second thickness being greater than the first thickness. In some embodiments, the device comprises a tensile element attached to the locking mechanism, the tensile element configured to permit disengagement of the locking mechanism via application of force to the tensile element. In some embodiments, the tensile element is operatively connected to an inflation lumen that communicates with the occluding portion. The tensile element can comprise a string, tube, cable, wire, or cord. In some embodiments, the plurality of segments includes a first arcuate segment; a second arcuate segment moveably connected to the first arcuate segment; a third segment having an arcuate portion and a linear portion, the third segment being moveably connected to the first segment; and a fourth segment having an arcuate portion and a linear portion, the fourth segment being moveably connected to both the third segment and the second segment. In some embodiments, the interconnected segments move in-plane with a first amount of force, and in the open state, the interconnected segments move out-of-plane with a second amount of force, wherein the first amount of force is less than the second amount of force.

In another aspect, a method of controlling stool passage in a user is provided. The method comprises inserting an intra-vaginal device in the user's vagina, the device comprising a collapsible stabilizing body including a plurality of segments interconnected by joints, and an occluding portion, the collapsible stabilizing body being in a collapsible state during insertion; moving the interconnected segments about the joints to modulate the collapsible stabilizing body to an open state; locking the collapsible stabilizing body in the open state; extending the occluding portion against a rectovaginal septum of the vagina to at least partially occlude the user's rectum; and retracting the occluding portion while the stabilizing body is open to permit stool to pass through the rectum.

In some embodiments, the method comprises applying force to a tensile element attached to the locking mechanism, unlocking the collapsible stabilizing body from the open state. In some embodiments, the tensile element is part of an inflation tube.

In another aspect, an intravaginal device for the control of stool passage of an adult human female user is provided. The device comprises an expandable occluding body; and an intravaginal stabilizing body supporting the occluding body to maintain position and stability of the occluding body in the user's vagina during repeated expansions of the occluding body in an extension direction to contact the user's rectovaginal septum to at least partially occlude the rectum, the stabilizing body comprising a locking mechanism, the stabilizing body having a collapsible configuration and a stable open configuration in which the stabilizing body is held open by the locking mechanism.

In some embodiments, the stabilizing body comprises a plurality of arms connected to form a loop. In some embodiments, the stabilizing body comprises 4 arms. In some embodiments, the stabilizing body has a generally ovular shape. In some embodiments, in the open configuration, the occluding body is disposed at a location of the stabilizing body having a width less than the maximum width of the stabilizing body. In some embodiments, a thickness of the stabilizing body in the extension direction is less than the length of the occluding body in the extension direction. In some embodiments, in the collapsible configuration, the occluding body is supported so that it is disposed in a space between portions of the stabilizing body. In some embodiments, wherein the stabilizing body is configured to collapse along its length as it moves from the open configuration the collapsible configuration. In some embodiments, the stabilizing body comprises two arms connected by a hinge, the locking mechanism configured to prevent or permit movement of the hinge. In some embodiments, the locking mechanism comprises a latch that is configured to move into and out of a pocket positioned proximate to the hinge between two arms, wherein the latch being positioned in the pocket prevents the two arms from moving relative to one another. In some embodiments, the hinge and the latch are configured to rotate about a same point. In some embodiments, the latch is connected to the stabilizing body by a pin joint and is configured to rotate into the pocket. In some embodiments, the locking mechanism comprises a rotatable joint positioned between two arms configured to allow the opening or closing of the stabilizing body upon rotation of the joint. In some embodiments, the locking mechanism comprises at least one resilient member extending across the stabilizing body, holding the stabilizing body open when the resilient member is in a resting state. In some embodiments, in the resting state, the resilient member is configured to hold the stabilizing body open to a degree greater than the degree desired when the device is inserted in the patient's vaginal cavity. In some embodiments, the locking mechanism comprises a detent on an end of a first arm configured to catch on a feature of an end of a second arm. In some embodiments, the detent comprises at least one of a spring loaded ball or a leaf spring. In some embodiments, the feature comprises at least one of an edge of the second arm or a feature shaped to mate with the detent. In some embodiments, the device comprises a stable collapsed configuration and a stable open configuration. In some embodiments, at least two of the plurality of arms have a first configuration in which the at least two arms extend inwardly towards a center of the stabilizing body and a second configuration in which the at least two arms extend outwardly away from the center of the stabilizing body. In some embodiments, the locking mechanism comprises a bistable component extending between a first arm and a second arm of the stabilizing body. In some embodiments, the bistable component comprises a hinge connecting the first arm and the second arm. In some embodiments, a resilient member extends between a first end of the first arm and a second end of the second arm, the resilient member configured to be in a first tensioned state when the stabilizing body is in the open configuration or the collapsible configuration and a second tensioned state when moving between the open and collapsible configurations, wherein the second tensioned state is higher than the first tensioned state. In some embodiments, the device is configured to collapse into two sections in the collapsed configuration. In some embodiments, the device is configured to collapse into more than two sections in the collapsed configuration. In some embodiments, the locking mechanism comprises an opening on a first end of a first arm configured to catch an extension on a second end of a second arm. In some embodiments, the stabilizing body is configured to collapse by folding together. In some embodiments, the stabilizing body comprises two hinges configured to allow the stabilizing body to fold. In some embodiments, the stabilizing body comprises two additional hinges configured to allow the folded stabilizing body to straighten. In some embodiments, the two additional hinges are joints, rotatable only upon folding of the stabilizing body. In some embodiments, the stabilizing body comprises a shape memory alloy comprising a transition temperature other than body temperature. In some embodiments, the shape memory alloy is configured to change shape upon application of temperature or current. In some embodiments, the locking mechanism comprises at least two internal structures with flexible portions, movable relative to one another, configured to facilitate device collapse upon alignment of the flexible portions. In some embodiments, the stabilizing body comprises multiple frame segments with a tensile member passed through the frame segments. In some embodiments, the locking mechanism comprises a hinge with a sheath movable to cover or expose the hinge, wherein exposure of the hinge allows movement of the hinge. In some embodiments, the sheath is configured to prevent motion of the hinge when the sheath covers the hinge. In some embodiments, the device comprises a triggering mechanism configured to transition the stabilizing body to the collapsible state. In some embodiments, the triggering mechanism is located proximate to an inflation lumen connected to the occluding body. In some embodiments, the triggering mechanism is coupled to the inflation lumen. In some embodiments, the device comprises an elastomeric portion distal to the triggering mechanism.

In another aspect, a method of selectively occluding a rectum to inhibit stool passage in a female user is provided. The method comprises inserting an intravaginal device into the user's vagina, the device comprising a stabilizing body and an occluding portion, the stabilizing body being collapsible during insertion; moving the stabilizing body to an open configuration; engaging vaginal anatomy with the stabilizing body in the open configuration to stably support the occluding portion; locking the stabilizing body in the open configuration; extending the occluding portion against a recto-vaginal septum of the vagina body during the engaging step to at least partially occlude the user's rectum; and retracting the occluding portion during while the stabilizing body is in the open configuration to permit stool to pass through the rectum.

In some embodiments, the method comprises pulling on a distal portion of the intravaginal device, thereby causing the stabilizing body to collapse from the open configuration to the collapsed configuration. In some embodiments, the method comprises removing the device from the user's vagina. In some embodiments, pulling on a distal portion of the intravaginal device comprises pulling on a tensile element attached to a distal portion of the device. In some embodiments, the tensile element comprises a string, cord, or reinforced tube. In some embodiments, the extending step comprises inflating the occluding portion to a pressure of 40-150 mm Hg. In some embodiments, the engaging step comprises engaging internal vaginal anatomy to stably support the occluding body proximal to the vagina's perineal body while maintaining slack in the vagina wall. In some embodiments, the engaging step comprises distending lateral walls of the vagina proximate to the occluding portion less than in areas not proximate to the occluding body.

In another aspect, an intravaginal device is provided. The device comprises an occluding portion; and a resilient, deformable, intravaginal stabilizing body supporting the occluding portion, the intravaginal stabilizing body comprising a collapsed configuration in which a first portion and a second portion of the stabilizing body are folded together and an open configuration, wherein the stabilizing body is biased towards the open configuration, wherein the first portion comprises a first material, the second portion comprises a second material, the first and second materials selected to allow the first and second portions to resist separation upon release of the stabilizing body from the collapsed configuration, thereby dampening opening of the stabilizing body.

In some embodiments, the first portion comprises the first material, the first portion is coated with the first material, or the first portion is treated with the first material. In some embodiments, the second portion comprises the second material, the second portion is coated with the second material, or the second portion is treated with the second material. In some embodiments, the first material and the second material comprise silicone.

In another aspect, an intravaginal device is provided. The device comprises an occluding portion; and a resilient, deformable, intravaginal stabilizing body supporting the occluding portion, the intravaginal stabilizing body comprising a collapsed configuration in which a first portion and a second portion of the stabilizing body are folded together and an open configuration, wherein the stabilizing body is biased towards the open configuration, wherein the first portion comprises a first characteristic, the second portion comprises a second characteristic, the first and second characteristics selected to allow the first and second portions to resist separation upon release of the stabilizing body from the collapsed configuration. In some embodiments, at least one of the first characteristic and the second characteristic comprises an adherence feature. In some embodiments, the adherence feature comprises at least one of a hook and loop feature and a micro-suction feature.

In another aspect, an intravaginal device for the control of stool passage of an adult human female user is provided. The device comprises an occluding portion; and an intravaginal stabilizing body supporting the occluding portion, the stabilizing body comprising a collapsed configuration and an open configuration, the stabilizing body comprising at least a first and a second arm connected at a joint, wherein the joint comprises a dampening mechanism.

In some embodiments, the dampening mechanism comprises a viscous fluid surrounding the joint between the first arm and the second arm. In some embodiments, the dampening mechanism comprises a hydraulic dampening mechanism.

In another aspect, a method of inserting an intravaginal device in a user is provided. The method comprises inserting, in a collapsed configuration, an intravaginal device into the user's vagina, the device having a bias towards an open configuration; releasing the device from the collapsed configuration; and dampening movement of the device from the collapsed configuration to the open configuration.

In some embodiments, the method comprises adhering a first part of the device to a second part of the device, allowing the device bias to overcome the adhering.

In another aspect, an intravaginal device for the control of stool passage of an adult human female user is provided. The device comprises an expandable, occluding portion; and an intravaginal stabilizing body supporting the occluding portion having tissue engagement surfaces sized and shaped to engage with internal vaginal anatomy to maintain position and stability of the occluding body in the user's vagina during repeated expansions of the occluding portion in an extension direction to contact the user's rectovaginal septum to at least partially occlude the rectum, the stabilizing body comprising a collapsed and an open configuration, the stabilizing body comprising a retaining feature configured to hold the stabilizing body in the collapsed configuration.

In some embodiments, the retaining feature comprises a latch configured to hold two portions of the stabilizing body together. In some embodiments, the latch is configured to release when the two portions are squeezed together. In some embodiments, two portions of the stabilizing body comprise press fit features configured to mate with each other. In some embodiments, the stabilizing body comprises a tensile member configured to draw at least two portions of the stabilizing body together upon application of tension to the tensile member. In some embodiments, the tensile member comprises a wire, cord, or string. In some embodiments, the tensile member comprises a holding feature configured to maintain tension on the tensile member.

In another aspect, a method of selectively occluding a rectum to inhibit stool passage in a female user is provided. The method comprises inserting an intravaginal device into the user's vagina, the device comprising a stabilizing body and an occluding portion, inserting the device comprising maintaining the stabilizing body in a collapsed configuration by engaging a retaining feature on the stabilizing body; engaging vaginal anatomy to stably support the occluding portion proximal to the vagina's perineal body; releasing the device from the collapsed configuration; extending the occluding portion against a recto-vaginal septum of the vagina proximal to the vagina's perineal body during the engaging step to at least partially occlude the user's rectum; and retracting the occluding portion during the engaging step to permit stool to pass through the rectum.

In some embodiments, the maintaining step comprises engaging a latch, thereby holding two portions of the stabilizing body together. In some embodiments, the releasing step comprises squeezing the two portions together. In some embodiments, the maintaining step comprises mating a first press fit feature on a first portion of the stabilizing body with a second press fit feature on a second portion of the stabilizing body. In some embodiments, the maintaining step comprises applying tension to a tensile member, thereby drawing two portions of the stabilizing body together.

In another aspect, an applicator for inserting an intravaginal device in a user's vagina is provided. The applicator comprises a retaining feature configured to hold the intravaginal device in a folded configuration, the intra-vaginal device comprising an expandable occluding portion and a stabilizing body configured to support the occluding portion, the folded configuration having a round shape; and a trigger feature configured to release the intra-vaginal device to position the occluding portion such that the occluding portion can engage the recto-vaginal septum and can expand to occlude the rectum.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5A-B illustrate an embodiment of a collapsible intra-vaginal device.

FIGS. 8A-B illustrate an embodiment of a collapsible intra-vaginal device.

FIGS. 20A-C illustrate an embodiment of a collapsible device frame.

FIGS. 27A-E illustrate an embodiment of a collapsible device frame.

FIGS. 28A-C illustrate an embodiment of a collapsible device frame.

FIGS. 38A-F illustrate an embodiment of a device configured to be driven open by expandable member.

FIGS. 47A-B illustrate an embodiment of an intra-vaginal device comprising dampening properties.

FIGS. 48A-C illustrate an embodiment of an intra-vaginal device comprising adherence features.

FIGS. 49A-E illustrates an embodiment of a dampening mechanism.

FIGS. 50A-B illustrates an embodiment of a dampening mechanism.

FIGS. 51A-B illustrate an embodiment of an applicator for an intra-vaginal device.

FIGS. 52A-B illustrate an embodiment of an applicator for an intra-vaginal device.

FIGS. 53A-B illustrate an embodiment of an applicator for an intra-vaginal device.

FIGS. 54A-C illustrate an embodiment of an applicator for an intra-vaginal device.

FIGS. 59A-E illustrate an embodiment of a tool for controlling and positioning an intra-vaginal device.

FIGS. 60A-C illustrate an embodiment of a tool for controlling and positioning an intra-vaginal device.

DETAILED DESCRIPTION

Figure 1A:
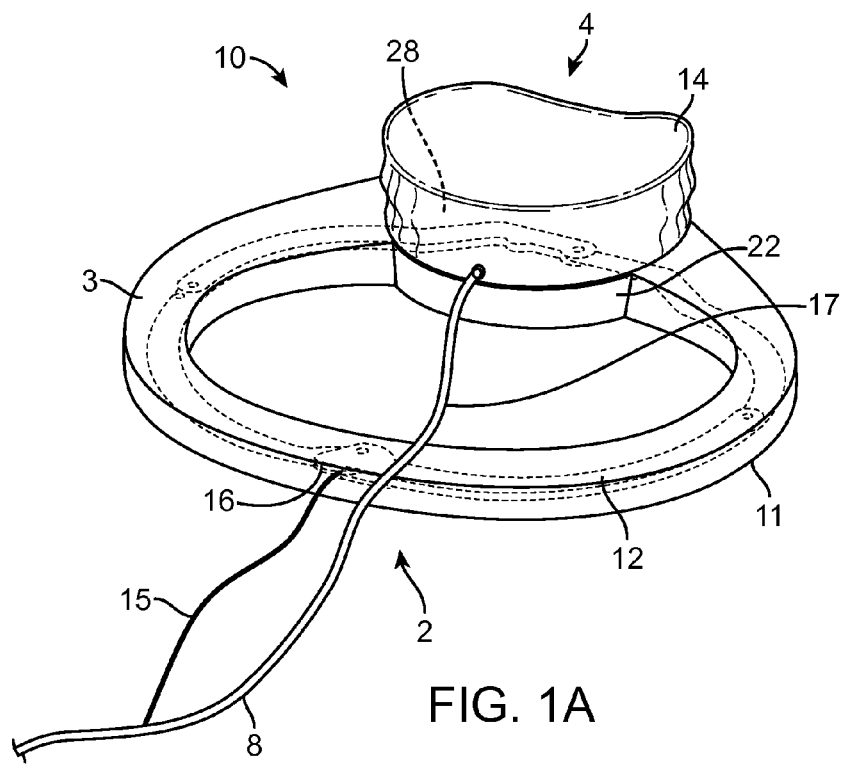
FIGS. 1A-E illustrate an embodiment of a collapsible intra-vaginal device.

The disclosure herein relates generally to intra-vaginal devices and methods for controlling the passage of stool. The devices are adapted to at least partially occlude the rectum to control the passage of stool while remaining stable inside the vagina.

Extensive human clinical trials were performed in order to understand key attributes for devices that will achieve the desired vaginal bowel control (VBC). First, the ability for users (patients and clinicians) to easily insert and remove the device is a priority for successful treatment. If patients cannot manage the use of the device, it cannot be used to control the passage of stool. Second, the ability to achieve rectal occlusion was found to be influenced by a variety of design features that were unanticipated from knowledge of the anatomy. Third, the stability of the device not only during rectal occlusion but also when the device is not occluding the rectum turned out to be a key aspect of device function and required specific adaptations to ensure the device is stabilized when it is not occluding and when it is occluding. Finally, the devices have to be adapted to interact with the tissue in a way that is comfortable and safe to the user while achieving occlusion and stability. Through bench and human clinical testing, these discoveries of how device design impacted device performance including rectal occlusion, device stability, and user safety and comfort, led to the development of inventive and effective vaginal bowel control devices.

Exemplary intra-vaginal devices and methods are described in U.S. Publication No. 2013/0150661 (application Ser. No. 13/625,683), filed Sep. 24, 2012, entitled "INTRA-VAGINAL DEVICES AND METHODS FOR TREATING FECAL INCONTINENCE"; U.S. Publication No. 2013/0138135 (application Ser. No. 13/679,484), filed Nov. 16, 2012, entitled "INTRA-VAGINAL DEVICES AND METHODS FOR TREATING FECAL INCONTINENCE"; U.S. Publication No. 2013/0144112 (application Ser. No. 13/679,528), filed on Nov. 16, 2012, entitled "INTRA-VAGINAL DEVICES AND METHODS FOR TREATING FECAL INCONTINENCE"; International Publication No. WO 2011/116108 (Int'l. App No. PCT/US2011/028691), filed on Mar. 15, 2011, entitled "INTRA-VAGINAL DEVICE FOR FECAL INCONTINENCE"; and International Publication No. WO 2013/044239 (Int'l App. No. PCT/US2012/056923), filed Sep. 24, 2012, entitled "INTRA-VAGINAL DEVICES AND METHODS FOR TREATING FECAL INCONTINENCE", the disclosures of which are incorporated herein in their entireties. These applications will herein be referred to collectively as "Earlier Applications".

Collapsible Devices

Vaginal devices can be used for many applications, including fecal incontinence, urinary incontinence, pelvic organ prolapse, other bowel control issues such as IBS, administration of hormones and pharmaceuticals, control of bleeding, physical therapy, and control of menstrual flow. In order to aid in insertion and removal from the vagina, some vaginal devices can be elastically deformed for insertion and removal, but require a user to continually apply force as the device is inserted. This can be difficult for the user and can result in an uncomfortable sensation when the device returns (usually quickly and via spring force) to an un-deformed state. Similarly, when being removed, the vagina provides the force to deform the device to a smaller profile, which can be uncomfortable for the user (or the device is removed in its un-collapsed shape). Often, a patient is using her hands to manipulate the device into a smaller profile for insertion. It can be difficult for the user to hold the device in this manner for insertion and to reach the device for removal. Additionally, it can be difficult to control the release of the device in order to avoid the uncomfortable sensation of it opening once it is inside the vagina.

It can be important for such devices to strike a balance in which the device is easy enough to deform for insertion and removal, but has enough structural integrity to maintain its appropriate position and withstand anatomical forces, as well as additional forces such as extension of an integral portion of the device. In particular, a device for fecal incontinence can have an extendable portion that changes from a less extended state to a more extended state, extending posteriorly against the rectovaginal septum. For this extension to be effective in preventing unwanted passage of stool, it can be important for the device to maintain its position and support the extended portion, ensuring it extends posteriorly. Additionally, it can be important for the force of stool against the extended portion (the force being transmitted through the rectovaginal septum) to be resisted by the device in order for the device to be effective at preventing unwanted passage of stool; this is also true for a device with a statically extended portion.

Collapsible intra-vaginal devices to inhibit the passage of stool are disclosed herein. In general, the collapsible intra-vaginal devices can be opened from a collapsed state to a stable open state (e.g., for stabilizing the device after positioning in the vagina) and optionally re-collapsed (e.g., for allowing easier insertion and removal of the device after positioning from the vagina). The intra-vaginal devices described herein include at least one extendable portion that can be extended against the rectovaginal septum to create a protrusion into the rectal space and inhibit the passage of stool. More particularly, the devices disclosed herein generally have a stabilizing body (or stabilizing portion) that maintains position and stability of the device, and an occluding body (or occluding portion) that can protrude into the rectal space. The occluding portion can be similar to the occluding portions described for example in Earlier Applications.

The device can include an integral locking mechanism which has at least two states. In one state, it allows the device to assume a state where it is more rigid than another state in which it is less rigid. In this way, the locking mechanism enables the device to switch between states. The more rigid state is preferred when the device is in an open configuration. Herein, device "rigidity" describes a resistance to gross deformation. In many embodiments, this is particularly resistance to gross out-of-plane deformations of the generally planar structure, and resistance to gross collapse in any direction within the plane of a generally planar structure. The overall device is preferably soft and can accommodate small amounts of deformation that do not upset the overall stability of the device.

The states described above regarding the rigidity of the device and the general nature of the locking mechanism can independently or separately apply to: the device as a whole, the stabilizing portion, the occluding portion, or a combination thereof.

The direction of device expansion when switching from a collapsed state to an open state can be perpendicular to the direction of the extendable portion. In some embodiments, the expansion of the device from a collapsed state to an open state does not involve an expansion of the device in directions that are not perpendicular to the direction of the extendable portion. This near-perpendicular angle allows maximum potential occlusion depth of an extendable portion of a given size. Additionally, configuring the device with the angle of extension near perpendicular reduces the tendency for the device to translate inside the vagina upon expansion.

In some embodiments, the stabilizing portion expands to a width that is greater than the width of the extendable portion. A wider stabilizing portion can provide a more stable configuration of the device when the extendable body is extended. An extendable body of a smaller dimension can allow the extendable body to press into the rectum to an effective depth, while a patient remains comfortable. It was discovered that reducing the width of the extendable body relative to the stabilizing body increased vaginal slack in such a way that allowed for more effective posterior compression of the rectum through the vagina, while maintaining stability.

In some embodiments, the device can allow for collapse, and when collapsing forces (e.g. fingers) are removed, it re-opens or partially re-opens on its own, or is re-openable with the application of external or internal forces (e.g. inflating balloon, spring, engaging a lock). It can re-open to a stable state, or additional inputs can be required to re-stabilize (lock) the device in a stable open state.

Figure 1B:
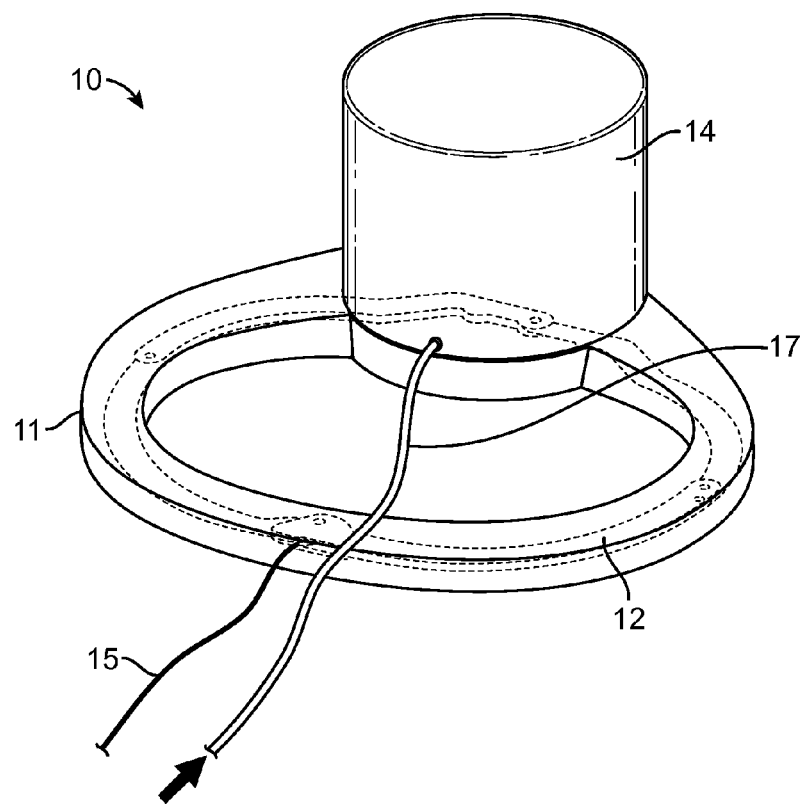
Figure 1C:
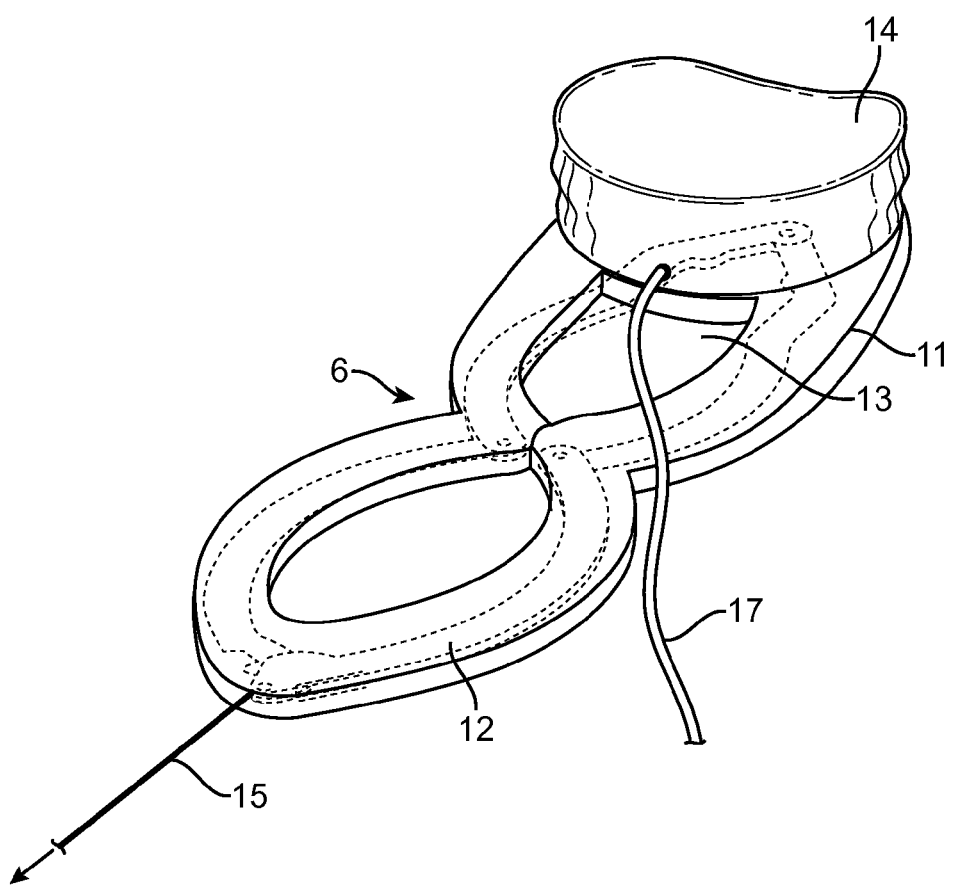

Referring to FIGS. 1A-1C, an intravaginal device 10 for controlling fecal incontinence includes a collapsible stabilizing body 3 with a collapsible frame 12 and an expandable body 14 configured to extend posteriorly against the rectovaginal septum. The frame 12 is formed of multiple rigid segments (e.g., 4 segments, 6 segments, 8 segments, 10 segments) that are joined at their ends by hinges that allow one-degree of freedom of angular motion. In some cases, the rigid segments can be arcuate. Opening and collapsing the rigid segments allows the device to assume a generally round (e.g., oval or circular) open state during use after insertion into the user's vagina and to assume a collapsed state during insertion and removal. The shape (round, oval or circular) of the opened device can be important for safe and effective functioning, providing support at minimal risk to vaginal tissue under repeated extensions of the extendable body. In some cases, the rigid segments are partially arcuate and partially linear in the open state.

Clinical testing revealed a range of pressures internal to the device and applied to the rectovaginal septum that were optimal for occluding the rectum in order to prevent stool leakage, while at the same time not causing discomfort or adverse events such as tissue necrosis. In some embodiments, the expandable body is inflated to a pressure of less than about 200 mmHg. In some embodiments, the expandable body is inflated to a pressure between about 40 mmHg and about 150 mmHg. In another exemplary embodiment, the expandable body is inflated to a pressure between about 60 mmHg and 120 mmHg.

In some embodiments, the expandable body applies a pressure of less than 200 mmHg to the rectovaginal septum in an extended state. In some embodiments, the expandable body applies a pressure between about 40 mmHg and about 150 mmHg to the rectovaginal septum in an extended state. In some embodiments, the expandable body applies a pressure in the range of about 60 mmHg to 120 mmHg to the rectovaginal septum in an extended state.

In some embodiments, the expandable body is located more than 2 cm from the distal end of the device. In some embodiments, the expandable body is located on the proximal half of the stabilizing portion. Through human clinical testing, it was more difficult to obtain intravaginal rectal occlusion with the same posterior force application in the area of the perineal body than in the area proximal to the perineal body. This result was unanticipated because the rectal canal is narrower in the region of the perineal body. Users also felt greater discomfort when force was applied to the perineal body as compared to proximal to the perineal body. Locating the expandable body at least 2 cm from the distal portion of the stabilizing body, and more preferably on the proximal half of the device, configures it to compress proximal to the perineal body.

In some embodiments, the expandable body compresses the rectum greater than about 3 cm proximal to the introitus. This configuration allows the occlusive portion to press proximal to the perineal body.

Figure 1D:
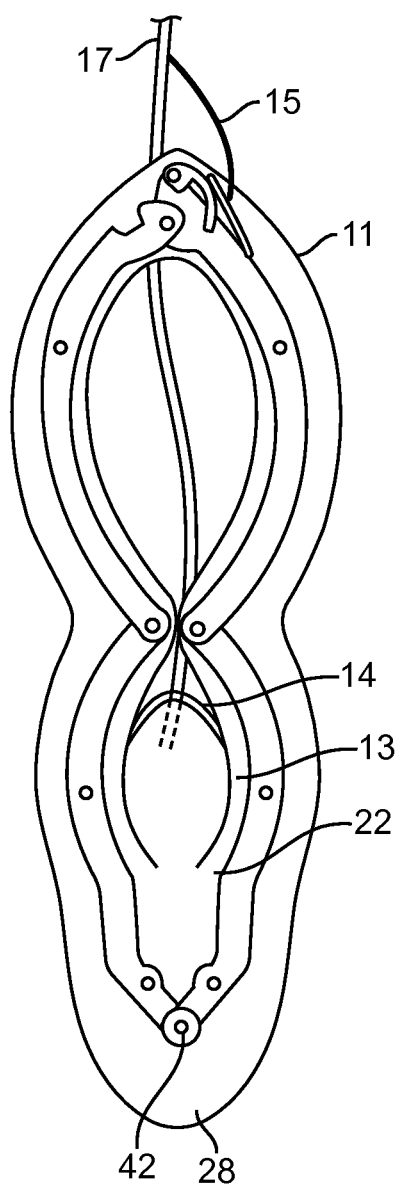
Figure 1E:
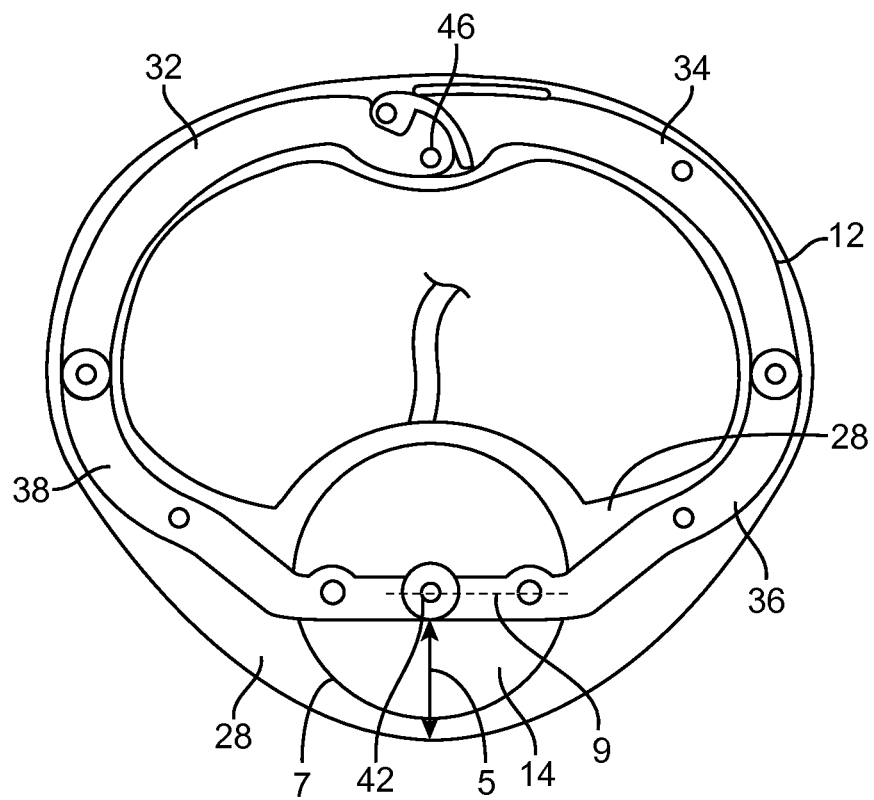

The segments are held in the open state via a locking mechanism 16 that is engaged to secure the device in the open state during use. In general, the expandable body 14 is positioned above one or more segments of the frame, such that it is attached to a location on the stabilizing body where the frame 12 is underneath it. Placing the expandable body 14 above frame 12 can provide one or more of the following advantages: locating the expandable body in the proper anatomical location; providing sufficient support for the expandable body to ensure that it extends posteriorly against the rectovaginal septum rather than extending anteriorly or in another direction; reducing the amount of device components and material within the loop formed by the frame, so that collapsibility for the frame is maximized (e.g., as compared to locating the expandable body and its support largely within the loop formed by the frame such that it is compressed or pushed above or below the frame for collapse); reducing the need for additional structure to support and stabilize the expandable body; locating the balloon on the stabilizing body where the stabilizing body is less wide than another part of the stabilizing body. The stabilizing body 3 is configured for securing the device around the area of the pubic notch and posterior formix and for supporting a force-applying or occluding body 14. FIG. 1A illustrates the expandable body 14 partially deflated, while FIG. 1B illustrates the expandable body 14 inflated, in a force-applying state. FIGS. 1D and 1E illustrate another embodiment of the device 10, wherein the locking mechanism 16 is more visible.

Herein, "Anterior" refers to portions of the device and anatomy closest to the bladder. Additionally, "Posterior" refers to portions of the device and anatomy closest to the rectum.

The expandable body 14 is a force applying or occluding portion. The expandable body can be an inflatable member such as a balloon, though other mechanisms are considered below. It can alternately be referred to as an extendable body or extendable portion.

The inhibition of stool resulting from the application of force is due to the force the device applies to the rectum, which disallows the normal expansion of the rectal lumen, which normally occurs to accommodate stool. This action can be described as applying a force to deflect the recto-vaginal septum to compress the rectum, or as generally preventing the expansion of the rectum by applying a force to it. Alternatively, the force applying portion can reversibly apply a force against the vaginal wall opposite of the recto-vaginal septum, which would prevent stool passage by pressing the stabilizing body, or an additional expandable member, against the rectovaginal septum.

The width of the expandable body can be about 1-6 cm, or about 3-5 cm. The length of the expandable body can be about 1-6 cm, or about 2-5 cm. The main body proximate to the expandable body can be less than about 7 cm and more preferably less than about 5 cm in width to reduce tension in the vaginal walls.

It can be important that the intra-vaginal device 10 not utilize lateral distention of the vagina for fixation when applying pressure to the rectum to occlude stool. Devices with a wider body that take out the slack in the vagina walls, can make it difficult to utilize the recto-vaginal septum to occlude the rectum. Since the device creates significant lateral distension on the adjacent wall, the wall loses its redundancy and elasticity and is not easily manipulated by the expandable portion. The intra-vaginal device 10 can take advantage of the vaginal redundancy to push on the rectum. In other words, sufficient slack is still present in the vagina once the device 10 has been inserted, allowing the vaginal walls to be manipulated such that the rectum is occluded. This configuration allows stability and comfort while providing the function of occluding the rectum.

In the embodiment of FIGS. 1A and 1B, the stabilizing body (comprising the collapsible frame 12 and a soft encasement 11) forms a structural perimeter. This structural perimeter can be rigid in the open state to resist deformation in out-of-plane directions, as well as resist a width-wise or length-wise in-plane collapse. This perimeter, comprising the frame 12 of interconnected segments, is constrained to planar motion by the hinges joining the segments. Such rigidity of the structural perimeter can be provided by the components that form the structural perimeter itself (e.g. interconnected frame 12), as opposed to having support features such as cross-bars or tension elements that span the open space within the perimeter. In some embodiments, this rigidity and resistance of out-of-plane bending can limit the out-of-plane bending to ≤about 30° under a load (e.g. about 1.5 lb) applied to periphery of frame, normal to plane of frame.

In some examples (e.g. FIGS. 1A, 1B, 1E), the expandable body 14 is positioned on the periphery of the round shape formed by the frame 12 at a location that is approximately opposite the locking mechanism 16. This position can allow for the expandable body to be in the proper anatomical position (towards the proximal or deepest, portion of the vagina, towards the rectum), while also allowing the locking feature 16 being in the anatomical location that is most readily accessible from outside the vagina for actuation (towards the distal portion of the vagina, centered at the introitus). Additionally, with the expandable body 14 in this position, there is spatial clearance between it and the locking mechanism 16, such that mechanisms and supports related to the expandable body 14 and the locking mechanism 16 can operate without interference from each other.

To stabilize the expandable body 14, at least a portion of the frame 12 (or some extension thereof) preferably passes below the expandable body or additional support features of the expandable body (additional support features include the cushioning pad that the expandable portion is positioned on). In other words, in the viewing direction as shown in FIG. 1E, the frame 12 passes through the area of the expandable portion 14. In general, the stabilizing body can be positioned with respect to the expandable body so that the stabilizing body is in a position to provide reaction forces to forces generated by or acted on the expandable body.

When the frame is collapsed, as shown in FIGS. 1C and 1D, the device takes the shape of multiple oval segments. "Oval", in reference to the shape of the collapsed device, describes the shapes as seen in FIG. 1D, which have a convex exterior profile on either lateral side, and a longer (longitudinally, along the proximal distal axis) than they are wide (laterally). Referring to FIG. 1C, in this collapsed state, the width of the frame 12 midpoint 6 of the lateral arms is narrower than the width spanned by the portions proximal and distal to the midpoint. Collapsing in this manner, the widest (laterally) portion of the frame in the open configuration become the narrowest portion (aside from either end where the device terminates in a point) of the collapsed configuration. Space 13 can be left between the collapsed segments of the frame that can advantageously accommodate portions of the extendable portion and its support. This space 13 can allow for more compact collapsing of the device 10. Additionally, the curved profile of the collapsed device can provide approximately oval formations that provide preferred gripping features for the manipulation of the device for insertion and removal. In a preferred embodiment, the approximate lengthwise midpoint 6 (FIG. 1C) of the collapsed structure is the narrowest portion of the collapsed device. This point is also the location where the most leverage is possible for compressing/collapsing the device (meaning the least amount of force is required to fully collapse when manipulated at this point). This can serve the advantageous purposes of: allowing a contoured grip at an optimal gripping and compressing location; allowing the wider proximal end of the device to be first inserted past the (typically) narrowest portion of the vaginal lumen (the introitus). Then, if there is a pause in insertion and a release of the collapsing force (e.g. a change of finger gripping positioning in the case of a manual insertion), the device is at least temporarily stable. The introitus would have to further widen to pass either the proximal or distal segment, and at this point there will be the least amount of force transferred to the introitus due to the maximal leverage on the frame at this point. It is noted that the introitus is the portion of the vagina that is particularly sensitive to distention. As a result, this collapsed configuration which includes multiple arcuate portions provides a more comfortable insertion.

A removal feature 15 is operably connected to the locking mechanism such that when the removal feature is actuated (in the current example, by applying tension), the lock is released and the device is able to be collapsed for removal or insertion. Collapsing the device in the unlocked state can be done by pulling the hinge opposing the locking mechanism and the hinge comprising the locking mechanism away from one another. For example, the locking mechanism can be unlocked by pulling on the hinge comprising the locking mechanism 16 in a direction away from the posterior end 4 of the device 10. With the device unlocked, the device can be collapsed in the unlocked state by pressing the lateral sides together. For example pressing together the lateral midpoint 6 (FIG. 1C) towards the same point on the opposite side of the device. The removal feature 15 can comprise a tensile element (e.g., a cord, cable, string, wire, etc.). This removal feature 15 preferably resides outside of the vagina to facilitate removal (e.g. by pulling on a cord). In some examples, the expandable body 14 is an inflatable balloon with an inflation tube 17 extending outside of the vagina. This inflation tube can be coupled to the removal mechanism 15. In some embodiments, the tube itself, or a reinforced section of it, can be tensioned to release the lock (see, for example, FIG. 45 and its description).

The stabilizing body frame can be encased in a soft material 11, (e.g. silicone) to protect the vaginal tissue against the rigid portions of the device. There can preferably be additional soft material disposed 22 (FIG. 1A), 28 (FIG. 1E) in the proximal portion of the device, proximate to the expandable body 14. Additional protective material (described in more detail below) in this area can help protect against force concentrations due to the presence of or extension of the expandable body, as well as protect against the proximal most leading edge of the collapsed frame during insertion. This soft material can be flexible to accommodate the shape changes of the frame. In some embodiments, no protective material is used, for example, if the shape of the collapsed device presents no sharp edges and the contours of the perimeter of the opened and collapsed device are without corners. In some embodiments, the device comprises multiple rigid segments. There can be some amount of flexibility to the rigid segments, but when deployed, they can provide enough rigidity to support the device's function. These segments are joined by more flexible or disjointed portions in a number of possible ways. For example, multiple "segments" can comprise one continuous piece of material, where the more rigid segments are separated by more flexible portions that allow some degree of folding between the rigid segments. Alternately, the rigid segments can be joined by a joint that allows relative motion between the rigid segments. This joint can be, for example, a hinge, a ball-in-socket joint, a living hinge (of the same, or dissimilar material as the rigid segment), a connecting segment of more flexible material, or any other means of joining two or more rigid segments in a manner that allows some degree of relative motion between the rigid segments. The device can comprise similar joints between rigid segments, or different joints between rigid segments. In a preferred embodiment, these joints are configured to constrain the relative motion to one-degree of freedom (e.g. one angular dimension). In the example of the living hinge, this can be accomplished by the geometry of the living hinge portion being a band that is wider in the direction normal to the plane of bending than in a direction parallel to the plane of bending, thus making it easy flex in the plane of bending, and more difficult to flex in other planes.

Exemplary materials for the rigid segments include, but are not limited to, stainless steel, polycarbonate, glass-filled polycarbonate, peek, acrylic, and delrin.

In some embodiments, as shown in FIGS. 2A-2D, a stabilizing body frame 14 for the device is formed of 4 curved (e.g., arcuate) or partially curved rigid segments 32, 34, 36, and 38, joined at their ends by hinges that allow one-degree of freedom of angular (e.g., rotational) motion (e.g., hinges 40, 42, 44, 46). In order to prevent twisting or out-of-plane motion between segments, the segments have flat faces at the hinges (e.g. the opposing surfaces of each hinge is planar) and are preferably constrained to have space between them that is less than about ⅛-½ the diameter of the axle, such that the hinges are more securely constrained to prevent twisting or out-of-plane motion between segments. The segments are arranged such that when they are all connected end-to-end, they form a planar loop.

The use of curved segments (e.g. 32, 34, 38, and 36) has the additional advantage of allowing for the device to form a loop with a rounded exterior profile and a predominantly open center. Fewer than 4 curved segments can be used as well, including for example using only two curved segments on the distal half of the device. Open space is advantageous for allowing movement of vaginal fluids. Minimizing the amount of volume occupied by the device is also advantageous for vaginal health; both are improved by the use of curved members to support the structural perimeter of the device by providing a rounded external profile and minimizing the material within the structural perimeter The frame components (e.g. 32, 34, 36, 38), as well as the protective soft covering 11 (FIGS. 1A-1E), form a smooth outer profile, without corners or sharp bends. The perimeter of the device, as well as the outer perimeter of the frame, when viewed in the anterior-posterior direction, as shown in, for example, FIG. 1E has no arcs ≥about 20 mm in length with radii of curvature less than about 12 mm; or no arcs ≥about 10 mm in length with radii of curvature less than about 5 mm; or no arcs ≥about 5 mm in length with radii of curvature less than about 3 mm. In another example, in the open configuration, at each hinge, an angle drawn to a points on the midlines of the adjacent frame segments at a distance of about 18 mm from the hinge forms an angle with the hinge ≥about 100 but ≤about 180 degrees; or the angle formed by points on adjacent segment's midlines at a distance of about 14 mm from their mutual hinge is ≥about 95 but ≤about 195 degrees; more preferably the angle formed by points on adjacent segment's midlines at a distance of 10 mm from their mutual hinge is >about 90 but ≤about 210 degrees. In another example, both the limits described above on the radii of curvature and angles at the hinges must be true. In some embodiments, the device has no sharp or angled features, and includes tangencies or approximate tangencies at all locations of flexure such as the locations of the joints.

Figure 2A:
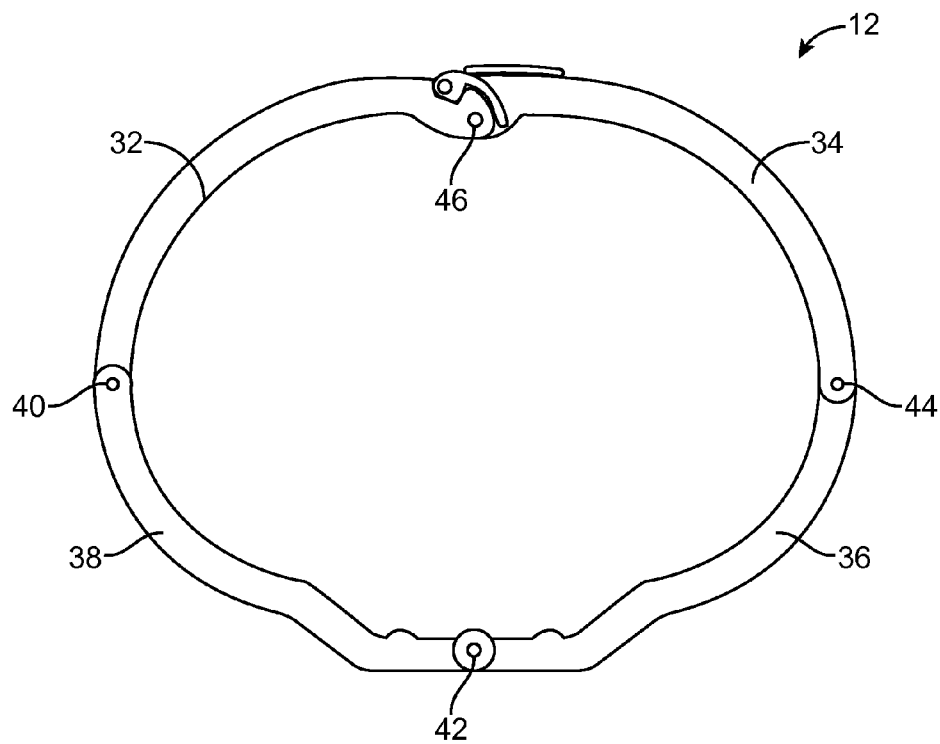
FIGS. 2A-H illustrate an embodiment of a device frame and a locking mechanism.
Figure 2B:
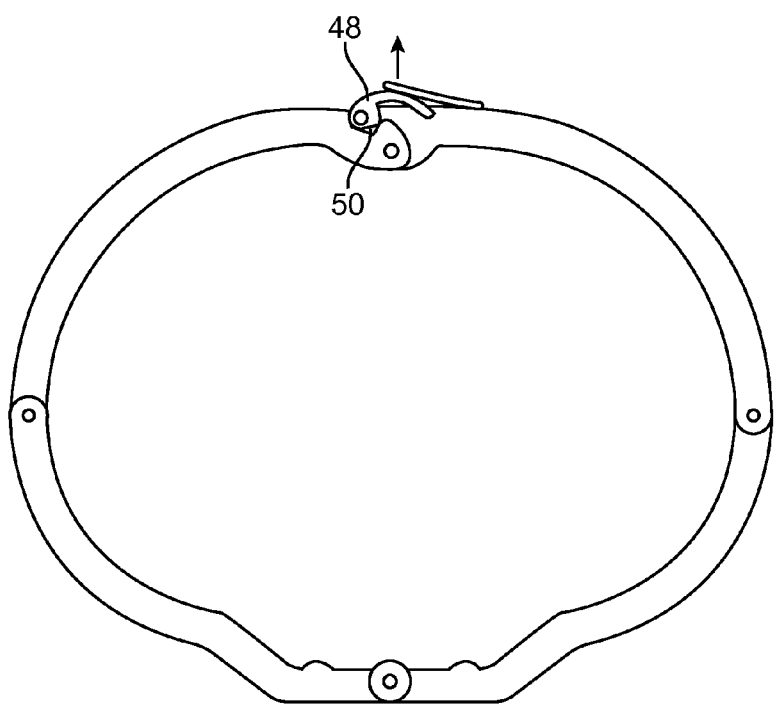
Figure 2C:
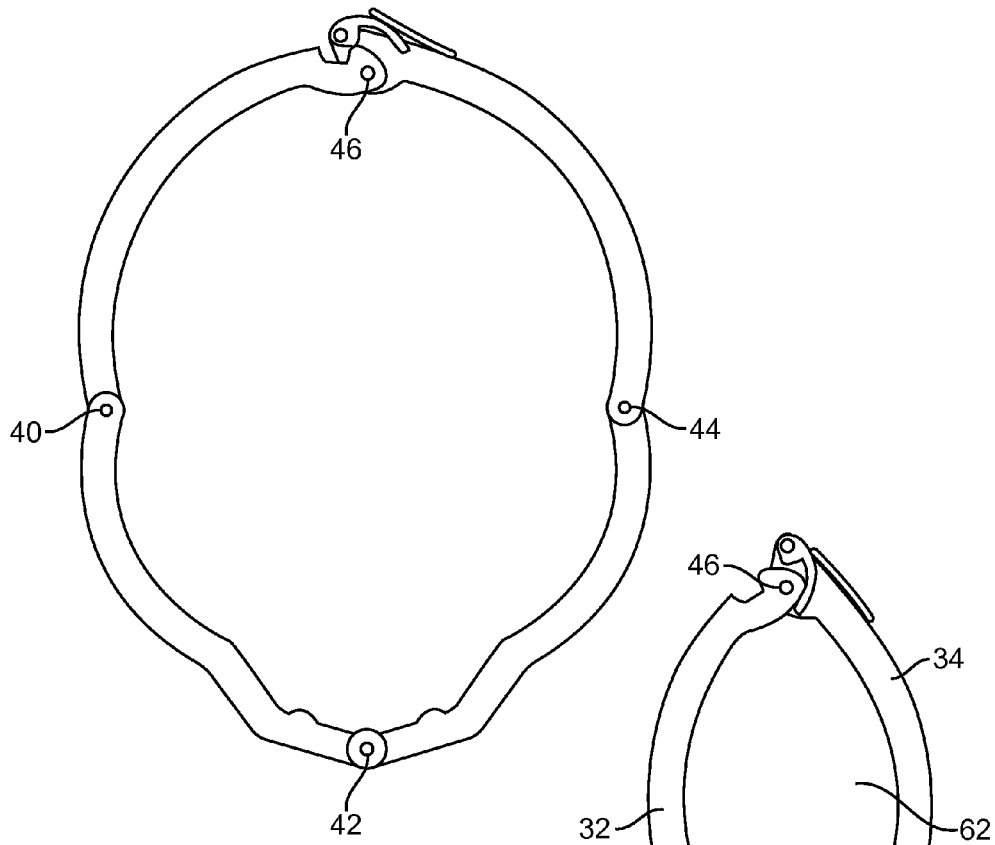
Figure 2D:
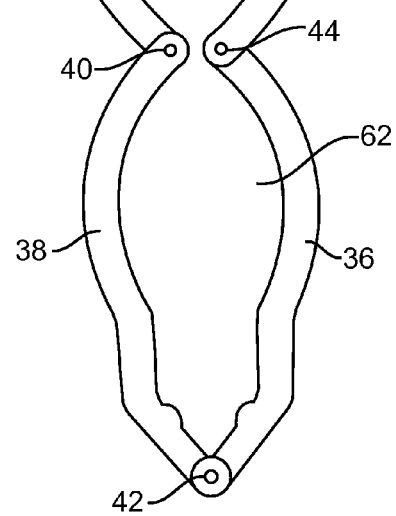
Figure 2E:
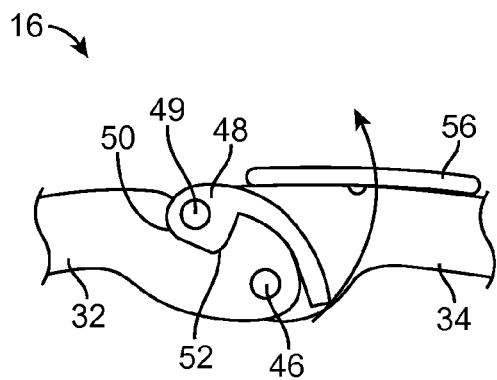
Figure 2F:
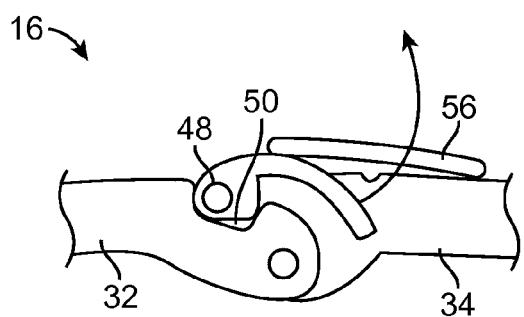
Figure 2G:
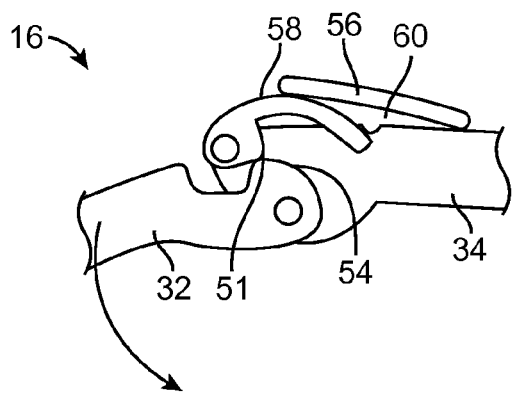

In some embodiments, with all 4 hinges joined, the assembly can take a variety of shapes including an open shape (e.g. as shown in FIG. 2A), or a collapsed shape, (e.g. as shown in FIG. 2D). FIGS. 2A-2D, illustrate an embodiment of a frame 12 being collapsed. FIGS. 2E-2G illustrate an embodiment of the locking mechanism 16 in detail being unlocked as the frame is collapsing. In the collapsed shape, two opposing hinges (e.g., hinges 40,44) approach each other, as shown in FIGS. 2C and 2D, which show the frame collapsing. Hinge 42 can be referred to as the proximal hinge. The proximal hinge 42, in-situ, rests near the cervix or vaginal cuff of a patient. The opposite hinge 46 is referred to as the distal hinge. The distal hinge 46 rests near the introitus. The other hinges 40, 44 are referred to as lateral hinges. The device 10 is configured to collapse via a "lengthwise collapse" wherein, during the collapse of the device the proximal and distal hinges 42, 46 move away from each other (e.g., the distance between the proximal and distal hinges 42, 46 is greater in the collapsed position than in the open position), and the lateral hinges 40, 44 move towards each other (e.g., the distance between the lateral hinges 40, 44 is smaller in the collapsed position than in the open position). Considering overall widths and lengths of the device, during the collapse of the device, the length increases and the width decreases. In some embodiments, the height of the device does not change during the collapsing or opening of the device.

Figure 3A:
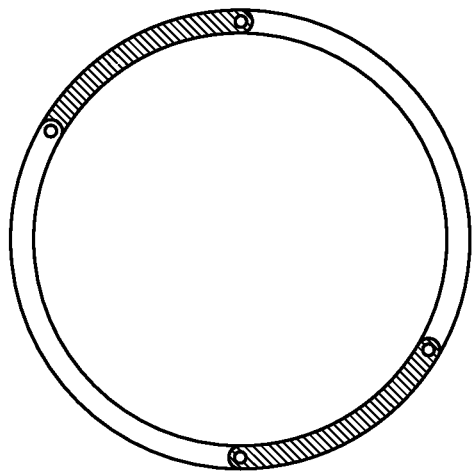
FIGS. 3A-D illustrate an embodiment of a device frame.
Figure 3B:
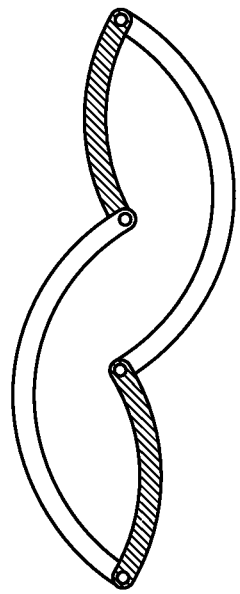
Figure 3C:
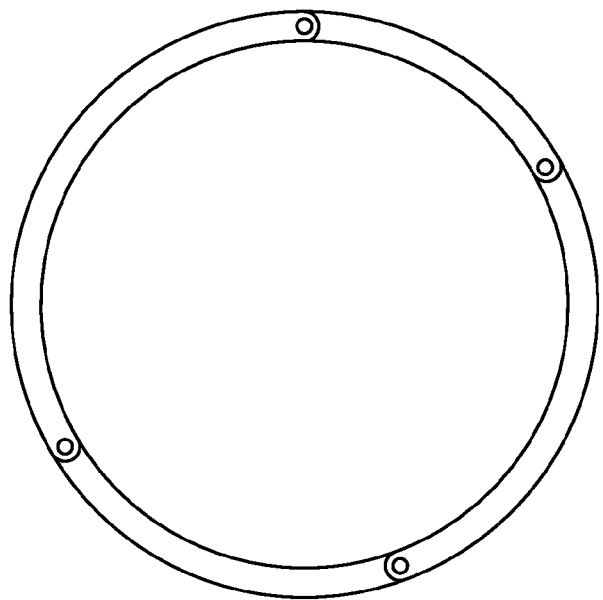
Figure 3D:
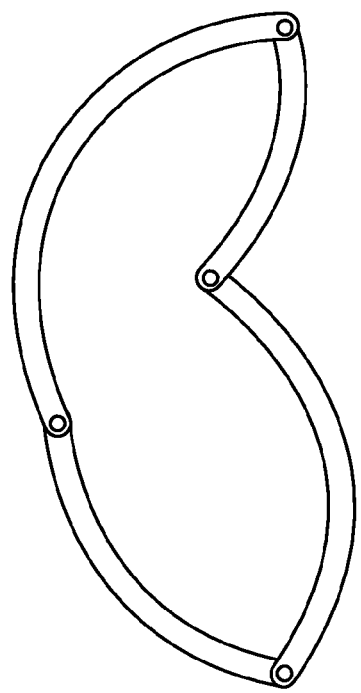

As described above, and as shown in FIGS. 2A-2D, the hinge pattern is symmetric about an axis (a line drawn from hinge 46 through hinge 42). However, other configurations are possible as well. For example, FIGS. 3A and 3B illustrate an embodiment of a hinge pattern that is symmetric about a point or rotationally. FIGS. 3C and 3D illustrate another embodiment of a hinge pattern that is symmetric about a point or rotationally. These configurations can be more compact widthwise than symmetrical ones in the collapsed configuration or offer different leverages for control of the device during insertion and removal.

Figure 2H:
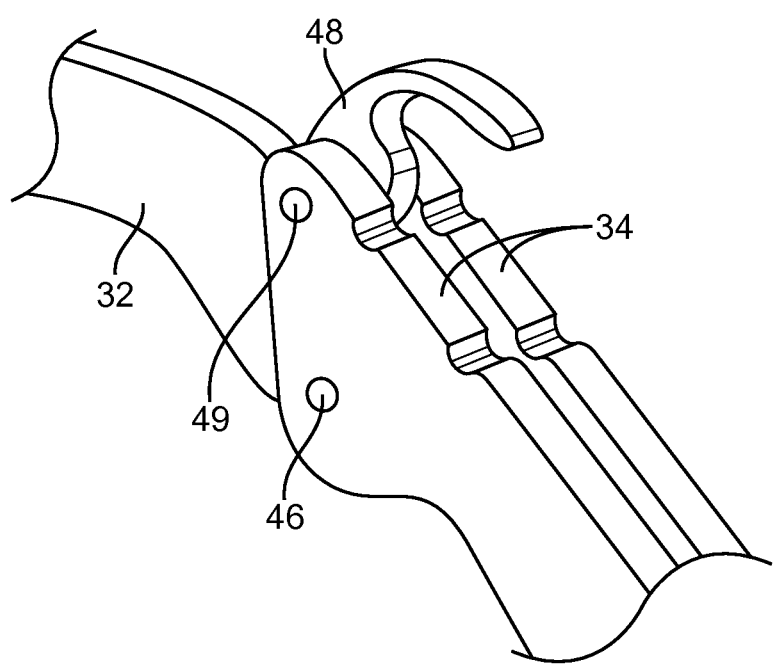

FIGS. 2E-2H shows an exemplary locking mechanism. The collapsible frame of a preferred embodiment locks when a latch 48 that is attached to one frame segment 34 drops into a pocket 50 on another frame segment 32. When lateral force is applied to the device, the latch prevents the segment 32 with the pocket 50 from rotating with respect to the other segment 34, preventing collapse. When the latch is rotated out of the pocket, segment 32 is allowed to rotate with respect to segment 34, and therefore the device can collapse. The pocket and latch are constrained to interact by being maintained in the same plane, in this example by being sandwiched between other segments of the frame and by their pivot points being a fixed maximum distance from one another. FIG. 2H illustrates the latch 48 and pocket being sandwiched in between portions of segment 34. As segment 32 rotates about hinge 46, the face 52 of its pocket 50 that faces the latch presses against the latch face, transmitting a force to the hinge 49 of the latch. The latch-facing surface of the pocket and the pocket-facing surface of the latch have curved faces 52 that are concentric with each other and with the pivot point 49 of the latch 48 so that as the latch is moved, its advantage relative to the pocket does not change until a point 51 is reached, where the radius of the latch's face decreases and the segment with the pocket can slide past the latch, allowing segment 32 to rotate, and therefore allowing the device to collapse. In other words, one advantage of the concentric faces is that the latch rotates free of interference from the pocket (other than friction at the surface). If the faces of the latch and the pocket are not concentric with the latch's pivot point, the lock can become unstable. For example, if the curvature or angle of the pocket's face is shallower than the curvature or angle of the latch's face, when segment 32 rotates, the pocket 50 can push latch 48 up and out of the way, unlocking the lock. Alternately, if the pocket has an overhang with respect to the latch, the pocket face will have to be moved away from the latch to allow the latch to be clear to rotate out of the pocket; and since moving the pocket in this fashion requires clockwise rotation of 32, and rotation in this direction causes the overall device structure to become laterally wider, disengaging the lock when there is an overhang over the latch will therefore be difficult if there is any force resisting a widening of the device. Such a force could be anything pushing laterally inwards on the device (e.g., the vaginal walls pressing against the device). This is a particularly important factor for a vaginal device as there could be a lateral load applied to the device by the vaginal walls when it is wished to be removed.

In the latch embodiment shown in FIG. 2E-2G, the segment 32 with the pocket 50 has a curved region 54 that remains engaged with the latch in the collapsed state so that upon opening of the device, the latch 48 presses against the curved region as 32 rotates until the pocket 50 becomes aligned with the latch, and the latch drops in. A member (in this case spring 56) is used to provide the force for dropping the latch into the pocket. The tail of the latch 48 that the spring pushes on is curved so that the latch can move smoothly relative to the spring during collapse and opening of the device. The latch tail 61 comprises an element such as a pull cord attached. The length of the tail 61 increases the advantage of the user against the friction of the mated surfaces. When pulled, the latch rotates until the tail reaches a hard stop 60, transferring further force directly to the device frame, facilitating removal.

As described above, a force applied to the device in a way that can cause the device to collapse will transmit force to the locking mechanism or mechanisms. In the example provided above (FIG. 2E-2G), this results in friction between the mated surfaces at 52. This force or pressure transmitted to the locking mechanism 16 can make it more difficult to actuate. This is true of many lock designs. As described above, the concentric faces at 52 minimize this effect. The effect of a collapsing force on a locking mechanism can also be referred to as binding. Another means of reducing the binding in a locking element is to provide for some springiness in at least one of the locking segments (e.g. segments 32 or 34). For example if either (or both) of 32 and 34 had some flexibility, they could flex when pressed on by for example the vaginal walls or fingers, transmitting less force to the lock and resulting in less binding.

Alternately to the use of a spring, the material surrounding the collapsible frame (especially when an elastomeric material) can push the latch back into position. Any number of configurations of spring elements can be used to return the latch to the mated position. The location of the lock and lockable hinge 46 can be offset to one side such that if a tensile element is used to rotate the latch, it is approximately centered to the device.

In general, a locking mechanism similar to the example described above operates by preventing rotation of at least one segment of a hinge in at least one direction. This can be accomplished by a number of means involving a removable obstruction to the motion of at least one segment. Typically the feature that causes the obstruction is affixed to the opposite segment, but it can also be affixed to a different portion of the device or a third member. Additional locking mechanism examples are described below.

In some embodiments, when the device is not in the locked open state, the device (absent external forces) can naturally be in a state that is almost locked, such that only a small amount of force or displacement causes the device to be locked. In this way, it is not difficult to lock the device once it is inserted into the vagina. For example, as described in more detail above, the mechanism shown in FIGS. 2A-2G locks when latch 48 drops into pocket 50. When segments 32 and 34 rotate from a collapsed configuration to the open configuration, a point is passed where latch 48 is able to drop into pocket 50; the frame is then locked. Therefore, the overall configuration of the stabilizing body can be such that, at rest, the latch 48 is very close to the pocket 50, such that a small amount of further opening causes it to latch. Alternately, the stabilizing body can be biased such that there are spring forces (e.g. provided by the encasement material, expandable portion, expandable portion support, springs, or resiliency of segment joints) that tend to more fully collapse the stabilizing body. In this way, these forces are overcome to open and lock the stabilizing body. Alternately, the stabilizing body can be biased to fully open to or past the point of locking, such that (absent other interfering forces) when collapsing forces are released, the stabilizing portion opens and locks. In this way, these spring forces are overcome to collapse the device. It can be preferable to have the device configured such that minimal force is required to change the state of the device from fully locked to open to collapsed.

Preferably, the protective covering is flexible enough to accommodate the motion of mechanisms involved in lock and unlocking a joint or joints. Additionally, space can be provided between the mechanism and the protective encasement to further allow movement of these mechanisms.

In another embodiment, no latching mechanism is necessarily used to secure the device in a given position. Instead, spring force can be used to cause the device to be biased towards a given shape. In this configuration, there is still an advantage to having the shape change in a constrained manner as described above (e.g. utilizing segments with constrained hinges). As described herein, the constrained, generally planar motion of the shape change is easier to handle. Additionally, the advantages described above regarding structural integrity (resistance to out-of-plane folding) and expandable body support apply to this configuration as well. An additional advantage of this design is that it can self-adjust to a particular length or width to fit a patient's anatomy because it opens under spring force until it meets external resistance (or maxes out its springs); in this way it can expand until it presses hard enough against the vaginal walls for the spring force to be balanced. Furthermore, if a force directed along the proximal-distal axis (such as pressure from the proximal vagina) causes the proximal hinge (FIG. 2A, 42) to move towards the distal hinge (FIG. 2A 46), the kinematics of the 4 bar linkage will cause the device to become wider, reducing the potential for the device to slip out of the vagina. This is possible for other numbers of linkages as well.

The above descriptions (e.g. descriptions of the device of FIGS. 1A-1E, 2A-2G) are not meant to exclude other number of joints or configurations of joints wherein one or more joints allow for greater than one degree of freedom. For example, a single joint with multiple degrees of freedom (e.g., a ball and socket joint) will still allow for the full assembly to maintain planar constraint, especially if the remaining joints have only one degree of freedom (preferably rotational). Two adjacent joints can also have multiple degrees of freedom, which can allow the segment spanning them to move (e.g., rotate) relative to the rest of the frame. If the rest of the frame is constrained, the overall stability can be maintained. However, it can be advantageous to limit the amount of play and relative motion of the stabilizing frame to enable a secure positioning of the expandable body against the rectovaginal septum such that the expandable body and the device as a whole can resist a loss of position based on forces from the anatomy and stool passage. One way of doing this is to have at least 3 hinges constrained to a single degree of freedom; preferably rotational. One or more joints between segments of the frame can be formed not by a rigid hinge, but by encasing two adjacent segment ends in an elastomeric material or bonding them to an elastomeric material.

In the collapsed position, the curvature of the segments (e.g., segments 32, 34, 36, 38) forms a non-linear collapsed frame. More particularly, in the collapsed position (as shown in FIG. 2D), the frame forms multiple approximately round or oval shaped segments 62. Collapsing into a set of round or oval shaped segments is believed to provide the advantage of providing space between opposing sides of the device in which portions of the device related to the extendable portion (e.g. padding, balloon, tubing connections, supports) can reside in the collapsed configuration. FIG. 1D shows expandable body 14 and cushioning member 22 inside of space 13. This orientation can allow for a more compact collapsed form, with less interference to folding from the extendable portion. Additionally, it can allow these other components of the device to be situated in the same plane as the rigid segments, instead of above or below their plane, such that the overall height of the device is not increased, either in the opened or collapsed state. Additionally, the oval or round segments can provide gripping structure for the user that allows for better control, particularly for controlling against rotation (e.g. with a wider structure to grasp, the collapsed device is less likely to slip, in a rotating fashion).

Figure 4:
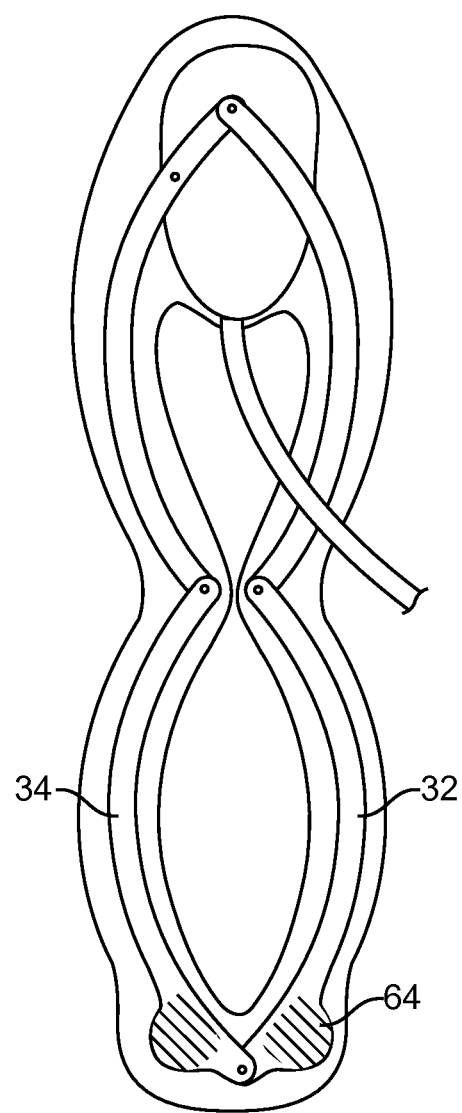
FIG. 4 illustrates an embodiment of a collapsible intra-vaginal device.

More generally, in the collapsed configuration, there can be space between the approximate midpoints of opposing proximal segments (e.g., segments 32 and 34, FIG. 2D) and/or distal segments (e.g., segments 36 and 38, FIG. 2D) that can accommodate other features of the device during collapse. In some embodiments, this space can be less than ½ and at least about 1/15 the nominal external lateral width of the open configuration during use; or, this space is about 1/10 the nominal external width of the open configuration during use; or, this space is at least about ⅛ the nominal external width of the open configuration during use. In some embodiments, this space is less than about 25 mm and at least about 6.5 mm; or, this space is at least about 6 mm; or, this space is at least about 5 mm. On the distal end, open space extends to at least about 6.5 mm (or about 6 mm; or about 5.5 mm; or about 4.5 mm) distal of the widest portion. The distal space can allows a fingerhold for control during insertion and since it is distal to the widest portion, allows the widest portion to be inserted into the vagina before the user wishes to change grip. During removal, this fingerhold can be close enough to the vaginal opening to be accessed, and can be used to pull on the device. As shown in FIG. 2D, the distal portion (formed by segments 32 and 34) of the collapsed configuration forms a tapered tip of about 10-135° (or about 20-90°); said angle continuing for a distance of at least about 0.5" from the distal tip. In some embodiments, the tapered tip can form an angle of about 10-35°. The taper can allow the user to squeeze and push the device at the same time. The distal portion of the collapsed device (formed by segments 32 and 34), when including the soft material that covers the frame, can be at least about 2×-3× as wide, laterally, as the height (in an anterior-posterior direction). This width can provide structure to grasp, making the collapsed device less likely to slip in a rotating fashion while being held. This structure can be important as correct orientation of the device in the vagina is important for correct use, and in the process of inserting vaginal devices, especially with the use of lubrication, can cause the device to rotate or flip. The collapsed configuration is narrower at its approximate midpoint, where the two lateral hinges 40, 44 of the frame are positioned. The external width of the device at this midpoint is about 6 mm narrower than the wider portions proximal and distal to it, providing a location for a firm grip if the device becomes slippery during insertion, as is often the case when lubrication is used. In another embodiment of the device, shown in FIG. 4, a feature or features 64 extend at least 2-5 mm from the frame, and are located about 0-10 mm along the length of segments 32 and 34 from their mutual connecting point. These features 64 can further enhance grip on the tapered portion of the collapsed device. These features can be extensions of segments 32 and 34 themselves, being comprised of the same rigid material and being of the same solid part. Alternately, they can be part of the soft outer material (e.g. silicone).

Referring back to the examples shown in FIGS. 2A-2G, on one hinge (e.g., hinge 46), there is a mechanism 16 for locking that hinge 46 such that the angle between lines drawn from it to its two adjacent hinges is fixed, or at least fixed in one angular direction. In a preferred embodiment, the lock 16 is on the distal hinge 46 and is configured such that, when locked, the lateral hinges 40, 44 are not able to move towards each other, and thus the angle formed by the distal hinge (defined as the angle, facing the proximal hinge, formed by the lines drawn from the distal hinge to its two adjacent hinges) cannot become smaller. In another embodiment the lock on hinge 46 also prevents the lateral hinges 40, 44 from moving away from each other. This is in part due to the resilience of the segments 32, 34. If segments 32, 34 are somewhat flexible, some motion of hinges 40, 44 is possible, even with hinge 46 locked. Some amount of motion of these hinges can be preferable in certain situations when an overall lateral or proximal-distal flexibility is desired. In this case, these segments (or at least one of them) alone or in conjunction with one or more of the distal segments can be somewhat flexible.

Referring to the examples of FIGS. 1A-1E, the rigid segments are generally shaped to follow the contour of the edge of the full device including any soft covering material (e.g., soft material 11). However, as shown in FIG. 1E, in the open shape, the rigid segments 36, 38 that form the proximal hinge can depart from the external profile of the device, turning more inward to form a generally straight portion that is positioned beneath the extendable device. More particularly, segments 36, 38 include a curved portion and a straight portion. This departure from the external profile of the device can allow for a greater distance between the proximal hinge 42 and the exterior surface of the device and for more soft material between the rigid proximal hinge 42 components and the vaginal tissue near or at the cervix or vaginal vault. For example, the soft material surrounding segments 32, 34, and the curved portions of segments 36, 38 can extend about 0.5-10 mm from the frame while the soft material surrounding the generally straight portion of segments 36, 38 near hinge 42 can extend about 3-20 mm from the frame. In another example, the thickness (shown by arrow 5 in FIG. 1E) between the edge of the frame and the edge of the soft material proximal to the proximal hinge is at least about the same as the thickness of the soft material surrounding the segments on the distal side of the device; or at least about 1.5 times greater; or at least about 2.5 times greater; or at least about 4 times greater. Additionally, this configuration can allow for the thickness of the soft material proximal to the proximal hinge to be approximately as thick as the thickness of the soft material anterior to the proximal hinge; or more preferably, about ≥1.5 times the thickness; or more preferably, about ≥2 times the thickness. Providing extra room for soft material is especially advantageous considering that when the device is folded, the angle formed by the proximal hinge 42 becomes more acute which can create a point, directed posteriorly (as shown in FIG. 1D), and the added soft material helps protect the vaginal walls from this point. This configuration of the proximal hinge 42 can also better align the support structure of the rigid segments with the expandable body to secure the expandable body in the proper position.

Figure 7A:
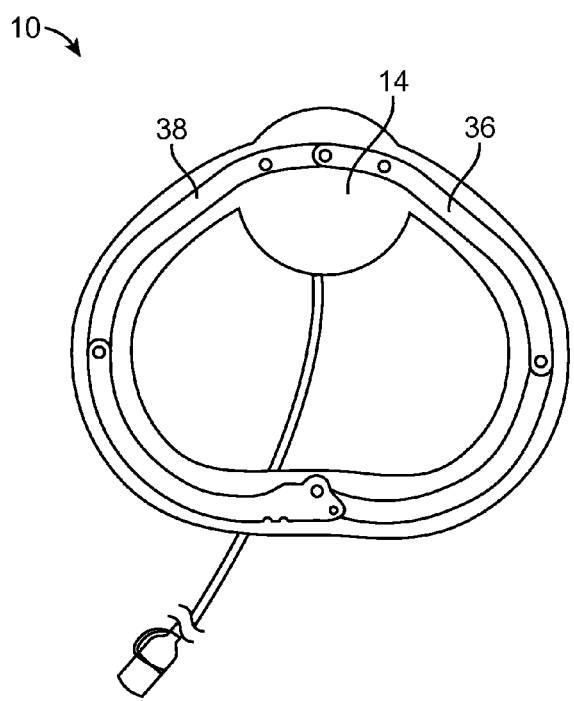
FIGS. 7A-B illustrate an embodiment of a collapsible intra-vaginal device.
Figure 7B:
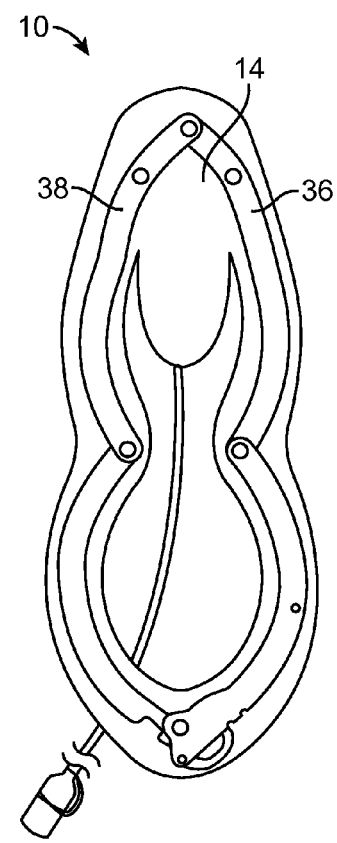

The straight (e.g. linear) portion of the segments 36, 38 (FIG. 1E) that form the proximal hinge, as described above need not be perfectly straight. The segments 36, 38 can be curved or angled. The segments 36, 38 can, in some way, deviate away from the outer edge of the device's protective encasement or any cushioning material that forms the external perimeter of the device, in this way providing for a greater amount of cushioning material and/or deviating to support the expandable body in the proper location with respect to the exterior dimensions of the overall device. However, depending on the desired shape of the device perimeter, the segments 36, 38 can also be rounded as shown in FIGS. 7A and 7B, which show an embodiment of the device 10 in an open configuration and a collapsed configuration, respectively. In this embodiment, there is a continuous tangency along the edge of segments 36 and 38, without deviations from a smooth curve. Placement of this support for the expandable body 14 can be biased proximally or distally to the geometric center of the expandable body 14. As shown in FIGS. 7A and 7B, the support is biased proximally, providing less support to the distal extent of the expandable body.

In some embodiments such as in the examples of FIGS. 1A-1E, there is a broad lateral support for the extendable portion provided by the stabilizing body. In a particular embodiment, the path of the frame segments 38, 36 that support the expandable body 14 provides support for the expandable body against the expandable body tilting or moving laterally. In other words, if a lateral force is applied at some distance along the extension direction of the expandable body, the force would cause the expandable body to deviate in a translating or angular (tilting) fashion; preferably, the frame segments stabilize the expandable body against this deviation. In general, broad lateral support for the expandable body can help to stabilize the expandable body in the appropriate position in the vagina, ensure that the expandable body extends in an appropriate direction (posteriorly, and generally perpendicular to the plane of the stabilizing body), and stabilize the expandable body against forces encountered during use including the force of stool pressing against the protrusion in the rectum created by the expandable body, resistance in the vaginal walls to the extension of the expandable body and other internal body forces such as coughing or sneezing.

For example, FIG. 1E shows the frame segments 36, 38 spanning the width of the expandable body 14, crossing the expandable body at approximately its widest lateral span. Thus, a solid supporting structure of the frame extends across and underneath the entire expandable body 14 at the location where the expandable body 14 is the widest. For example, if the expandable body comprises a substantially circular cross-sectional shape, the expandable body can be disposed such that the frame is located underneath a line that bisects the circular shape into two semi-circular shapes. In another example, if the expandable body is substantially elliptical in cross-sectional shape (with the major axis arranged laterally), the expandable body can be disposed such that the frame is located underneath the major axis of the ellipse. If the expandable body is substantially rectangular in shape, the expandable body can be disposed such that the frame is located underneath a line that bisects the rectangle into two approximately equally shaped rectangles. In general, if a point were made in the plane of the device as viewed in FIG. 1E (e.g. showing a view from anterior to posterior), and that point represented the location of the center of mass of the expandable body, the frame can pass through this point, moving relatively linearly from one lateral side to the other. In this way, the frame can provide optimal leverage against lateral tilt. In some embodiments, the frame segments cross the outline of the expandable body (the outline of the expandable body as it is attached to the stabilizing body; for example: circle 7 in FIG. 1E) near the midsection of the outline. The frame can enter this outline at an angle≤45° with the lateral axis; the frame can enter this region at an angle≤20'; the frame can enter this region at an angle close to 0°. The location of this angle is shown at 9 in FIG. 1E; the angle at 9 is 0°. Some embodiments comprise frame segments that traverse the region of the expandable body near the midsection of intersection of the expandable body (or any supporting feature of the expandable body) and the plane of the frame. In some embodiments, the frame, on average, traverses this region at an angle≤about 45° with the lateral axis; or, the frame, on average, traverses this region at an angle≤about 20°; or, the frame, on average, traverses this region at an angle close to 0°.

There can be an advantage to attaching the expandable body to two adjacent segments of the stabilizing body. In some examples, such as that shown in FIG. 1E, this places the hinge 42 underneath the expandable body. In the embodiment shown in FIGS. 1A-1E, the expandable body 14 is connected via the encasement material 11 and soft portions 28, 22 to two segments 36 and 38 of the stabilizing body. The portions of segments 36 and 38 furthest from their mutual hinge 42 travel the greatest distance during collapsing and opening. Therefore, it can be advantageous for the attachment between the expandable body and these segments to occur as close to their mutual hinge as possible, so that there is less requirement for the expandable body, or its support (e.g. encasement material 11 and soft material 22 and 28), to have to accommodate the travel distance of the segments. In other words, keeping the expandable body and its support close to the hinge limit the amount that they have to be squeezed or stretched to accommodate the opening and closing of the frame 12. It can also be advantageous for the width of the attachment of the expandable portion to be less than the maximum lateral width of the stabilizing portion. The importance of this geometric constraint is explained in Earlier Applications, as well as described herein.

While in the example described above, the expandable body is disposed over a hinge, in some examples the expandable body is not disposed over a hinge. For example, FIGS. 8A and 8B illustrate an embodiment wherein the expandable body is not over a hinge, but is instead located over a rigid segment. In this embodiment, the device would have to be rotated once inserted and at least partially opened. Similarly, for removal, a pull cord 66 can be used to re-orient the collapsed device such that the smallest dimension is perpendicular to the proximal-distal axis of the vagina. The pull cord can optionally interact with a locking mechanism to disengage the lock.

Referring again to FIGS. 1A-1E and 2A-2G, the four rigid segments 32, 34, 36, 38 joined by four constrained joints 40, 42, 44, 46 as described above, when locked (fixed), can provide the structural integrity necessary to carry out the function of extending an occluding body against the rectovaginal septum, such that the septum protrudes sufficiently into the rectal space to impede unwanted stool passage. It is important for the device to have enough structural integrity to ensure the extension is directed posteriorly, rather than the extension pushing the whole device anteriorly. As described in Earlier Applications, this is enabled by the interconnected frame engaging a broader area of vaginal tissue on the anterior side of the vagina. As the expandable body extends it creates a force that is directed equally and oppositely against both the posterior vaginal wall and the stabilizing body. Because the stabilizing body is wider (laterally), and longer (proximal-distally), it encompasses a much larger area of tissue within its perimeter. Therefore, when exposed to the force of the extending expandable body, the stabilizing body is less likely to move as it would have to displace much more tissue. Additionally, the tissue engaged at the lateral and proximal and distal extents of the stabilizing portion (i.e. around the perimeter) is less likely to be moved anteriorly as it is close to the vaginal sidewalls and so can't deflect anteriorly the way the anterior wall does, but would rather have to stretch. As a result, the expandable portion extends posteriorly because it is more difficult to move the stabilizing portion anteriorly. However, if the stabilizing body could deform under the pressure of the force of the expandable body (pressures and expandable body sizes provided in Earlier Applications and herein), for example, by bowing such that the midline of the stabilizing body is moved anteriorly and the lateral extents are pointed posteriorly, it would lose its resistance to moving anteriorly as it no longer presses against the anterior wall as a flat surface, but rather a curved one, making the area of tissue engagement smaller and the lateral extents of the stabilizing body not engaging the vaginal walls, but rather bending and conforming to them. It, therefore, can be important for the structural integrity of the device to ensure that the extension does not cause the device to bend or fold to the extent that the extension does not create a secure enough protrusion into the rectum to inhibit the unwanted passage of stool. In addition, the structural integrity of the device can be sufficient to withstand any distally-directed force from the extension that can cause a device to collapse in-plane, or fold out-of-plane as the device is pressed against the interior surface of the vaginal opening, resulting in device expulsion. The structural integrity of the device can resist this by resisting the shape changes that would allow it to be expelled. For example, if the device folded, like a taco, or like the bowing example provided above, it could become narrow enough to slip out of the introitus. Or, if the device narrows laterally (as it does during collapse, e.g. shown in FIG. 1D) it could also slip out of the vagina. The planar stiffness of the stabilizing body (resisting out-of-plane bending or bowing), and the lateral rigidity of the stabilizing body (resisting in-plane collapse) can help prevent shape changes tending towards expulsion. The planar stiffness is accomplished in the device of FIGS. 1A-1D and 2A-2G by using a frame that is comprised of rigid segments (e.g. 32, 34, 36, 38) that are stiff enough to resist substantial flexing under the loads of the expandable body and body forces. These segments are interconnected by hinge joints (e.g. 40, 42, 44, 46) that allow only for in-plane rotational motion between segments. This interconnected frame therefore is configured to only freely change shape (via changes in angles between segments) within the plane of the frame, and as a result cannot bend out-of-plane. The hinges prevent any segment from lifting or dropping out of the plane formed by the other segments. The lateral rigidity (resistance to lateral collapse or in-plane collapse) is provided by the resistance of the individual segments to bending in-plane, and the fact that one of the hinges can lock. The 4 segments of FIG. 2A-2D form a 4-bar linkage. Locking only one hinge therefore turns the assembly into a 3-bar linkage which is constrained such that motion is not possible at any of the joints, thereby preventing collapse. Therefore, in the locked state, when the device is squeezed laterally (for example by the narrowing vaginal walls as the device is being pushed anteriorly by a cough), the force is transferred through the stiff segments, which do not substantially bend, to the joints, which are restricted from moving. As a result, the device maintains its width and cannot slip out of the vagina.

As described above, and presented in FIGS. 1A-1E, this structural integrity can be provided by the structural perimeter itself. That is, there are no cross bars, tension elements, or other structural elements that span across the perimeter to provide in-plane and out-of-plane stiffness. Instead the stiffness is provided by the rigidity of the segments and the constraint of the joints. It can be advantageous to provide rigidity in such a way devoid of structural elements spanning the perimeter formed by the interconnected frame. Some of the advantages of not having structural elements spanning the perimeter include: more space for collapse and less material inside the vagina.

As noted elsewhere in this application, the concept of an interconnected frame that provides structural integrity to the stabilizing body and also allows for collapse is not limited to only the embodiments described above, comprising 4 rigid segments and 4 constrained hinges. For example, if one of the 4 joints 40, 42, 44, 46 of FIG. 2A were disconnected or not constrained to only 1-degree of rotational motion, the overall interconnected frame would still only change shape within the plane of the frame because all segments would still have at least 1 joint that is constraining it to planar motion. Embodiments with more than 4 segments are also described herein. However, all embodiments can be configured to resist out-of-plane bending and lateral collapse as described above to suit the needs of an intravaginal rectal occlusion device.

In some embodiments, the specific portion of the stabilizing body that the extendable portion is attached to can change between a state where it has a fixed geometry, and a state where its geometry can change. For example, in FIGS. 1A-1C, this is accomplished by locating the extendable portion over the proximal hinge, which becomes fixed at a pre-defined angle when lock mechanism 16 is engaged (due to the fact that all other frame segments are rigid and at least 3 of the hinges are constrained to 1 degree of freedom of rotational motion), and is less rigid when the locking mechanism is disengaged. As described elsewhere, the structural support for the extendable portion is particularly important for treating fecal incontinence. It can therefore be advantageous to have the rigid characteristics of the frame extend in some manner to the extendable portion.

In a preferred embodiment, only one joint (e.g., joint 46) is locked to provide the stability described above. To facilitate this, the segments are resilient, and the joints are sufficiently constrained to the motion described above. If some of the segments or joints are not rigid or constrained as described above, there will be more deformation of the device when acted upon by a force, which can inhibit the ability of the device to secure the expandable body against the forces of the posterior vaginal wall and stool pressure. There can be advantages to utilizing a single locked joint. For example, as described above, in a preferred embodiment, this lock is located on the hinge opposite the expandable body. In this configuration, the locking mechanism is free from any space or folding constraints resulting from the expandable body. Additionally, this places the lock at the distal most (and therefore most accessible) portion of the vagina, so manipulations needed for interacting with the lock mechanism are best facilitated.

In a preferred embodiment as shown in FIGS. 1A-1C, the expandable body 14 is located proximate to the periphery of the frame. The expandable body is generally located proximal to the widest lateral portion of the stabilizing body, as described in Earlier Applications. Such a configuration can reduce the lateral stretch on vaginal tissue in this area when the expandable body extends posteriorly. Reducing the stretch in this area maintains slack in this region and allows the expandable body to effectively extends towards the rectum and occlude or partially occlude the rectum. The expandable body can be directly or indirectly connected to the segments that form the proximal hinge. The body can be connected in such a way that the hinge is still allowed to fold. For example, the expandable body can comprise a flexible or elastomeric material that is affixed to the hinges, such that the flexible or elastomeric material moves with the hinges (e.g. soft material 108 and 112 partially serve to connect the extendable portion to the stabilizing body).

In particular embodiments, the extendable portion and/or its support can encompass a portion of the stabilizing body and the collapsible frame. It can, for example encompass a portion of the stabilizing body and collapsible frame that changes shape between the collapsed and un-collapsed state. In the example of FIGS. 1A-1E, this portion of the stabilizing body comprises a hinge 42, but it can comprise any number of types of joints, as described elsewhere in this disclosure. The extendable portion and/or its support can change shape to accommodate the changing shape of its encompassed portion of the stabilizing body. For example, FIG. 1D shows the expandable portion and its soft material supports accommodating a closed configuration where its encompassed joint (at hinge 42) is at its most acute angle. In FIG. 1E, the extendable portion and its supports are accommodating an open configuration where its joint is at an angle of 0°. Alternately, the extendable portion and/or its support can be decoupled from this motion by mechanisms described elsewhere in this disclosure.

The expandable body 14 (e.g. as shown in FIG. 1E) can alternately be connected to a support feature which extends from the collapsing frame either distally, proximally, or is biased laterally. Examples of such support features are provided by FIGS. 9-12 and discussed further below. This support feature can transmit forces applied to the expandable body to the frame. In some embodiments, this support feature and/or the expandable body do not limit the lateral collapse of the device to less than about 10%, about 30%, about 50%, or about 75% of the nominal deployed width of the device. In some embodiments, this support feature and/or expandable body do not extend proximally beyond the widest lateral portion of the stabilizing body in the open configuration. In some embodiments, this support feature does not extend proximally past a line drawn between the approximate midpoints of the lateral arms (in the example of FIG. 2A, approximate midpoints of lateral arms are hinges 40 and 44), and preferably does not interfere with the ability of the midpoints of the lateral arms (e.g. 40, 44) to reduce the distance between them by more than about 10%, about 30%, about 50%, about 75%, about 90% or about 100% (contacting each other). The above described support feature can be configured to collapse or fold along with the stabilizing frame; this collapsing or folding being accomplished as a result of the support feature being kinematically linked to the collapsing frame, or by being compressed by surrounding materials.

Figure 9A:
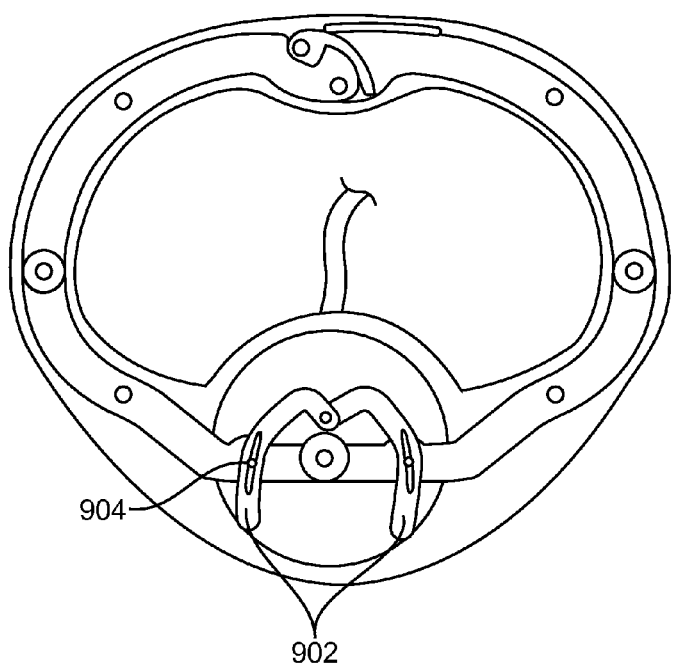
FIGS. 9A-B illustrate an embodiment of a collapsible intra-vaginal device.
Figure 9B:
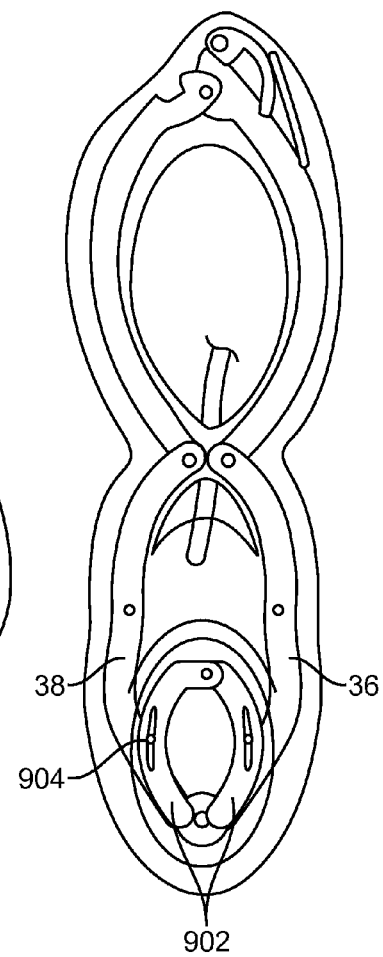

An exemplary embodiment of an additional support feature is shown in FIGS. 9A and 9B. In this embodiment, the expandable body is more rigidly supported by features of the stabilizing body. The advantage of more support for the expandable body is that the expandable body can be less likely to be pushed out of position due to resistance to expansion from the vaginal walls, stool pressure or other anatomical forces such as a cough. The embodiment of FIGS. 9A and 9B include two additional support segments 902 mounted to the proximal frame segments where the expandable body is supported. These segments can be mounted via joints such as hinges so that they can move with respect to the frame in a defined way. In this particular embodiment, these additional segments are also hinged to each other, further constraining their motion. Alternatively, these segments can be coupled to the frame in other ways such as via an adhesive or a flexible adhesive that more loosely constrains the motion of the additional segments. The geometry and mounting of the segments can be such that when collapsed, they do not interfere with the collapsing frame. This geometry is possible by the size and shape of the segments which allows them to fit within the space created by the collapsed segments 36 and 38. In the embodiment of FIGS. 9A and 9B, the additional segments 902 are rounded on their proximal end and have a bend on the distal end to more efficiently and supportively occupy space over the expandable body but not interfere with the folding for the frame. These segments can be placed between the expandable body and the frame, or they can be placed below the frame. The curved portion of the bars also prevents cutting of the cushion material and allows space within segments 902 in the collapsed state for portions of the expandable body. The additional segments 902 can optionally have racetrack slots 904 on them through which posts fixing them to the frame are mounted. The slots are aligned to the device length in the collapsed state. Another embodiment can have larger arcs on the proximal and distal portions of segments 902 that slide past one another during collapse. This geometry can create more support in the open configuration. Any number of additional segments can be used to support the balloon in the manners described above.

Figure 10A:
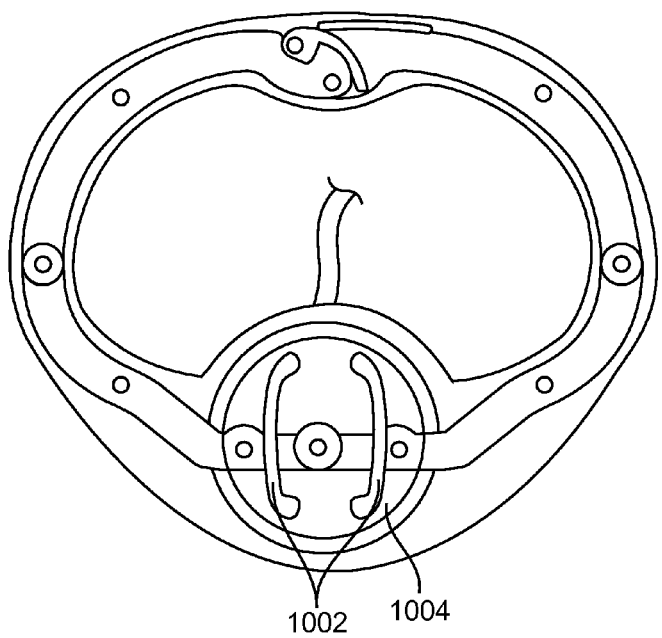
FIGS. 10A-B illustrate an embodiment of a collapsible intra-vaginal device.
Figure 10B:
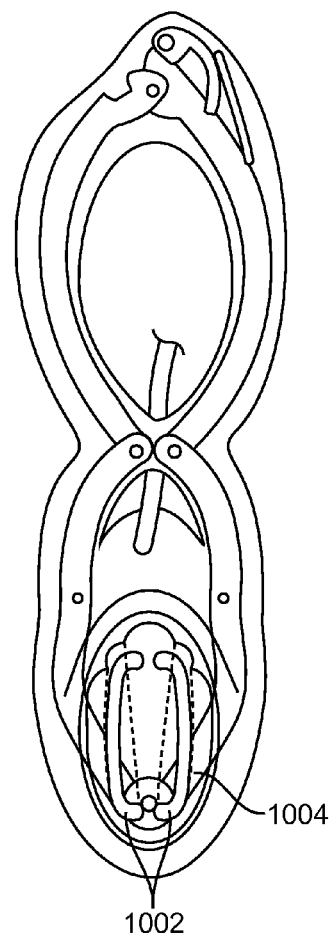

In an alternate embodiment shown in FIGS. 10A and 10B, with additional expandable body supports 1002, a flexible or elastomeric sheet 1004 (that is approximately the same size and shape of the expandable body where the expandable body meets the stabilizing body) is fixed to the posterior portion of the stabilizing frame. With respect to the expandable body, this feature can rest on either side of the frame. At least 1 lengthwise strut crosses the frame, extending on one or both sides of the frame, preferably to at least half the distance from the edge of the frame to the far edge of the expandable body. The struts can be resilient (e.g. 0.005" spring temper steel, or 0.02" polycarbonate), or can be rigid like the rest of the interconnected frame. On collapse, the elastomeric sheet can wrinkle or fold to accommodate to the collapsed device profile.

Figure 11A:
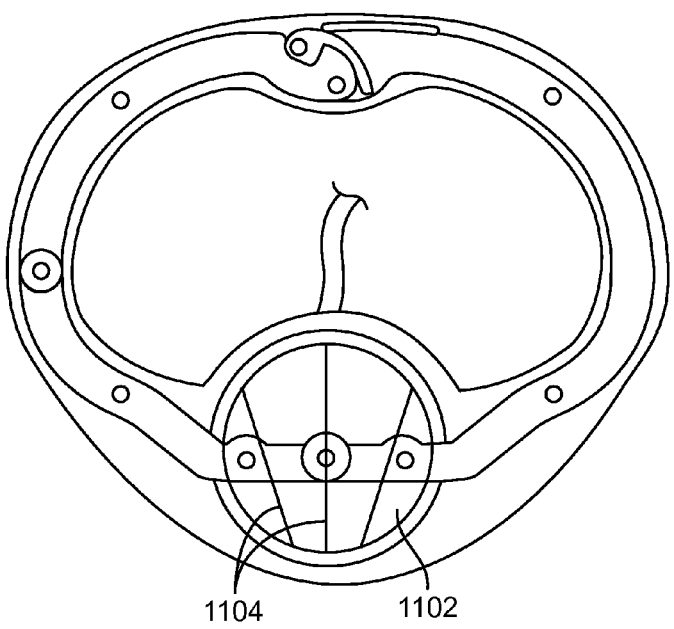
FIGS. 11A-B illustrate an embodiment of a collapsible intra-vaginal device.
Figure 11B:
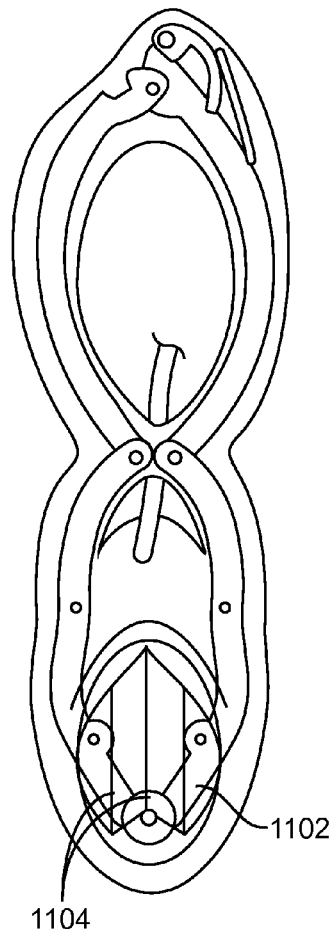

In an alternate embodiment shown in FIGS. 11A and 11B, a disc of thin, stiff polymer 76 (that is approximately the same size and shape of the expandable body where the expandable body meets the stabilizing body) is affixed to the collapsible frame on the posterior portion where the expandable body is connected to the stabilizing body. The disc 1102 preferably has pleats 1104 along its length in multiple locations and a radius that reaches at least about 25%-90% of the distance from the frame to the far edge of the expandable body. The disc can be stiff enough to resist flexure along the pleated lines, and due to its length can create sufficient support for the expandable body. On collapse, the disc can fold at the pleats, allowing it to narrow. In some embodiments it may also flex out of the plane of the stabilizing frame. In a particular embodiment, disc 1102 can have holes or slits cut out to increase flexibility and facilitate bonding.

Figure 12A:
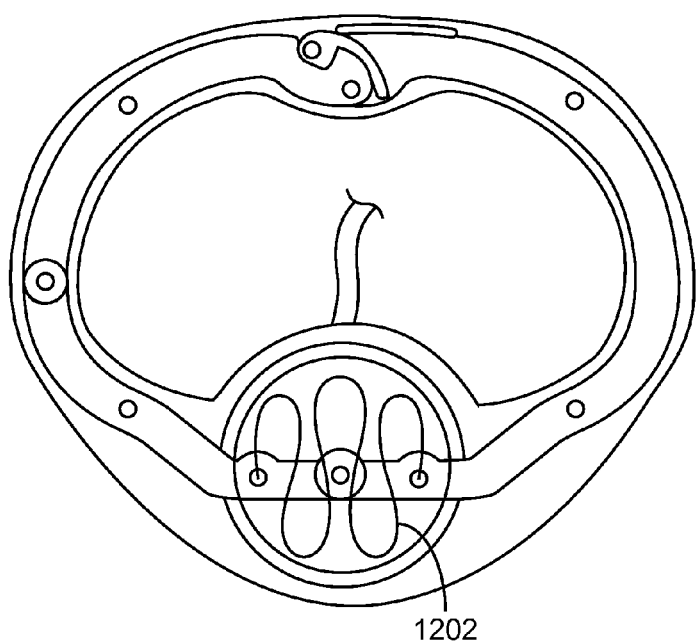
FIGS. 12A-B illustrate an embodiment of a collapsible intra-vaginal device.
Figure 12B:
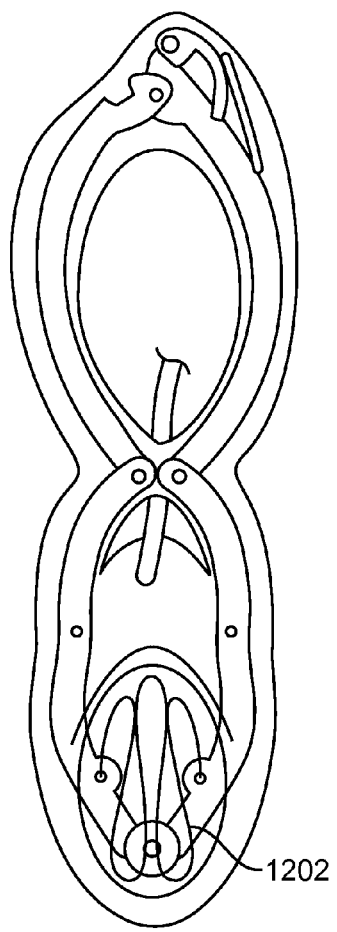
Figure 13A:
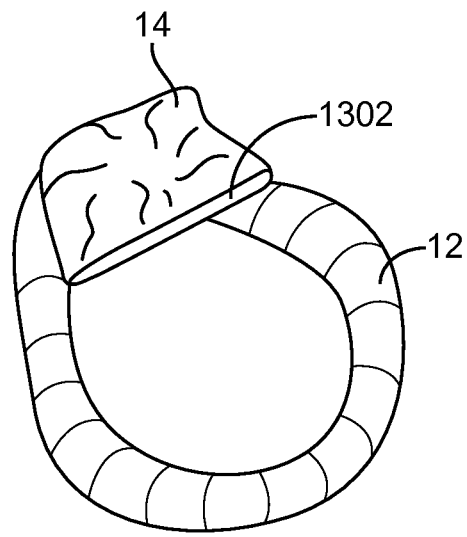
FIGS. 13A-B illustrate an embodiment of a collapsible intra-vaginal device.
Figure 13B:
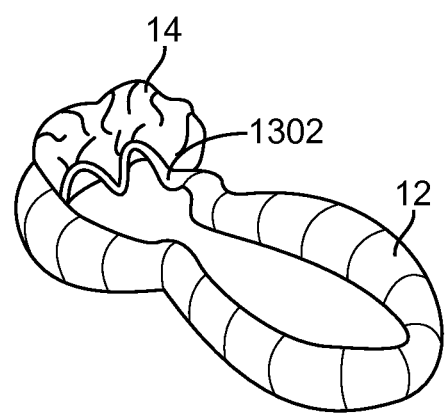

FIGS. 12A and B illustrate another embodiment in which a flexible member 1202 such as a spring temper wireform or flexible plastic shape curves back and forth lengthwise over the frame segments supporting the expandable body, crossing the frame at least one time. The loops can extend at least about 25-90% of the distance from the edge of the frame to the far edge of the expandable body. The spring is joined at least at either end, widthwise, of this section of the frame. An example thickness of a spring wire is about 0.020-0.060", more preferably 0.025-0.040". On collapse, flexible member 1202 squeezes together widthwise and can also flex towards the device's anterior or posterior. In an alternate embodiment, flexible member 1202 has a rectangular cross-section at least 1.5-3 times as tall as it is wide. This shape can increase the support of the extendable member but retains its ability to collapse. In another alternate embodiment, instead of crossing the frame, flexible member 1202 can comprise one or more separate components; where there are more than one, one resides mainly on the proximal side of the frame, and one resides mainly on the distal side of the frame, without either fully crossing the frame. In another embodiment, the loops of flexible member 1202 are maximally stress relieved and take up the majority of the area under the expandable body Whereas at least some of the examples above include supporting features for the expandable body that collapse within the same plane as the stabilizing frame, these same mechanisms, as well as the expandable body itself and any general support structure for the expandable body, can reside above or below the plane of collapse, such that collapse is not interfered with by the expandable body or its supports. This can be accomplished, for example, by mounting the expandable body or its supports to the stabilizing body via one or more flexible connections. An exemplary embodiment is shown in FIGS. 13A and 13B, where the expandable body 14 is a balloon mounted to a flexible platform 1302. An exemplary material for this platform is a sheet of silicone (e.g. 0.04" silicone, 40-60 A durometer), bonded directly to the stabilizing body. In the open state, as shown in FIG. 13A, the platform 1302 partially spans the open space of the stabilizing body 12 such that the balloon is supported. In the collapsed state, as shown in FIG. 13B, the platform conforms to the collapsed state via flexing. It can alternately transition from the collapsed state to the open state by stretching, instead of folding; or by a combination of stretching and folding. In the collapsed configuration, the expandable body and the platform can reside in the plane of the stabilizing body, or it can preferentially reside anterior or posterior to the stabilizing body.

Figure 14:
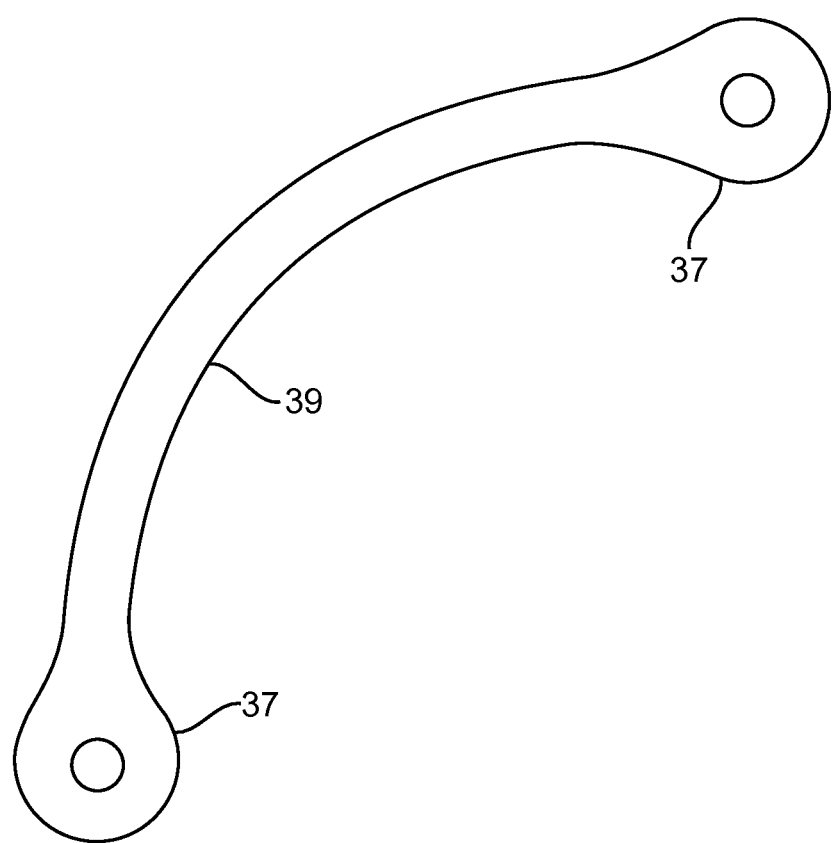
FIG. 14 illustrates an embodiment of a segment of a device frame.

While in the example described above in relation to FIGS. 2A-2E, the width of the segments was generally constant, in some additional embodiments, as shown in FIG. 14, the width of the segments can vary along their length. For example, the width 37 of the segments can widen near the hinges to allow for enhanced hinge constraint, and narrow away from the hinges 39 to allow for a more slender profile or to accommodate more padding to interface with body tissue.

Figure 15B:
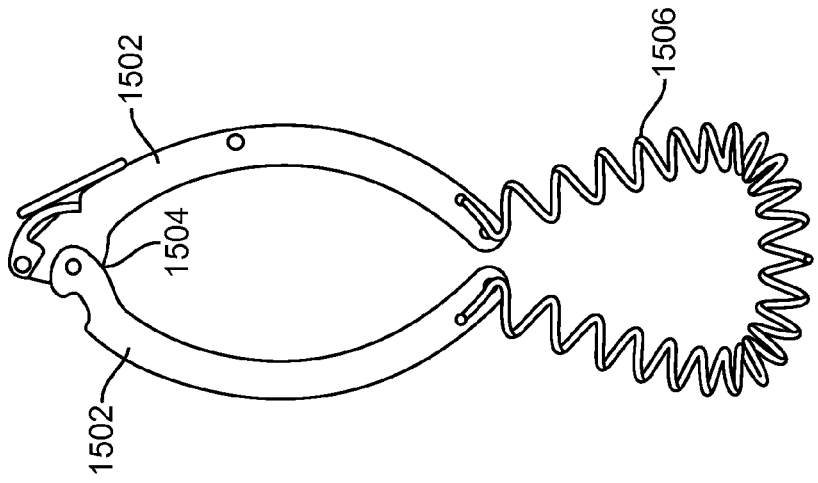
FIGS. 15A-D illustrate an embodiment of a collapsible intra-vaginal device.
Figure 15A:
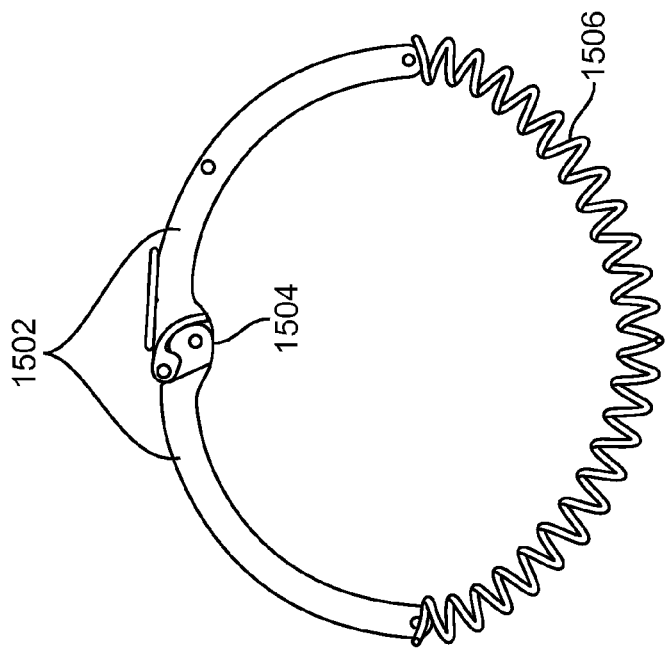
Figure 15D:
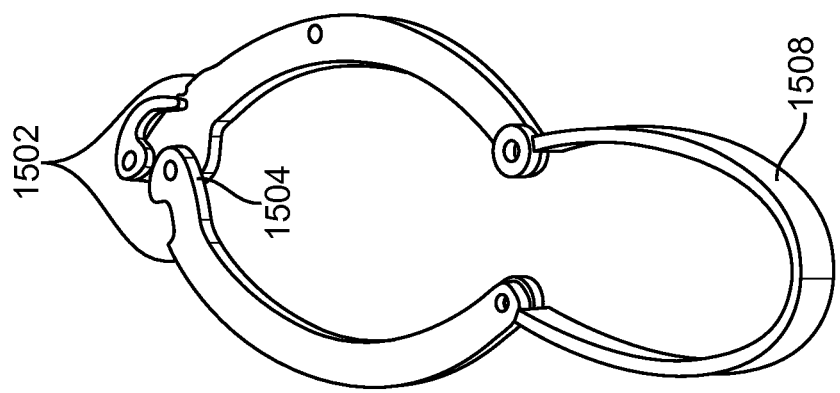
Figure 15C:
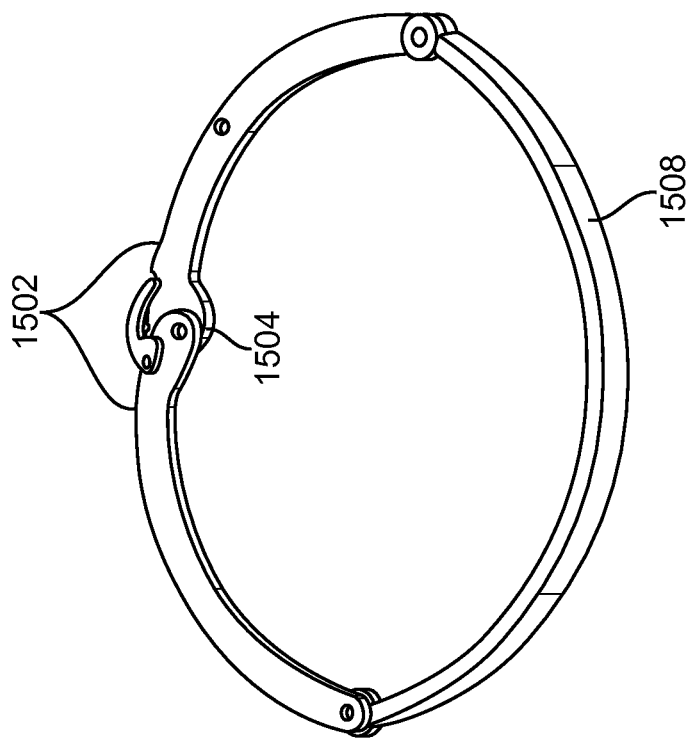

The structure of the device can also be considered as a set of linkages. In the embodiment shown in FIGS. 2A and 2B, the device comprises a 4-bar linkage. The device can be considered as such as long as there are 4 segments coupled by 4 movable joints. Fewer than 4 bars can also be used to collapse the device. For example, FIGS. 15A and B illustrates an alternate embodiment of a device 1500 in which there are minimally 2 rigid segments 1502 connected by a hinge 1504. A spring 1506 or springs are used in this embodiment in place of rigid segments. A hinge 1504 between the rigid segments 1502 can be lockable, which fixes the relative angle or curvature of the two rigid segments 1502, and therefore fixes the rigidity of the stabilizing portion in a lateral direction. In one embodiment, the spring 1506 is biased to be more straight than it is in the open configuration. This bias will tend to open the device from a collapsed state and extra force is required to return the device to a collapsed state (FIG. 15B). In another embodiment, the spring is biased to be more curved than the opened state. This bias will tend to collapse the device (if unlocked) and extra force is required to open the device. In another embodiment, the spring encompasses more of the device perimeter, so that forces applied laterally to the device engage a spring, rather than the solid, locked, frame. The spring in FIGS. 15A and B can alternately be a band 1508 of flexible material, with the longer dimension of its cross-sectional profile extending in the direction perpendicular to the plane of the stabilizing body, as shown in FIG. 15C. This will allow in-plane flexibility similar to the spring, as shown in the collapsed configuration of FIG. 15D, but will limit the amount of out-of-plane bending due to the profile of the band's cross-section.

Figure 6B:
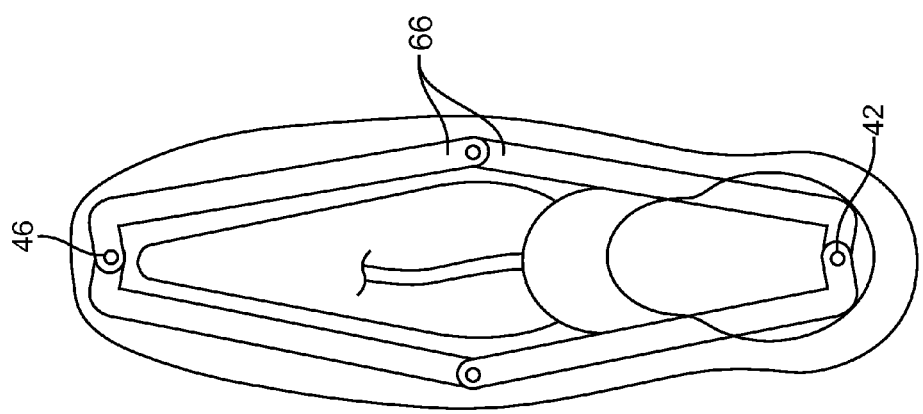
FIGS. 6A-B illustrate an embodiment of a collapsible intra-vaginal device.
Figure 6A:
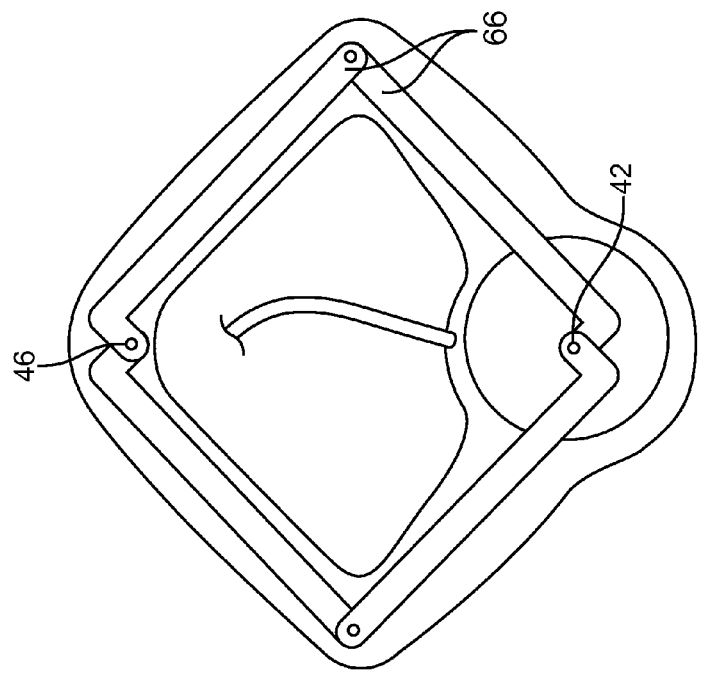

Alternate embodiments comprise a frame structure with segments that are less curved than the segments described above (e.g., segments 32 and 34). This results in a different collapsed form, wherein other aspects of the invention as disclosed herein still apply alone or in combination (e.g. placement of expandable body at periphery; placement of expandable body approximately over distal hinge; use of single locked joint; specific locking mechanisms; unlocking features; removal features; soft covering; gripping surfaces and features; and 3 or more constrained hinges). Exemplary embodiments including straighter segments 66 are shown in FIGS. 5A and 5B, as well as 6A and 6B. FIGS. 6A and 6B additionally illustrate an embodiment in which a pair of opposing hinges 42, 46 (in this case, the proximal and distal hinges) are offset from the rest of the segment towards the center of the device. This allows for collapsing without as much overlap of the segments, as the offset around hinges 42, 46 create a space between sides of the device in a collapsed state, therefore providing for a collapse with less interference, allowing more space for internal components such as the expandable body. Furthermore, the offset hinges provide for more space between the segments; the larger the offset, the larger the space in between the segments when collapsed.

Additional Locking Embodiments

Figure 16C:
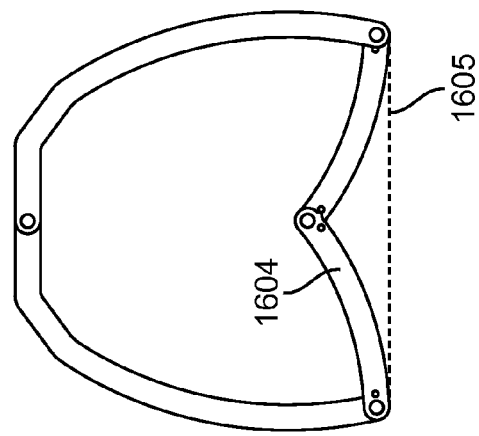
FIGS. 16A-C illustrate an embodiment of a collapsible intra-vaginal device.
Figure 16B:
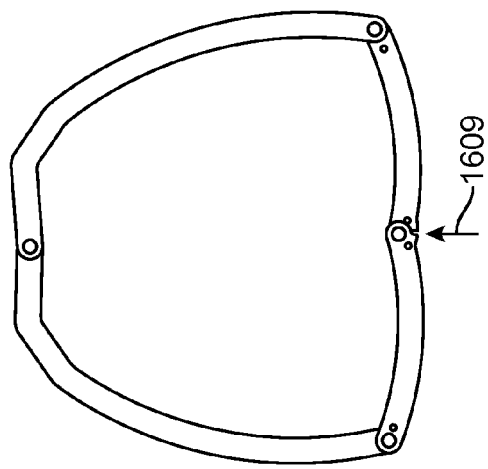
Figure 16A:
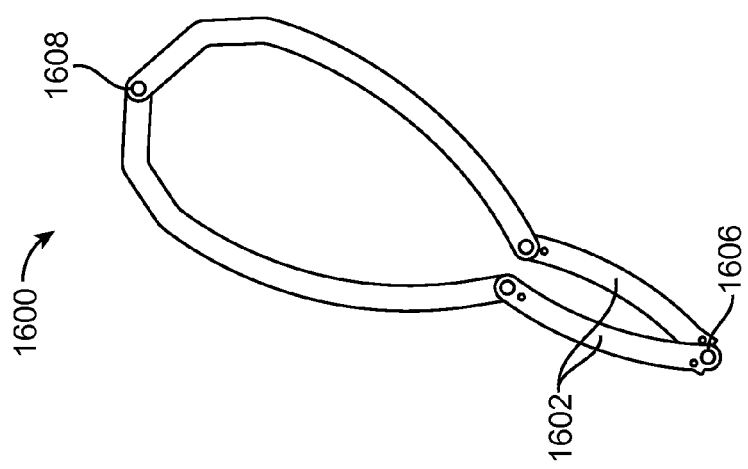

FIGS. 16A-16C illustrate an embodiment of a device frame 1600 that utilizes an over-center lock. This embodiment provides for a collapsible frame with two shorter segments 1602 on the distal portion of the frame that allow the device to be stable in a collapsed (FIG. 16A) or open configuration (FIG. 16C). The segments 1602 can be roughly symmetrical across a line drawn between hinge 1606 and 1608. Once the device is inserted, pressing inwards in the direction of arrow 1609 on the two segments, as indicated by the arrow in FIG. 16B, causes them to pass through a wider state, until they pass a line 1605 drawn between the lateral hinges. One or both of segments 1602 have a raised feature 1604 that does not inhibit the motion of the other segment 1602 in the collapsed state, but when the segments 1602 are flipped inward, as shown in 16C, the features 1604 interact with the other segment's motion, creating a hard stop which limits the amount the frame can collapse. At this point, further force in the direction of arrows 1609 does not cause any of the hinges to rotate further as they are fully kinematically constrained. The segments 1602 are located distally to make it easier for a patient to reach them with a finger. A pull cord on the segments 1602 when activated, can pull the short segments back distally, as indicated by the arrow of FIG. 16C, and allow the device to collapse and be withdrawn. Force from the walls of the patient's vagina cause the device to remain stably open, but can be assisted by a widthwise spring element that can prevent accidental collapse if the cord is pulled inadvertently.

Figure 17A:
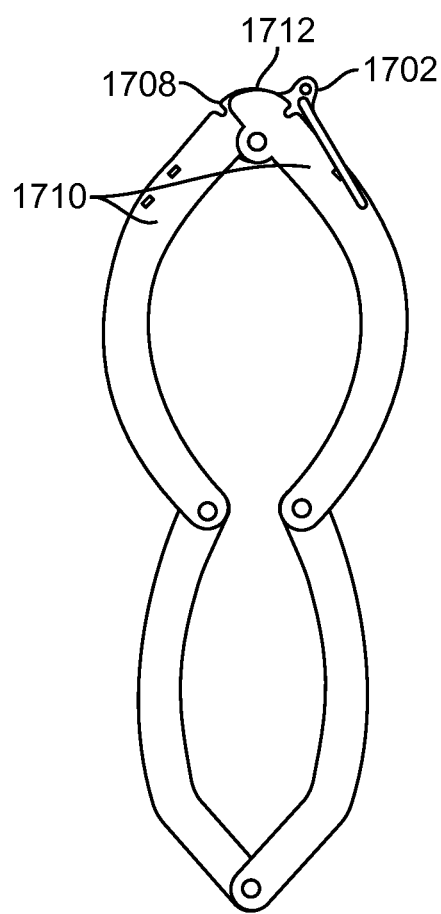
FIGS. 17A-C illustrate an embodiment of a collapsible intra-vaginal device and a locking mechanism.
Figure 17B:
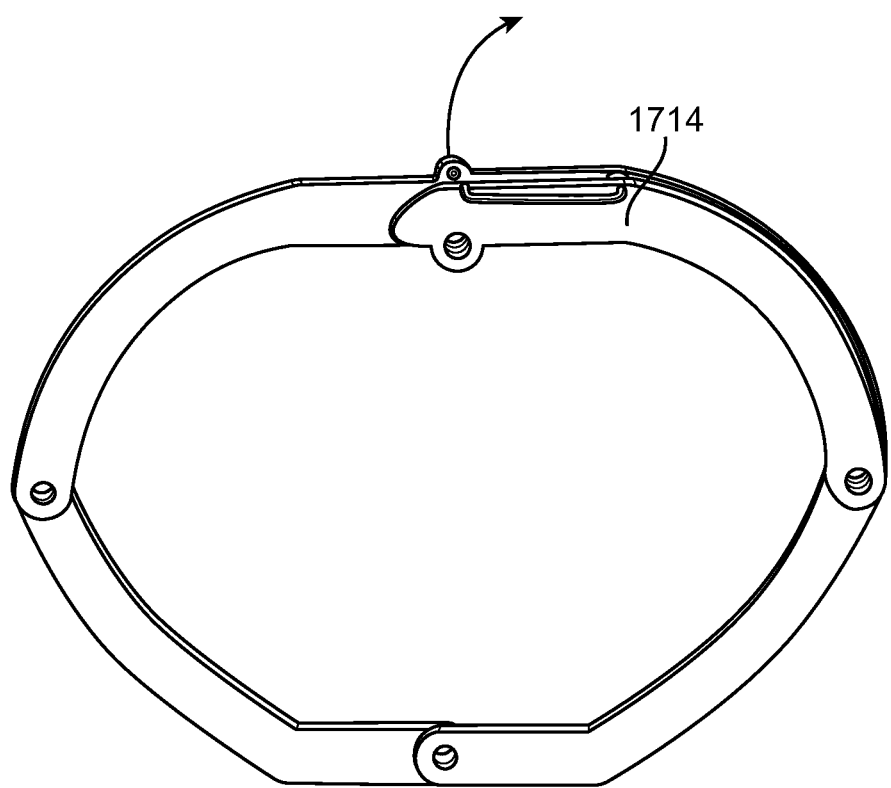
Figure 17C:
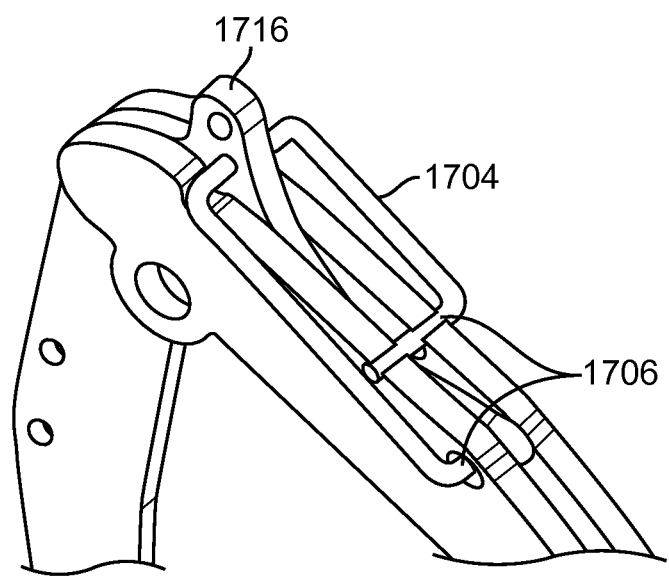

FIGS. 17A-C illustrate an embodiment of a device frame 1700 comprising a pin-in-notch design. This embodiment provides for a collapsible frame wherein a pin or tooth 1702, preferably spring loaded, can lock the device into a stable state. The spring can comprise a wireform 1704 with feet 1706 offset from one another to generate force when the spring is lifted out of plane. As the device is opened, notches 1708 on neighboring segments 1710 of the device frame align allowing the tooth to drop in. At this point, further movement of the segments relative to one another is prevented. At least one of the segments has a ramped face 1712 leading up to the notch so that when transitioning from a collapsed state to the open state, the spring rides up the ramp, and until the pin can engage. In this embodiment, one segment 1714 of the two segments is doubled up sandwiching its neighboring segment. Once the pin has engaged, the pin can be lifted to allow the segments of the device to rotate freely relative to one another. The notches 1708 have slightly curved walls to prevent them from trapping the pin 1702. A lever 1716 can be included to manipulate the pin and/or spring into the correct placement and facilitate its actuation. In FIG. 17B, the lever 1716 is sandwiched between the doubled up segments and allows the pin 1702 to be lifted from the notch evenly via a pull cord attached to its loop, by pulling in the direction indicated by the arrow in FIG. 17B. An advantage of this lever is that it can fix the location of a tensile element with respect to the pin and reduce any rotational moments (in a direction out of the plane of the stabilizing body) applied to the pin during removal. The pull cord can pass through the lever to the frame so that once the tooth has been lifted free of the notches, the force of the user removing the device transfers directly to the frame.

Figure 18A:
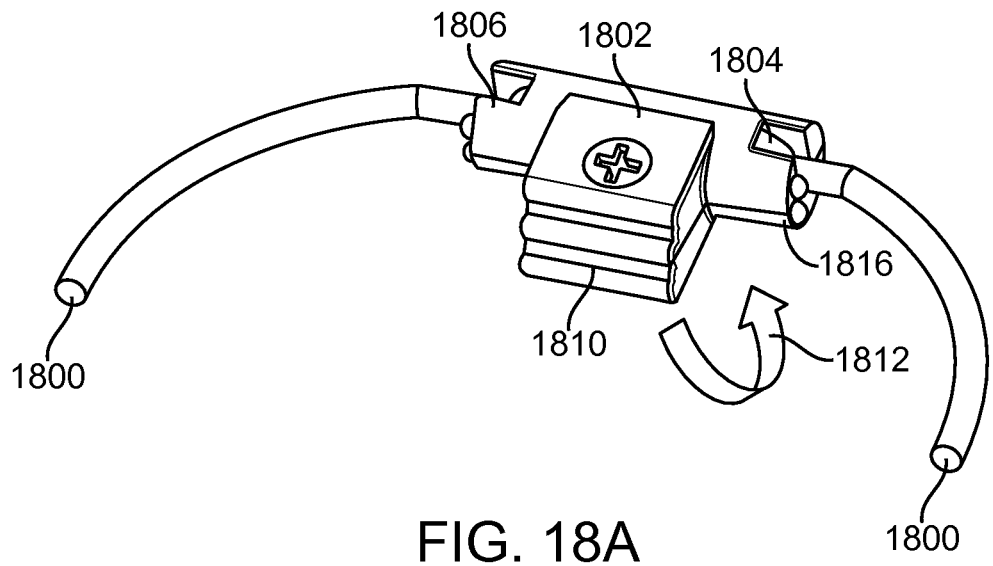
FIGS. 18A-B illustrate an embodiment of a locking mechanism for a device frame.
Figure 18B:
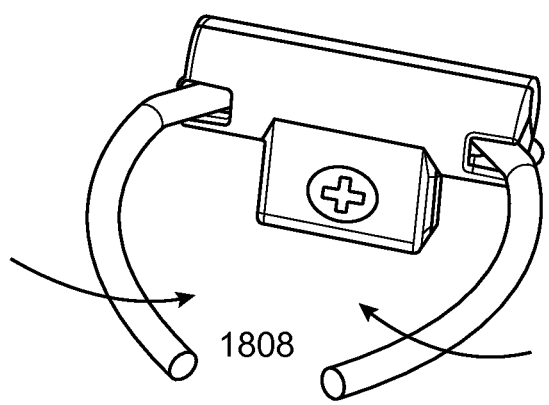

FIGS. 18A and B illustrate an exemplary rotating lock design. This embodiment provides for a collapsible frame wherein the locking feature is activated by rotation (out of the plane of the stabilizing body) of a feature. In this particular example, two segments 1800 of the frame (preferably the distal-most segments in a frame such as 32 and 34 as described in FIG. 2) have rounded tips 1806 that are constrained within the locking mechanism 1802 like a ball-in-socket joint. The locking mechanism houses the segments 1800 and in one orientation has slots 1804 that allow the frame segments to swing inwards (direction of 1808), collapsing the device for insertion or removal. These slots can be exposed to the segments when the user rotates the locking mechanism (an exemplary rotation direction is shown by arrow 1812). When these slots are exposed to the segments, the segments are free to rotate into them, causing the device to collapse. Once the segments enter the locking mechanism's slots, their presence in the slots interferes with the locking mechanism's ability to rotate in the direction opposite of arrow 1812. The rotation of the lock mechanism when switching the device to a collapsible state can be against a spring element. This spring element causes the locking mechanism to return to a locked state when the device is opened sufficiently such that the segments clear the slots, allowing a return rotation of the lock mechanism. The pull tab (e.g. tab 1810) or cord can assist in device removal as well as unlocking. In FIGS. 18A and 18B, only two segments of a collapsible frame are shown. These can be connected to additional segments as described elsewhere. As shown, with ball-in-socket joints at one end which are capable of allowing 3 degrees of rotational motion, there are preferably 3 other joints among the segments comprising the full interconnected collapsing frame which are constrained to allow one degree of rotational motion. The segments 1800 can also protrude through the rounded ends 1806, in which case it is possible for the segments to be further constrained in motion by interference with the interior surfaces of the lock mechanism. The ball-in-socket joint serves an additional purpose of preventing any translative motion between the ends of segments 1800. In other words, the lock mechanism constrains and fixes the position of a portion (in this case, the approximate terminal ends) of the segments 1800 with respect to each other and other portions of the stabilizing body. In some cases, in the closed state, a lateral force applied to segments 1800 can create a rotational force on the lock housing. This is due to the segments pressing against an internal surface of the lock housing. This can potentially lead to enough of a rotational force that the lock housing rotates and the segments are allowed to move into the slots. An embodiment for preventing this comprises a detent in the lock mechanism such that when the device is inserted and allowed to open, the lock mechanism rotates until frame segments 1800 are presented with a detent 1816. This detent limits the rotation of the lock mechanism by interfering against a segment 1800.

More generally, a housing can be used to house portions of adjacent segments such that at one rotational position, the segments are fixed in a particular degree of freedom (e.g. fixed from rotating in the direction that causes the collapse of the stabilizing body), and at another rotational position, they are free to move in a direction that causes the collapse of the stabilizing body. Provisions should also be provided to prevent the ends of the segments that interact with the housing from translating apart from each other. While the above embodiment accomplishes this with ball-in-socket joints, it can be accomplished by other means as well, including, but not limited to direct connection of the segments via a flexible joint or a hinge.

Figure 19A:
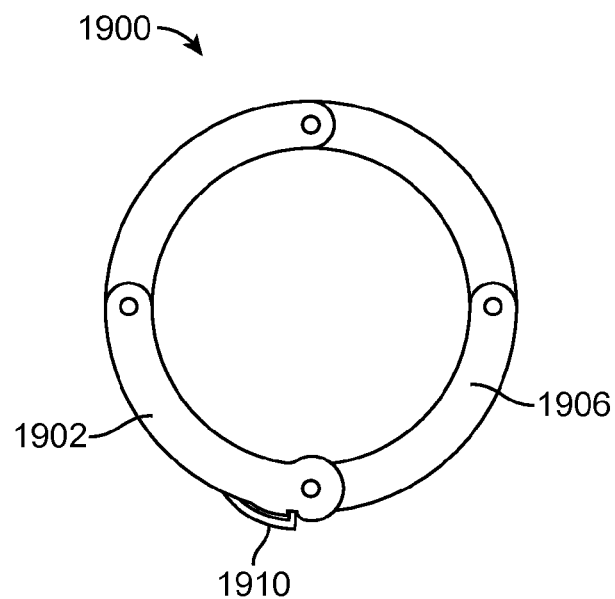
FIGS. 19A-B illustrate an embodiment of a collapsible device frame.
Figure 19B:
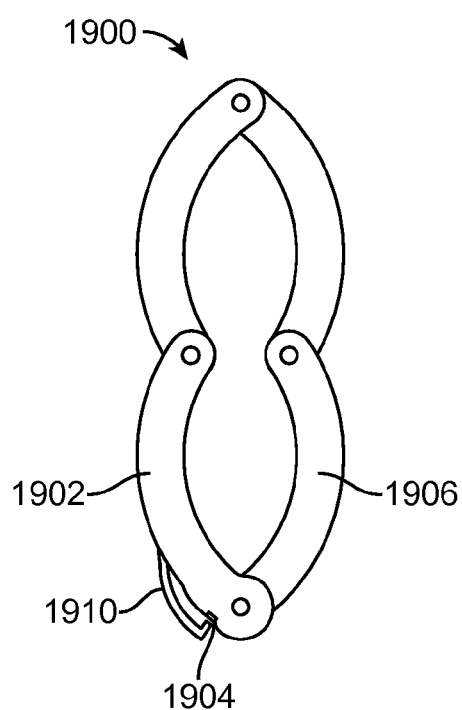

FIGS. 19A and 19B illustrates a device frame 1900 comprises four curved arms connected by joints to form a loop. The frame 1900 comprises a first arm 1902 1904 at one end of the arm 1902. The frame 1900 also comprises a second arm 1906 with a. Relative rotation between arms 1902, 1906 opens the frame 1900. Rotation sufficient to reach the locking point allows tab 1810 access to the notch. A tab 1810 can be configured to engage the notch, fixing the arms 1902, 1906 in the open configuration, as shown in FIG. 19A. The tab 1910 can be rotatably fixed to the frame 1900, as shown in FIG. 19B.

FIGS. 20A-C illustrates a device frame 2000 comprising a rotating hinge locking mechanism. The frame comprises four curved arms connected by joints to form a loop. This embodiment provides for a collapsible frame with a locking mechanism that consists of a hinge that when rotated out of plane prevents the frame from collapsing. One embodiment of this design is a frame with 3 hinges 2002 in plane and 1 hinge 2004 that is able to rotate. Resilient members, e.g., over-wound springs 2006 attached to the frame segments, keep the rotatable hinge 2004 out of plane until the user, via a finger tab or pull cord, rotates the hinge 2004 in the direction indicated by arrow 2008 in FIG. 20B, into plane. Once in plane, the frame 2000 is able to collapse, as shown in FIG. 20C. An advantage of the design is a lack of mechanical disadvantage. The locking mechanism rotates in place until the point at which it can release.

Figure 21A:
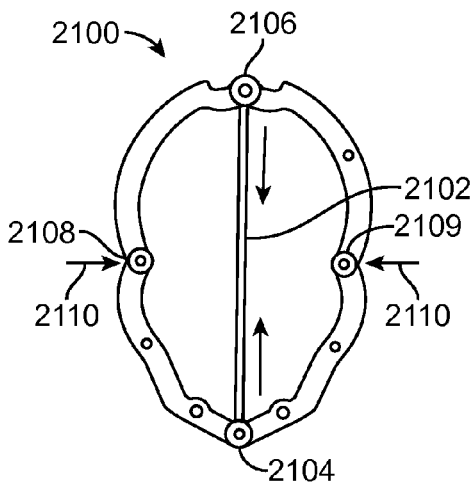
FIGS. 21A-B illustrate an embodiment of a collapsible device frame.
Figure 21B:
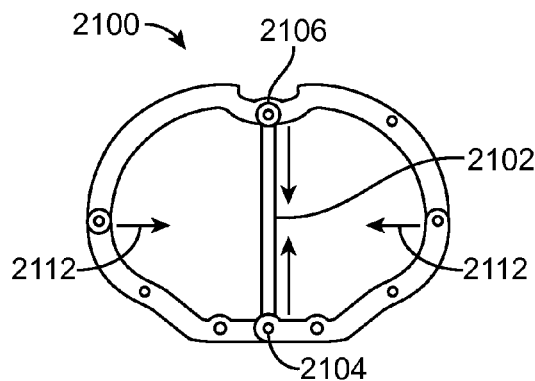

FIGS. 21A and B illustrates a device frame 2100 comprising four curved arms connected by joints to form a loop. The device comprises a resilient or spring element 2102 (e.g., a rubber spring) extending across the frame 2100. The resilient element 2102 can be used to assist in device opening. The resilient element 2102 can have a resting state corresponding to the frame 90 being in an open configuration. In some embodiments, the resilient element 2102 can have a resting state corresponding to the frame 2100 holding the stabilizing body open to a degree greater than the degree desired when the device is inserted in the vaginal cavity of a user. Once inserted, patient anatomy can apply pressure to collapse the device to the desired position based on particular anatomy. Upon application of force during device removal, the stabilizing body can naturally collapse as it passes through narrower anatomy. Hard or active stops can be used to constrain frame dimensions.

Figure 22A:
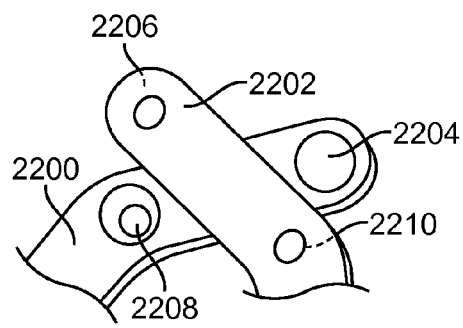
FIGS. 22A-B illustrate an embodiment of a locking mechanism for a device frame.
Figure 22B:
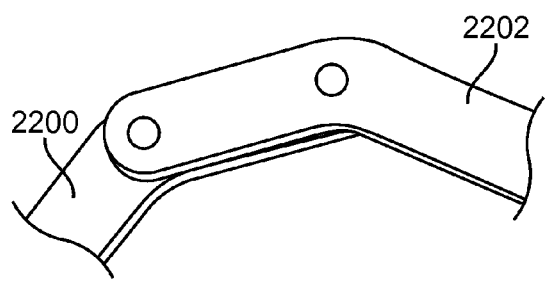

FIGS. 22A and 22B illustrate an embodiment of two arms 2200, 2202 of a device frame comprising detents that can be used to lock a frame in an open configuration. Arm 2200 includes a resilient protrusion 2204 at an end of the arm; arm 2202 includes a resilient protrusion 2206 at the end of the arm, on the surface of arm 2202 facing arm 2200. Arm 2200 includes a depression 2208 configured to mate with protrusion 2204, and arm 2202 includes a depression 2210 configured to mate with protrusion 2206, the depression 2210 positioned on the surface of arm 2202 facing arm 2200. Opening the frame can cause the protrustions 2204, 2206 to catch on the depressions 2208, 2210, locking the frame to resist device closure. The protrusions can comprise spring loaded balls, leaf springs, and the like. In some embodiments, the protrusions can catch on the frame edges.

Figure 23A:
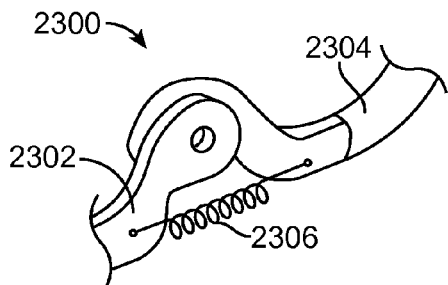
FIGS. 23A-C illustrate an embodiment of a locking mechanism for a device frame.
Figure 23B:
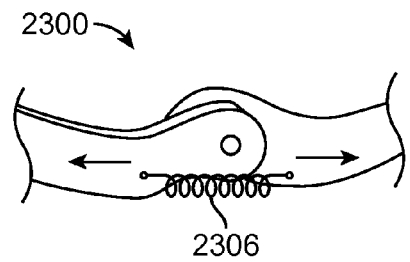
Figure 23C:
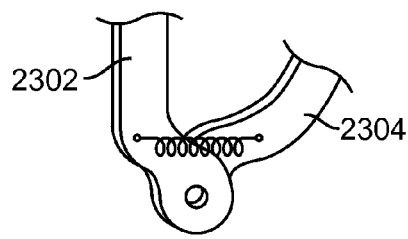

FIGS. 23A-C illustrate an embodiment of a locking mechanism 2300 between two arms 2302, 2304 of a device frame. A spring 2306 or other resilient element extends between ends of the arms 2302, 2304. FIG. 23A depicts a first open configuration, and FIG. 23C depicts a second open configuration. The spring 2306 is in a resting state in both configurations. FIG. 23B depicts the spring 2306 being stretched as the frame transitions between open configurations.

Figure 24A:
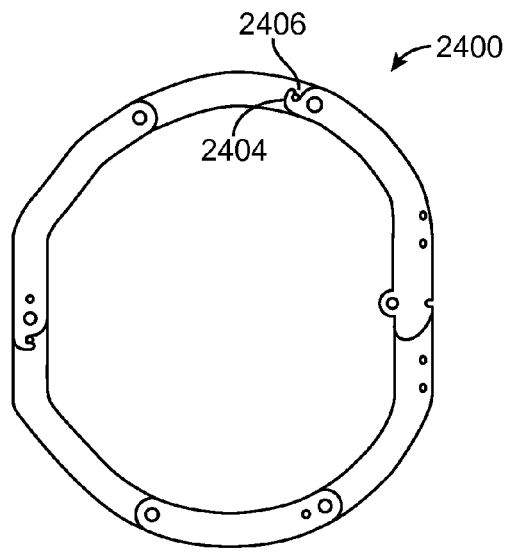
FIGS. 24A-C illustrate an embodiment of a collapsible device frame.
Figure 24B:
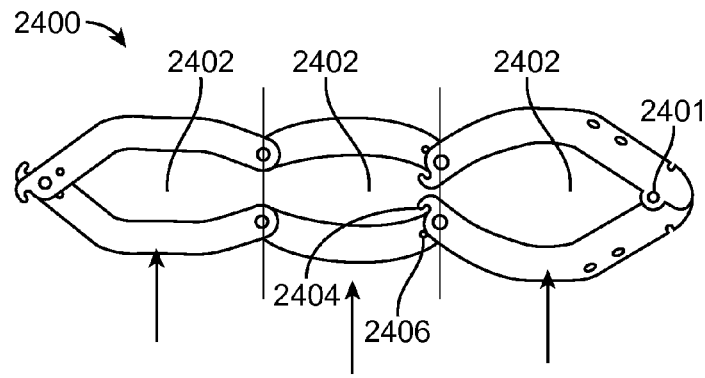

Described above are device frames comprising four curved arms, allowing the frame to collapse in two sections, (e.g., FIGS. 2A-2G, 19A-19B, 20A-20C). In some embodiments, the frame comprises more segments, as shown in FIG. 24A. The frame 2400 is shown in a collapsed configuration in FIG. 24B. Increasing the number of segments can allow the frame to collapse more narrowly, as each section comprises less of the total frame curvature. The frame 2400 shown in FIGS. 24A and B comprises 6 segments and collapses into three sections 2402. Such frames can require more locking mechanisms than a frame with 4 or less segments, or can use a combination of a single locking mechanism (e.g. a lock of the embodiments described above, at hinge 2401) and one or more rotation limiting features to limit the direction that certain segments in certain positions are able to rotate. In an exemplary embodiment, these limiters comprise a feature on one segment that interferes via collision with a feature on another rotationally-linked segment at a certain rotational position. More specifically, the embodiment shown in FIGS. 24A and 24B utilizes hooks 2404 on segments that engage pins 2406 on rotationally-linked segments. These features allow the joints to rotate with respect to each other in one direction to allow collapse, but prevent rotation in the other direction. When a single lock (e.g. at hinge 2401) is engaged, the limiters 2404 and 2406 prevent the other segments from rotating in the collapse direction, rendering the open configuration is stabilized.

Figure 24C:
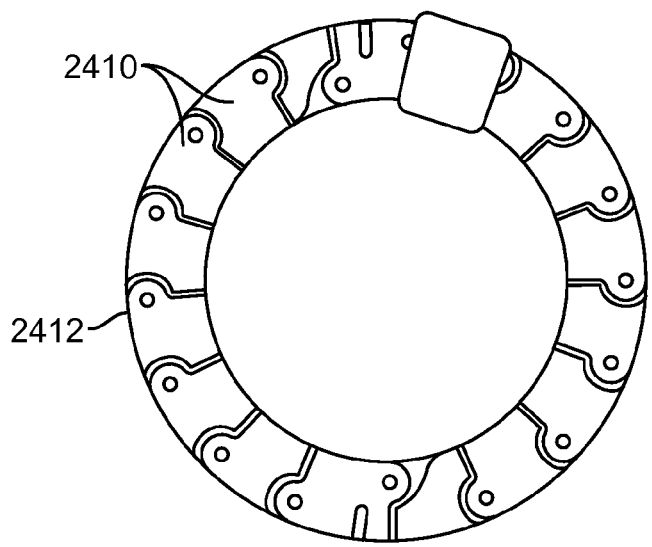
Figure 32A:
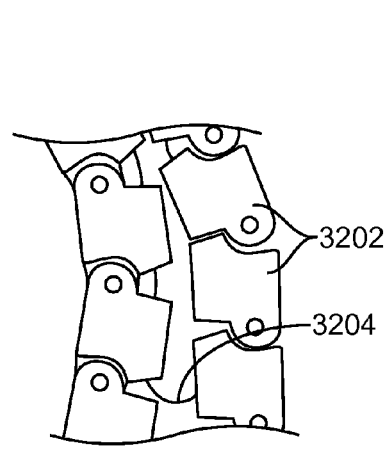
FIGS. 32A-B illustrate an embodiment of a collapsible device frame.
Figure 32B:
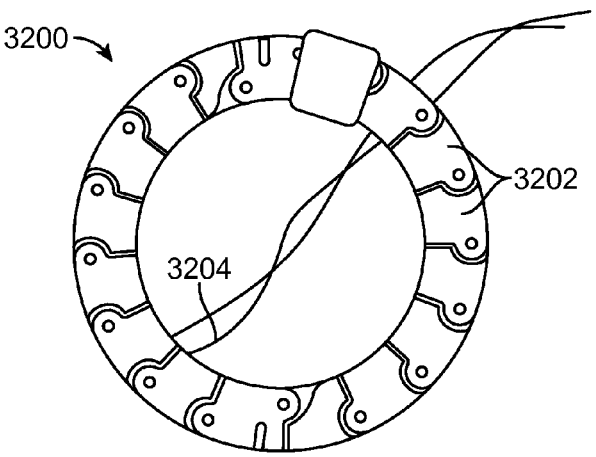

Another embodiment shown in FIG. 24C shows a means of stabilizing multiple segments by utilizing features such as tapered surfaces that allow the segments to act like vertebrae 2410 that are hinged on their wider side 2412, limiting the ability to rotate in one direction. Similar to the above example, this component's shape allows the use of a single locking mechanism to secure the whole assembly in an open configuration. Also shown in FIGS. 32A and 32B is a similar embodiment with a tensile element 3204 running through the segments that can be tensioned to pull the tapered faces of segments 3202 together, aligning the segments in the open configuration.

Figure 25A:
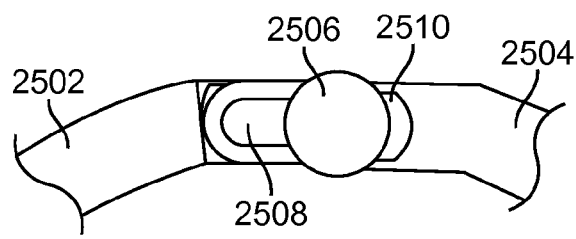
FIGS. 25A-B illustrate an embodiment of a locking mechanism for a device frame.
Figure 25B:
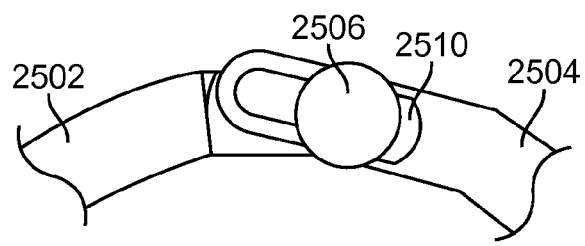

FIG. 25A illustrates an embodiment of a locking mechanism 2500 between a first arm 2502 and a second arm 2504 of a device frame. The first arm 2502 comprises a protrusion 2506 at an end of the arm. The second arm 2504 comprises an opening 2508, (e.g., a slot, a tube, or the like). The protrusion 2506 is disposed within the opening 2508. Sliding the Sliding off or rotating the opening 2508 can free the protrusion 2506 and allow the frame to collapse. For example, the protrusion 2506 can rotate at a wider location 2510 in the opening 2508. When the protrusion 2506 is slid into the wider location 2510, the arms 2502, 2504 can be free to rotate, as shown in FIG. 25B.

Figure 26A:
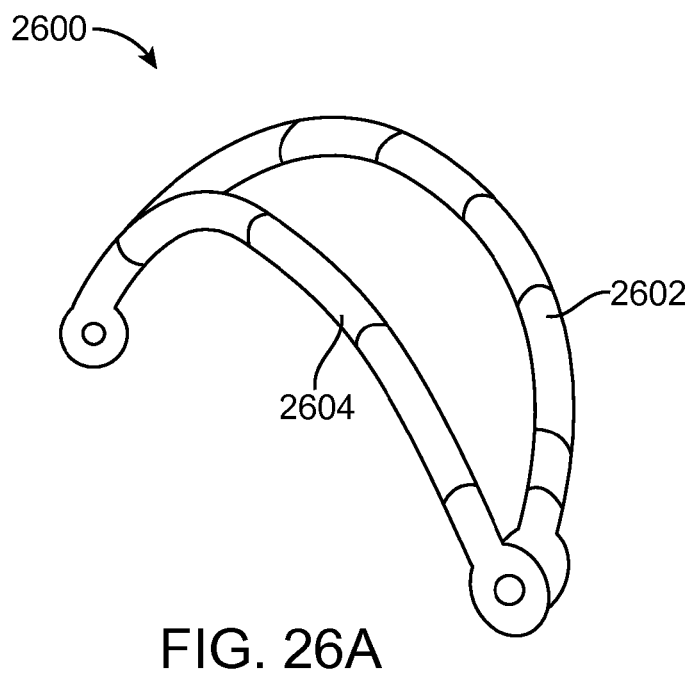
FIGS. 26A-B illustrate an embodiment of a collapsible device frame.
Figure 26B:
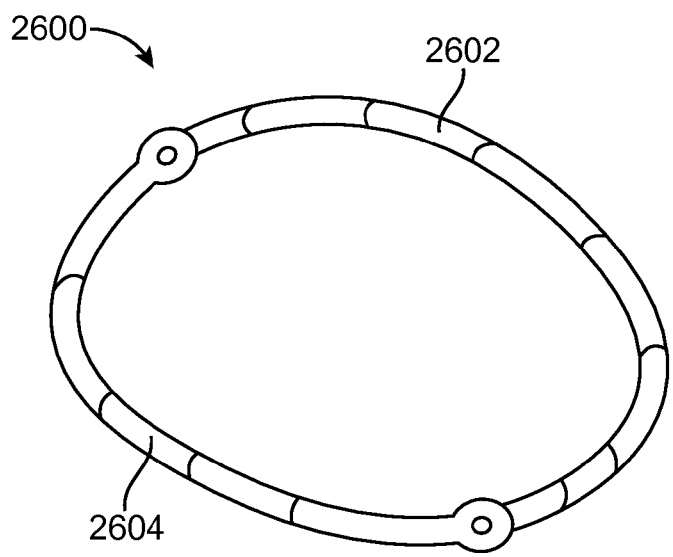

In some embodiments, the stabilizing body can be configured to collapse by folding out of the plane of the primary structure, (e.g., folding together opposing portions of the stabilizing body). FIGS. 26A and B illustrates an embodiment of a frame 2600 configured to collapse by folding the two sides 2602, 2604 over one another. FIG. 26A illustrates the frame 2600 in a collapsed configuration, forming a crescent shape.

Figure 27A:
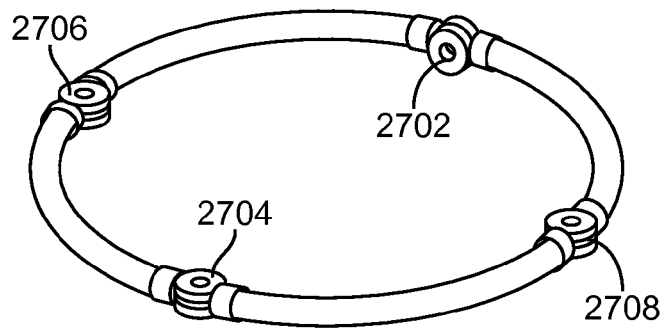
Figure 27B:
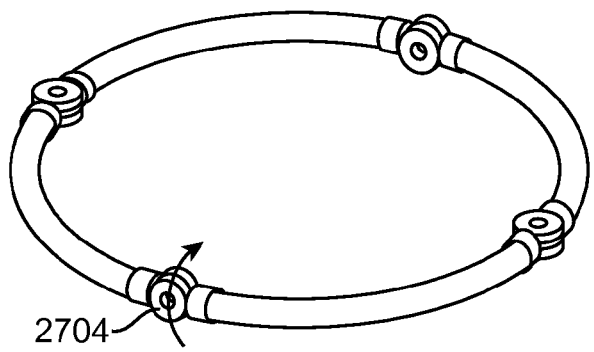
Figure 27C:
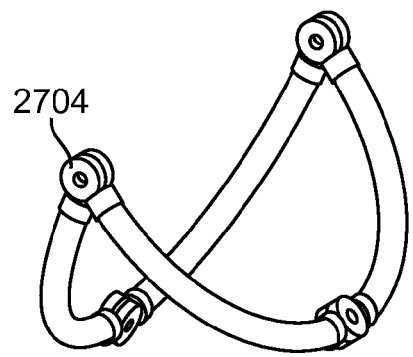

FIG. 27A illustrates an embodiment of a frame 2700 configured to fold together to form a crescent shape, as shown in FIG. 27C. The frame 2700 is then configured to straighten out as shown in FIGS. 27D and E. As shown in FIG. 27A, the frame 2700 comprises a first pair of opposing joints 2702, 2704 and a second pair of opposing joints 2706, 2708. Joints 2702, 2704 allow the frame 2700 to fold over on itself. Joint 2702 is out of plane from joint 2704. Joint 2704 must be rotated as shown in FIG. 27B, before joints 2702 and 2704 can be used to fold the device over on itself, as shown in FIG. 27C. Joints 2706, 2708 allow the device to straighten. Joints 2706, 2708 cannot rotate when the frame 2700 is in a planar configuration as joints 2706, 2708 are out of plane when the frame 2700 is in a planar configuration. Once joints 2702, 2704 are rotated sufficiently, joints 2706, 2708 are able to rotate and straighten the device, as shown in FIGS. 27D and E.

While FIGS. 27A-27C demonstrate an out-of-plane collapsible device with a particular type of locking mechanism (rotatable hinges), devices that fold in this fashion can be locked by any number of locking mechanisms, including the other locking mechanisms described herein.

FIGS. 28A-C illustrate an embodiment of a frame 2800 comprising a cylindrical shape. As shown in FIG. 28A, the body 2800 comprises bi-stable walls that curve inwards such that only force generated by hooking or pulling from the inside of the body 2800 can cause it to collapse. FIG. 28B illustrates a top view of the frame 2800 with an arrow indicating the location at which force can be applied to collapse the frame 2800. FIG. 28C illustrates a top view of the collapsed frame 2800.

Figure 29A:
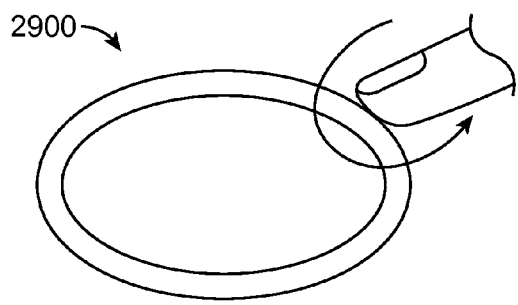
FIGS. 29A-C illustrate an embodiment of a collapsible device frame.
Figure 29B:
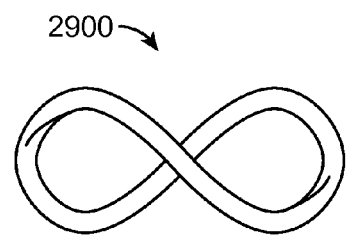
Figure 29C:
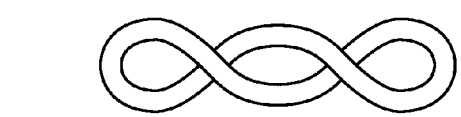

FIG. 29A illustrates an embodiment of a generally loop-shaped frame 2900 (e.g., circular, ovular, rectangular, etc.) configured to collapse by crossing over itself. The collapsed configuration can resemble an infinity sign, as shown in FIG. 29B. The frame 2900 can be twisted further, resulting in a narrower profile, as shown in FIG. 29C. In some embodiments, the frame 200 comprises shape memory materials or metals. The frame 2900 can comprise wires, ribbons, beams. In some embodiments, the frame 2900 comprises beams with flat or concave cross-sections.

Figure 30A:
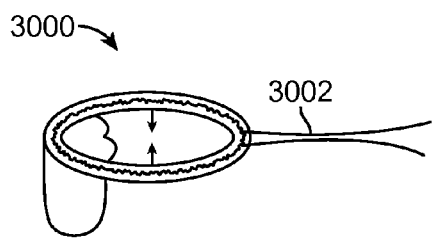
FIGS. 30A-B illustrate an embodiment of a collapsible intra-vaginal device.
Figure 30B:
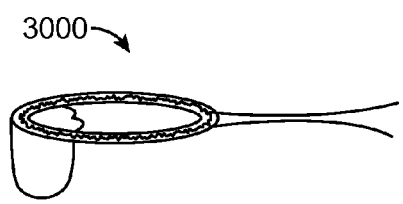

FIG. 30A illustrates an embodiment of a frame 3000 comprising, at least in part, a shape memory alloy. The shape memory alloy can be at rest at body temperature. The frame 3000 comprises one or more lumens 3002 allowing for the application of fluid or current. Application of hot or cold fluid can cause the frame 3000 to extend and narrow (e.g., during insertion and removal). In some embodiments, application of a current causes the frame 3000 to change shape. FIG. 30B illustrates the frame 3000 in a narrowed configuration.

Figure 31A:
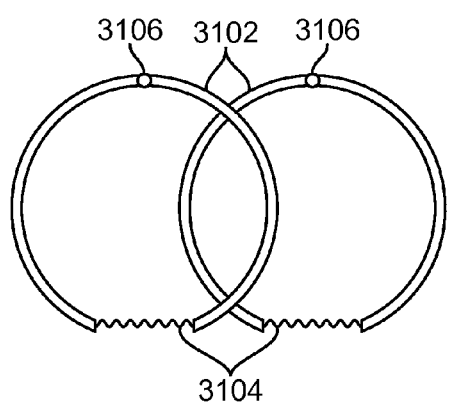
FIGS. 31A-C illustrate an embodiment of a collapsible device frame.
Figure 31B:
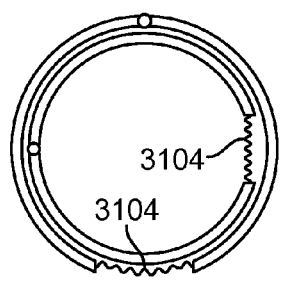
Figure 31C:
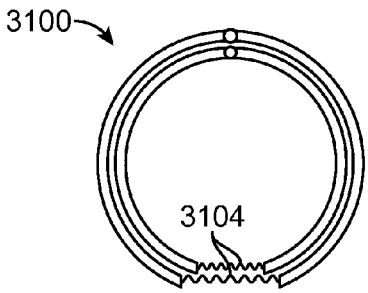

FIG. 31A illustrates an embodiment of a frame comprising two internal components 3102 each comprising a gap or flexure 3104 and a hinge 3106, as shown in FIG. 31A. The internal components are rotatable relative to one another. The frame 3100 is locked in an open configuration when the flexures 3104 are not aligned, as shown in FIG. 31B. Rotation of the components 3102 can cause the flexures 3104 to align (FIG. 31C), allowing the frame 3100 to be collapsed. In some embodiments, an elastic components (e.g., a spring) can keep the components 3102 in a locked state. In some embodiments, the frame 3100 can be locked by rotating or squeezing.

FIGS. 32A and B illustrate an embodiment of a frame 3200 comprising multiple segments 3202 and a tensile member 3204 (e.g., a string) extending through the segments 3202. The segments 3202 comprise tapered features like vertebrae that are hinged on the wider side. When the tensile member 3204 is not applying tension, as shown in FIG. 32A, the frame 3200 can be collapsed or manipulated. When tension is applied, as shown in FIG. 32B, the tapered faces of the segments 3202 engage, and frame 3200 is locked into an open configuration. Tension can be applied via an external force. The tensioning member, while facilitating the opening of the device, is not required for locking. A single lock can also secure the entire vertebrae once it is opened.

Figure 33A:
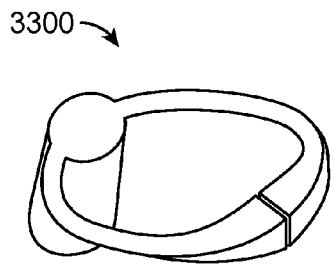
FIGS. 33A-B illustrate an embodiment of a collapsible device frame.
Figure 33B:
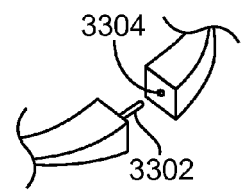

FIG. 33A illustrates an embodiment of a frame 3300 comprising a locking mechanism to stabilize the open configuration. The frame 3300 is generally loop shaped (e.g., circular, ovular, etc.). The frame 3300 includes a break, creating two frame sections. FIG. 33B illustrates the break in the frame in more detail. A pin 3302 is positioned at the end of a first frame section. An aperture 3304 configured to receive the pin is positioned at the end of a second frame section. The pin 3302 and aperture 3304 can snap together to hold the frame 3300 in an open configuration. In some embodiments, the frame 3300 is in a resting state when in the open configuration, so the two frame sections can be disconnected prior to collapse. Other connection mechanisms are also possible. For example, hook features can be used.

Figure 34A:
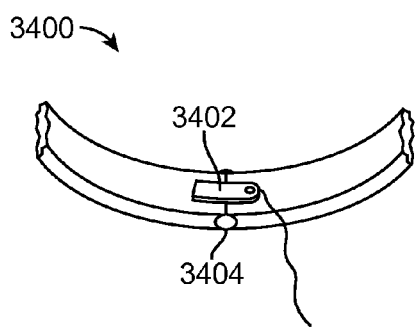
FIGS. 34A-B illustrate an embodiment of a locking mechanism for a device frame.
Figure 34B:
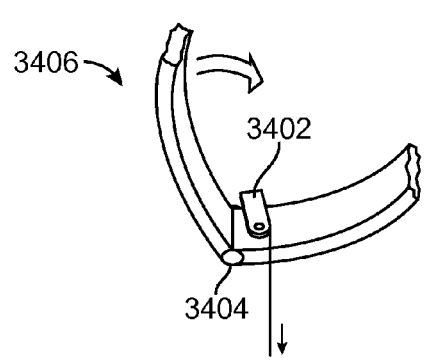
Figure 35A:
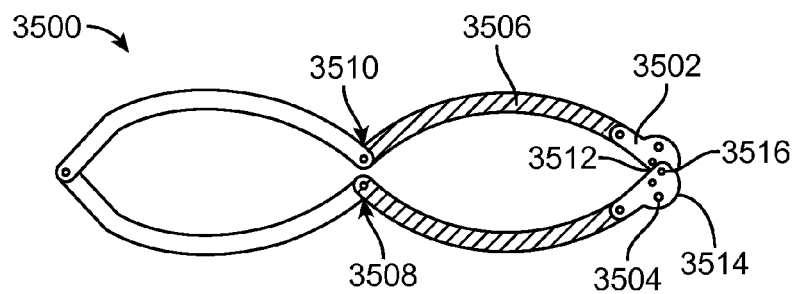
FIGS. 35A-D illustrate an embodiment of a collapsible device frame.
Figure 35B:
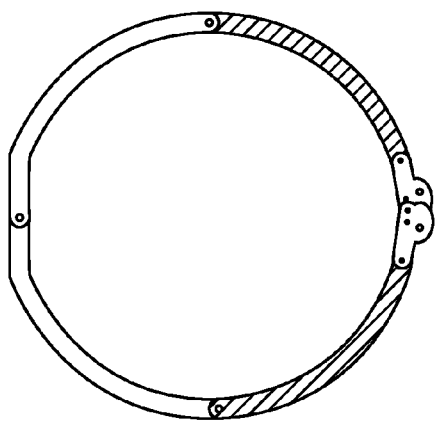
Figure 35C:
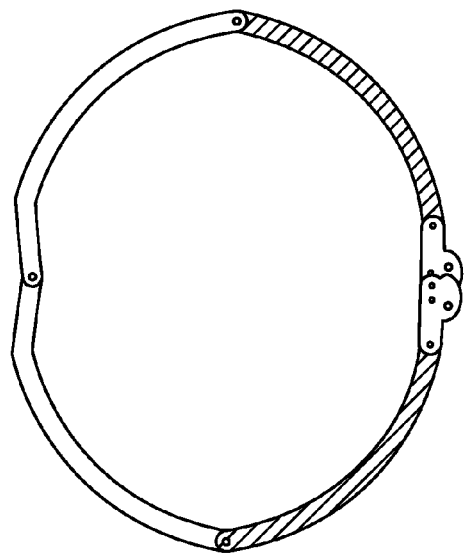
Figure 35D:
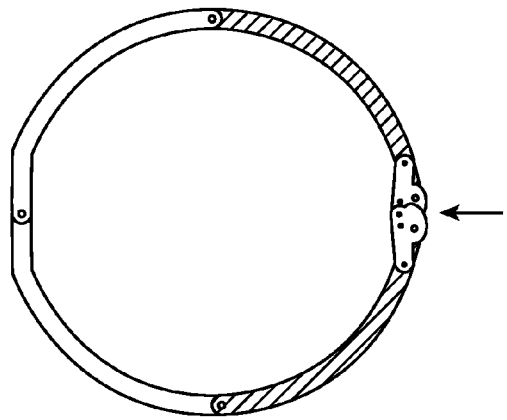

FIG. 34A illustrates an embodiment of a lock mechanism 3400. The locking mechanism comprises a locking member 3402 that can rotate or slide over the unfolded hinge 3404, preventing it from folding, as shown in FIG. 34A. The locking member 3402 can comprise a sheath, bar, rod, or the like. A string, tube, or the like can be used to move the locking member 3402 away from the hinge 3404, allowing it to fold. FIG. 34B illustrates the locking member 3402 rotated away from the hinge 3404. FIG. 34C illustrates an embodiment of a folded frame 3406 after rotation of the locking member 3402 away from the hinge 3404.

FIG. 35 illustrates a device frame 3500 with a locking mechanism on its distal portion which comprises two additional locking segments 3502, 3504 that can be placed into a position that prevents the hinge nearest the locking segments from further closing. The locking segments, when the device is collapsed, as shown in FIG. 35A, rotate towards one another (become more parallel) like the frame segments 3506 they are attached to. The rotation occurs at the lock segment central hinge 3512. The frame segments have their own central hinge that is hidden in the image by the lock segments. In this way, the entire frame, including the lock segments, can collapse without occupying a significant portion of the space between the frame segments, allowing space for cushioning and components of the extendable body and for the stabilizing body to have a passage through it for drainage of vaginal fluids. The lock segments are mounted on the frame segments at an arc distance, from the frame segments' central hinge, of at least ¹⁄₁₀ but not more than half the arc distance to the lateral frame hinges 3508, 3510. The more distal location places the lock segments closer to the vaginal opening and improves the user's ability to locate and press the segments. When the device is collapsed, the lock segments protrude only gently from the frame, facilitating device insertion. As the frame opens, the lock segments rotate open, becomes more collinear along their hinges. At the point or just before the frame is in its open state, the lock segments become more collinear, as shown in FIG. 35B. The user can then press on the lock segments with a finger to push them proximally. The raised features on the lock segments 3514 extend far enough past the frame so that the user can fully push the lock segments in before contacting the frame itself. In other embodiments, the frame segments do not have raised features, and the patient uses a tool to press the features inwards. As the lock segments are pushed by the patient, the frame will pass through a temporary wider (laterally) state, as shown in FIG. 35C, before the lock segments begin rotating the other direction (less collinear) and the device becomes narrower laterally, as shown in FIG. 35D. In this way, further compression of the device forces the lock segments to rotate inwards even further and prevents them from returning to their collapsed state. The lock segments have hard stop features 3516 which do not interfere with one another until reaching their locked position, at which point they contact a counter feature on the other segment. In some embodiments, one feature is the hard stop and counter. Once the hard stop is engaged, further lateral compression (e.g. applied at the lateral hinges 3508, 3510 of the device) is transferred in a bending moment along the length of the segments (e.g. segment 3506) that connect to lock segments (e.g. segment 3502) to the lock segments 3502, 3504 and their hard stop, preventing the device from collapsing. In order to allow the device to collapse, the patient can hook a finger inside the frame and pull the lock segments forward until they pass through their collinear configuration. At this point, lateral compression can again collapse the device. Alternately, a pull cord or component attached to the lock segment allows the user to pull the segments forward to allow collapse. The length of the lock segments as measured between their hinge to the frame segment and their own central hinge, can be ≥about ¾ and ≤to the distance between their hinge to the frame segment and central hinge of the frame segments. The lock segments being shorter reduces the lateral expansion required to pass through their collinear configuration, and therefore the force required to lock the device. In the locked configuration, the angle of the lock segments from parallel can be about 5-45 degrees; or about 10-30 degrees. This angle, when smaller, makes the open configuration, shown in FIG. 35D, more stable, but when larger, e.g., about 45-135 degrees, allows for smaller lock segments and places less moment on the hard stops, making them more robust and easing the force required for collapse. The hard stop features are located a distance that is about ≥equal to the diameter of the central hinge axle and ≤the distance between the hinges on a lock segment, more preferably about ⅛ to about ½ the distance between the hinges on a lock segment, where a longer distance increases stability, but where a shorter distance makes the lock segments more compact.

This embodiment shows very similar and symmetrical lock segments, but in other embodiments, the lock segments can be asymmetrical in their mounted location, length, or shape, and may not hinge at the center of the device.

Another embodiment can use lock segments that are extendable with a spring loading, assisting in their opening and closing and allowing them to be longer than the distance between their hinge mounting them to the frame segments and the frame segments' distal hinge.

The collapsing and locking mechanisms described herein can be applied in numerous combinations or permutations. It will be appreciated that the frame or other device components need not necessarily form circular or planar bodies. Other configurations that allow for ease in collapsing and opening are possible. The embodiments disclosed herein can be incorporated with electromagnetic components, other adhering elements (e.g., Velcro, temporary adhesives, magnets, etc.).

Unless otherwise specified, the frames described herein can be locked into an open configuration by applying force to anterior distal portion of the frame. Force can be applied using an external device (e.g., an applicator) or by user hands. The frames described herein can be unlocked by pulling on anterior distal portion of the frame. Pulling can be performed using an external device (e.g., a hook, an applicator), by a triggering mechanism (e.g., a string, tube, cord, wire, and the like), or by user hands.

While some of the embodiments described herein focus on applications for fecal incontinence, the devices and methods disclosed herein are not limited to devices for controlling fecal incontinence and can be applied to various types of vaginal devices. For example, the structures described herein can also apply to devices inserted into other body cavities such as the rectum.

Figure 36A:
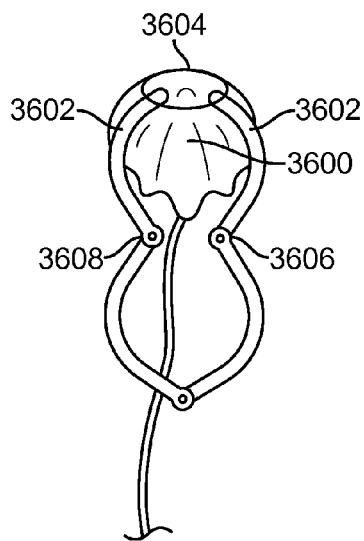
FIGS. 36A-B illustrate an embodiment of a collapsible intra-vaginal device.
Figure 36B:
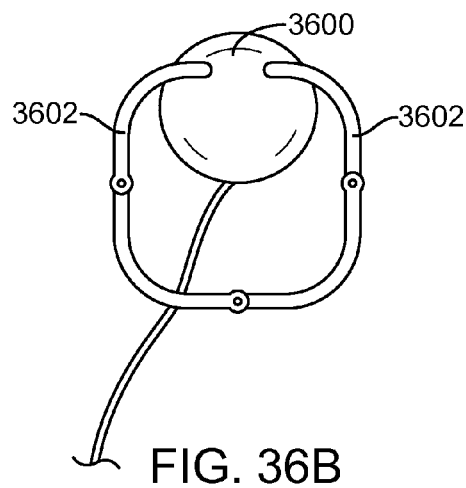

An additional advantage of the location and configuration of the expandable body is that it can be used to help open the frame. In an exemplary embodiment, shown in FIG. 36A, the expandable body 3600 resides at least partially within the perimeter of the collapsible frame and is attached to at least two segments 3602 of the frame. These segments can be arranged and configured to allow the expandable body to reside between them when the frame is collapsed. When inflated (shown in FIG. 36B), the expandable body 3600 expands and drives open the segments 3602. This can be done until a locking mechanism is engaged once the expansion crosses a pre-defined threshold (as described on other embodiments). In some examples, the expandable body is a bladder of a high durometer. The attachment between the segments and the balloon can occur as far from the joint 3604 that joins these segments as possible, maximizing potential leverage. Exemplary distances are about ¼ to ½ of the distance from the joint to the lateral hinges 3606 and 3608. The attachment between the expandable body and the frame segments 3602 can comprise a section of material that is more resilient than the bladder, providing features to transmit force to the frame segment that has a greater area for fluid pressure to act over. More generally, other embodiments are possible wherein the expandable body can expanded by means other than inflation, such as a linkage that is operably connected to the frame such that when the expandable body extends, the frame opens. Optionally, the bladder can hold the frame open without the use of a locking mechanism. In this case, deflation of the bladder can be used to allow the frame to collapse, or just become less resistant to lateral collapse.

Figure 37A:
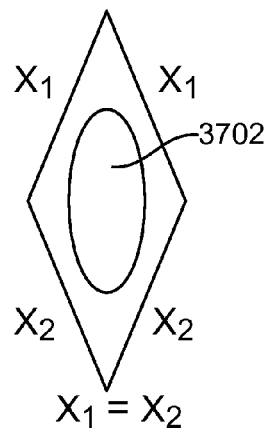
FIGS. 37A-D illustrate expansion of an embodiment of a collapsible device frame.
Figure 37B:
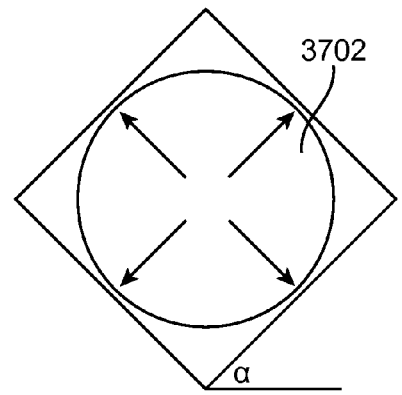
Figure 37C:
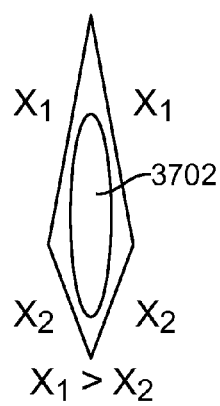
Figure 37D:
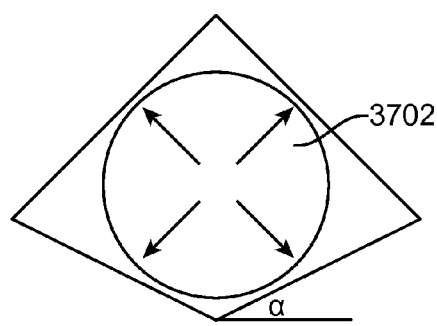

In some embodiments of devices using the expandable body to drive opening, the frame is configured to increase the advantage of inflation by shortening the frame segments near the expandable body. FIGS. 37A-D show expansion of a frame member comprising two sides X1 and two sides X2. As shown in FIGS. 37A and B, when X1=X2, expansion of the expandable body 3702 in the center of the frame causes the sides to expand equally, creating an angle α of about 45° between X2 and horizontal. As shown in FIGS. 37C and D, when X1 is greater than X2, expansion of the expandable body in the center of the frame causes the sides to expand unevenly, resulting in an angle α of less than 45°. A lower angle α indicates increased advantage in the driving open of the frame.

FIGS. 38A and B illustrate an embodiment of a frame 3800 configured to be driven open by expandable member 3802. FIG. 38A illustrates a top view of the frame 3800. The expandable member 3802 is positioned at one hinge point 3804 of the frame and is connected by a tensile element (e.g., via string 3806) to an opposing hinge point 3808. The string 3806 can be connected at a location 3810 on the expandable member that extends away from the frame 3800, as shown in the side view of FIG. 38B. As shown in FIGS. 38C and D, expansion of the expandable member 3802 moves the location 3810 away from the frame 3800, causing the string 3806 to pull on hinge point 3808, drawing hinge point 3808 towards hinge point 3804. The movement of hinge point 3808 towards hinge point 3804 causes the frame 3800 to open, as shown in the top view of FIG. 38E. FIG. 38F illustrates a side view of the frame 3800 and expandable member 3802.

In an embodiment shown if FIGS. 2A-2H, there are two rigid portions (e.g. segments 32 and 34), joined at a lockable joint (e.g. hinge 46) that allows and disallows the portions 32 and 34 to move with respect to each other. In particular, the lock-able joint 46 allows and disallows the portions 32 and 34 to move such that the angle between them changes. These portions can be joined to each other at the periphery of the structural perimeter. Together, these portions span the width of the open device, with one portion spanning predominantly one lateral side of the open device, and another portion spanning predominantly another lateral side of the open device. Preferably, these portions comprise a portion of the structural perimeter. More preferably, they comprise at least 25% of the structural perimeter. Preferably, these portions are joined at the distal or proximal end of the device (in-situ). Connected to the non-locked end of these two portions 32 and 34 (the ends that are nearest the widest point of an open device as shown in FIG. 2A) can be additional rigid portions 36 and 38. Alternatively, a spring-like portion, or a combination of one or more spring like portions and one more rigid portions can be connected to the non-locked ends of 32 and 34. These additional portions can themselves by joined, forming a loop, or additional portions can be added in between them. As described elsewhere, there can be a non-rigid segment of a similar or dissimilar material between the additional portions as well. A single "portion" as described above referring to the two rigid portions joined at the periphery of the structural perimeter can contain multiple distinct parts, so long as they provide rigidity at least in a manner that resists collapse when the locking mechanism is engaged.

Improved Insertion and/or Removal

In some embodiments, the intra-vaginal device is deformable to allow for manipulation of the device during insertion and removal. In such embodiments, it can be difficult for a user to hold a device in the deformed position during the entire insertion and/or removal. Intra-vaginal devices including retaining features to retain the stabilizing body in a collapsed or folded configuration can aid the insertion and removal process.

Figure 39A:
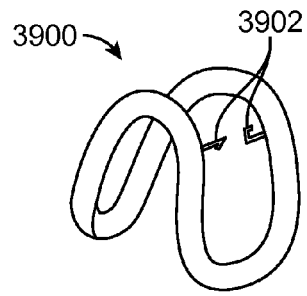
FIGS. 39A-C illustrate an embodiment of an intra-vaginal device comprising a latch.
Figure 39B:
Figure 39C:

FIG. 39A illustrates an embodiment of a device 3900 comprising a latch 3902 that catches when the device is folded together, for example, during insertion or removal. FIG. 39B illustrates the latch 3902 in more detail, with the latch components 3904 separated. Squeezing the device further can cause the latch to release, allowing it to open, as shown in FIG. 39C.

Figure 40A:
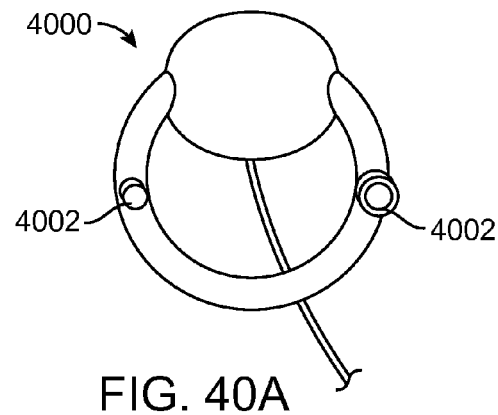
FIGS. 40A-B illustrate an embodiment of an intra-vaginal device comprising mating features.
Figure 40B:
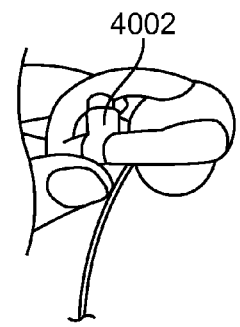

FIG. 40A illustrates an embodiment of a device 4000 with mating features 4002 on opposing sides of the device 4000. The mating features 4002 (e.g., press fit features snap fit feature, suction, magnets) are configured to engage one another by being pressed together. The engaged mating features 4002 can keep the device in a collapsed configuration during insertion and/or removal, as shown in FIG. 40B. When separation forces that can overcome the engagement of the features 4002 are applied, the device can open.

Figure 41A:
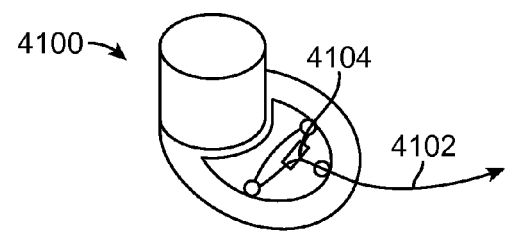
FIGS. 41A-C illustrate an embodiment of an intra-vaginal device comprising a tensile member.
Figure 41B:
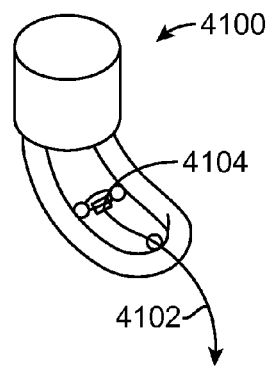
Figure 41C:
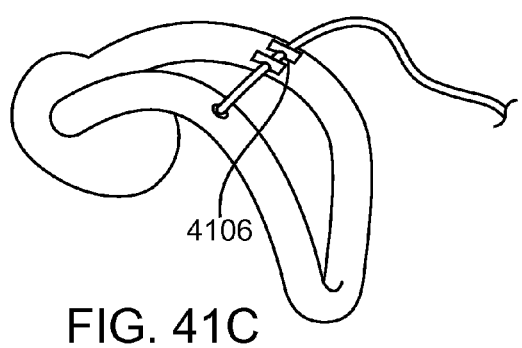

FIG. 41A illustrates an embodiment of a device 4100 comprising a tensile member 4102 extending between opposing sides of the device. The tensile member 4102 can cause the frame to fold or collapse by pulling the sides together upon application of tension to the tensile member 4102. A friction mechanism 4104, such as slip knot shown in FIG. 41B can be used to cause friction on the tensile member 4102 to maintain the device 4100 in a collapsed configuration. FIG. 41C illustrates an embodiment using a clamp 4106 as the friction member. The clamp 4106 can be released by pulling on the tensile member 4102. The tensile member 4102 can be configured to extend from the vagina for ease of use. In some embodiments, the tensile member 4102 is used to pull the device 4100 our or tilt the device 4100 to a position which is easier for a user to reach.

Figure 42:
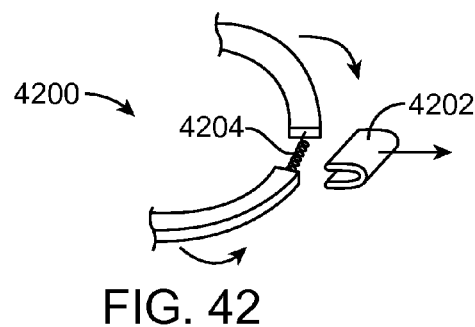
FIG. 42 illustrates an embodiment of a device frame comprising a keystone feature.

FIG. 42 illustrates an embodiment of a frame 4200 comprising a keystone feature 4202. The keystone feature 4202 covers a hinge or flexure 4204 in the frame 4200. The keystone feature 4202 can be removed to expose the hinge or flexure 4204. In some embodiments, a pull wire or cord can be used to remove the keystone feature 4202. After removal of the keystone feature 4202, the frame 4200 is able to collapse.

Figure 43A:
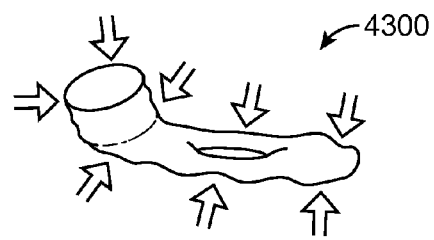
FIGS. 43A-C illustrate an embodiment of an intra-vaginal device comprising foam.
Figure 43B:
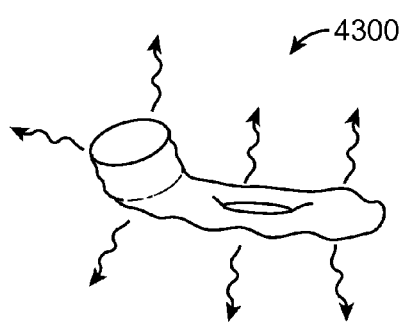
Figure 43C:
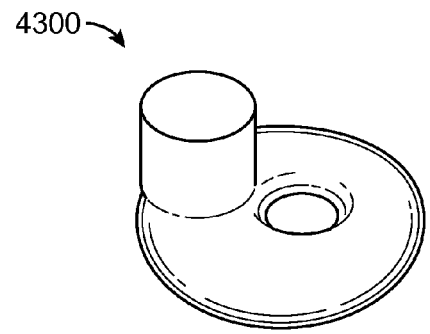

FIGS. 43A-C illustrates an embodiment of a device 4300 that is filled, at least in part, by a foam (e.g., slow recovery foam). The device 4300 can be compressed for insertion, as shown in FIG. 43A. Following insertion, the device 4300 can either expand passively or be inflated with air or fluid, as shown in FIG. 43B. FIG. 43C illustrates an inflated device 4300. Deflation of the device 4300 can aid in device removal.

In some embodiments, the device comprises, at least in part a flexible casing full of smaller pieces of hard material. The device can flex until vacuumed, which can cause it to become rigid. The addition of air or fluid can be used to soften the device for insertion and/or removal.

Figure 44A:
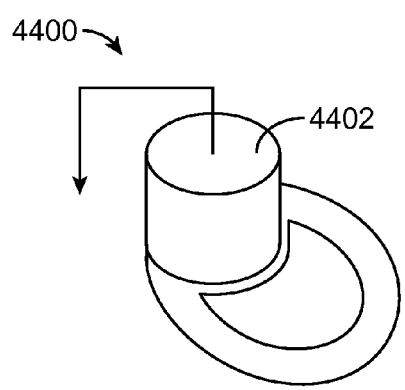
FIGS. 44A-B illustrate an embodiment of an intra-vaginal device comprising a movable expandable body.
Figure 44B:
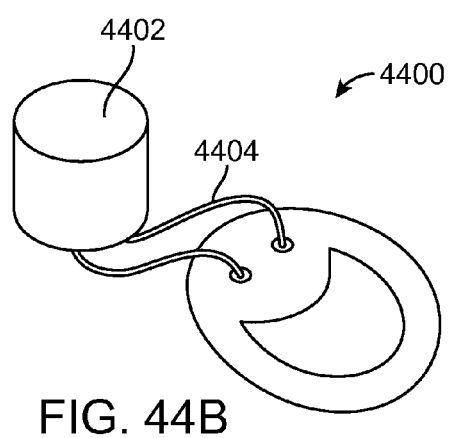

FIG. 44A illustrates an embodiment of a device 4400 in which the expandable body 4402 is movable or removable in order to narrow the device profile for insertion and/or removal. Removal of the expandable body can also allow the device 4400 to fold more easily. The expandable body 4402 can be temporarily removed. Reattachment can be performed using a pull cord 4404 as shown in FIG. 44B. Other reattachment mechanisms are also possible. For example, an elastic component (e.g., a spring) can also be used.

In some embodiments, deflation of the device actively opens a reservoir of a lubricating material to aid in device removal. In some embodiments, one or more channels through the device allow addition of a lubricating material through an external pathway.

Figure 64:
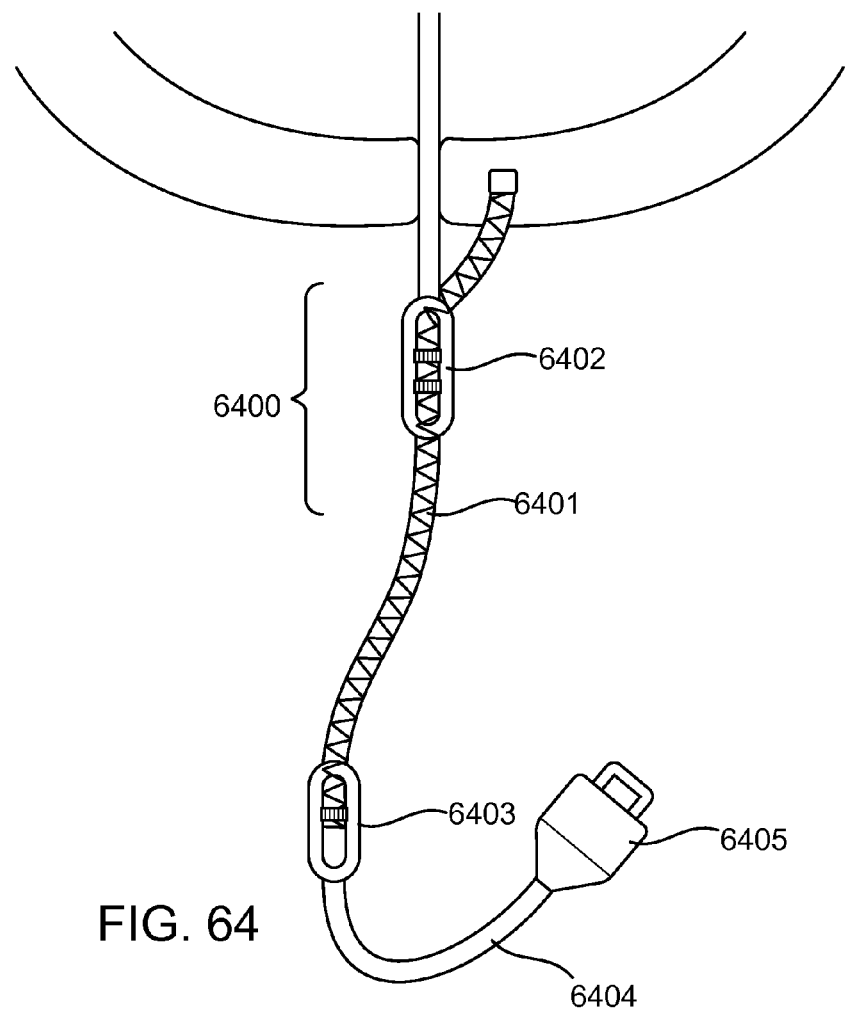
FIG. 64 illustrates an embodiment of inflation tubing.

In some embodiments, the device includes tensile elements in line with inflation tubing. Keeping tensile elements together with inflation tubing can allow a user to more easily pull the device out. The tensile element can be coupled to the inflation tubing. To do this, some portion of the tube is joined to the locking mechanism. This can be accomplished by a number of features, including a cord. In some embodiments, the tensile element is inside the inflation tubing. The tubing can have an integrated material (e.g., wire, suture) in its walls to allow the tubing to act as the tensile element. In some embodiments, the tensile element is separate from the inflation tubing (FIG. 64). As described above, in some embodiments, the tensile element 6401 can act as a triggering mechanism, activating collapse or folding of the device. In some embodiments, the tensile element simply allows the device to be pulled on. The tubing distal to the attachment to the locking mechanism, can be reinforced 6401 to prevent elongation when tensioned. The tubing can also have one or more features 6402, 6403 to facilitate the grip of a user. For example a bump along the tube or bead can facilitate grip. It is also advantageous to provide some portion of the tubing, distal to a reinforced section, which allows for elongation 6404. For example, in certain such embodiments, the device comprises an elastomeric portion (e.g., proximate to the inflation valve 6405). In this way, if a more distal portion of the tubing is pulled accidentally (e.g. caught in clothing or during manipulation to add/remove fluid) there is sufficient give in the tubing such that the device isn't unlocked. This configuration can allow for an amount of elongation before a sufficient amount of tensile force is generated to trigger the locking mechanism that is in the range of about 0.1 cm-20 cm; in the range of about 0.5-15 cm; in the range of about 0.5-10 cm. In some embodiments, the reinforced section of tubing extends just slightly past the introitus, at which point there is a feature for grasping; distal to this, the tubing can stretch when tensioned.

Figure 45:
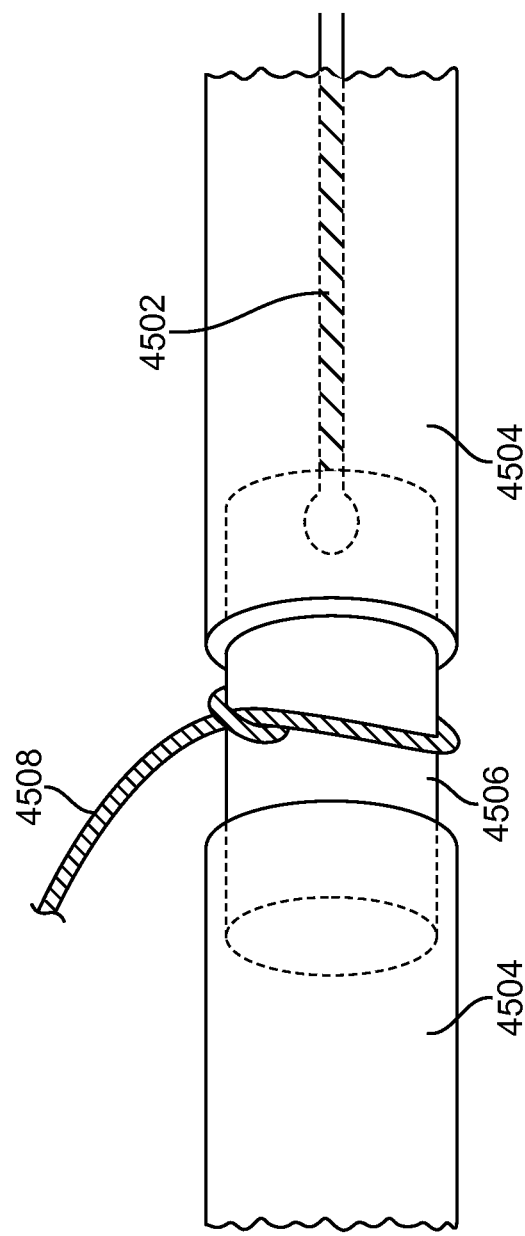
FIG. 45 illustrates an embodiment of reinforced tubing for use with an intra-vaginal device.

The tubing can be reinforced by several means, including braiding, linear components with suitable tensile properties (e.g. string, wire), polymeric coverings. As shown in FIG. 45, in some embodiments, a cord 4502, interior to the inflation tube 4504, is used to reinforce the tubing. It can be advantageous to configure this system such that the cord does not pierce the inflation tubing. This can be accomplished by connecting the reinforcement cord first to another component, such as a cylindrical fitting 4506, both ends of which are sealed to the inflation tube. Then, a separate cord 4508 can be attached to the exterior of this fitting and connected to the locking mechanism. This same configuration can be used on the distal end to couple the reinforcement cord to a grasping mechanism or other feature.

Figure 46A:
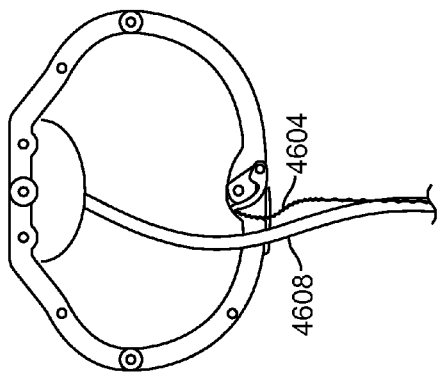
FIGS. 46A-F illustrate embodiments of removal features of intra-vaginal devices.
Figure 46B:
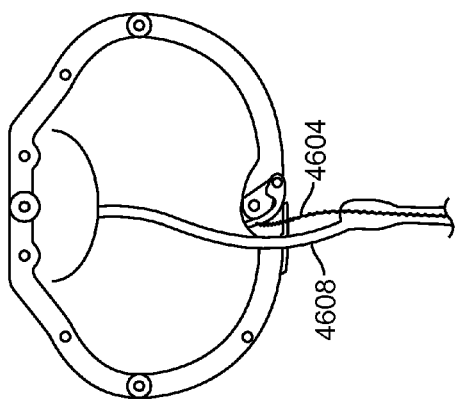
Figure 46C:
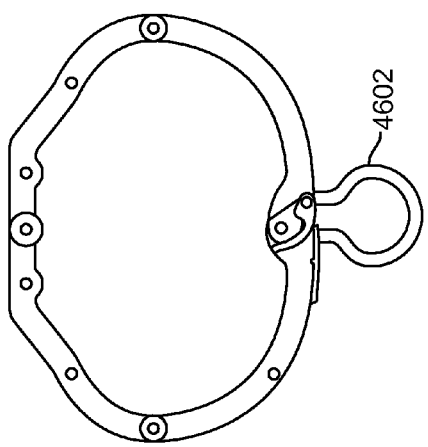
Figure 46D:
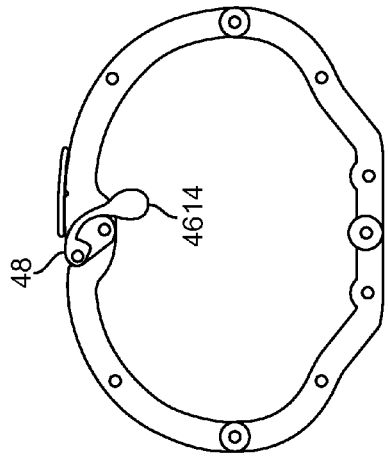
Figure 46E:
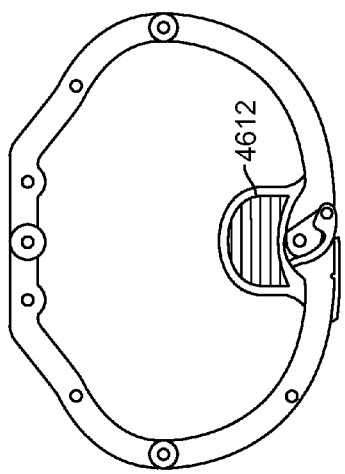
Figure 46F:
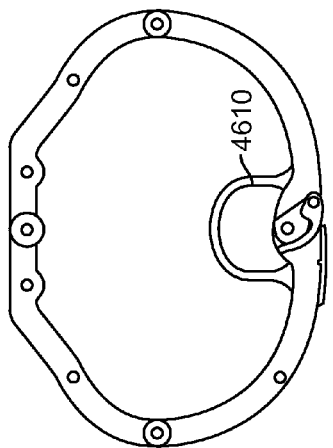

Referring to the examples of FIGS. 46A-46E: Instead of, or in combination with, a removal feature extending outside of the vagina, the feature that causes the locking mechanism to disengage can be located on the inside of the vagina; it can be further located inside the loop formed by the stabilizing body (e.g. requiring a user to hook a finger under the loop, as in the exemplary removal of a diaphragm) to trigger the release of the locking mechanism. The removal feature can be any number of features including, but not limited to: a tab, button, tube, string, or loop. These features can also be used to facilitate removal without them being directly coupled to a lock-release mechanism. Specific examples of features to assist with removal are provided in FIGS. 46A-E. FIG. 46A illustrates a pull loop 4602 for finger to hook. FIG. 46B illustrates a pull cord 4604 that passes through the inflation tubing 4608. FIG. 46C illustrates an embodiment of a pull cord 4604 runs parallel to the inflation tubing 4608. FIG. 46D illustrates a pull loop 4610 that is inside the frame. FIG. 46E illustrates a pull tab 4612 that is inside the frame. FIG. 46F illustrates a protrusion 4614 connected to latch 48 and positioned within the device frame. All of these features can be used to aid in removal and/or be coupled to a locking mechanism to enable or disable the lock. Any of the features described above can be stiff or soft and can be designed to spring-back into position after actuation.

There can be an advantage to having only one element passing from outside of the vagina to inside the vagina, for both sanitary and comfort reasons. There also can be an advantage to having a smooth (e.g. round) cross sectional profile of the element that passes from outside to inside, and to having that element be as small as possible as to be minimally obtrusive. The above concepts of reinforced tubing meet these objectives.

Dampening Device Opening

As described above, intra-vaginal devices, after being inserted in a deformed position, can cause discomfort by opening too quickly. It can be difficult for a user to control the opening of the device. Dampening the opening of the device can increase comfort and ease of use for the user.

In some embodiments, portions of the device can comprise soft or sticky materials which have less of a natural tendency to spring back to their original shape. Adjusting the durometer of at least portions of the device in this manner can allow for control of device opening. For example, as shown in FIG. 47, a top surface 4702 of the device can comprise a soft material, for example, silicone. Upon folding the device along axis 4704, the opposing silicone surfaces 4702 are in contact with one another. This contact causes the silicone surfaces to adhere to one another, providing temporary resistance to device opening upon release of the device. In some embodiments, the stabilizing body comprises a first portion comprising a first material and a second portion comprising a second material, the first and second materials selected to resist separation upon release of the stabilizing body. The first and second material can be the same, as in the example above where both comprise silicone. In other embodiments, the first and second material can be different. In some embodiments, the adherence of the surface is mechanical, one example being sheets of hook and loop fabric.

In some embodiments, at least two portions of the device (e.g., opposing surfaces) can comprises adherence features configured to temporarily cause the portions of the device to adhere to one another. For example, as shown in FIG. 48A, opposing surfaces of the device can include micro-suction features 4800. Upon folding of the device, the micro-suction features 4800 adhere to one another, as shown in FIG. 48B. The adherence of the micro-suction features 4800 provide temporary resistance to device opening, slowing down the opening of the device, as shown in FIG. 48C. Other adherence features are also possible. For example, a hook and loop feature can be used.

FIG. 49 illustrates a mechanism for dampening opening of a device frame. Two portions 4902, 4904 are rotated about the center of the device when it is folded. FIGS. 49A-C illustrate a cross section of the frame, showing portions 4902, 4904. The joint (e.g. elastomeric connection or hinge) between the portions 4902, 4904 is encapsulated by a highly viscous material 4908 (e.g., silicone gel), as shown in FIG. 49D. The viscous material can slow the return of the frame to the unfolded form. FIG. 49E illustrates the path of movement of location 4906 on portion 4904.

FIG. 50 illustrates an embodiment of a hydraulic dampening mechanism 5002. The device 5000 includes a dual chamber mechanism configure to transfer fluid between reservoirs during folding and unfolding of the device. FIG. 50A illustrates the device 5000 being folded. FIG. 50B depicts the hydraulic dampening mechanism 5002 in more detail. As the device is folded, the fluid flows from the chamber 5004 past a restriction 5006, slowing the fluid movement. After release of the device 5000 from a folded position, the spring force in the device can pull a vacuum in empty chamber 5004 on the device frame, drawing fluid into it. The release of the device 5000 can be controlled by the rate of fluid flowing into chamber 5004.

Dampening of a device opening can be useful in devices other than intra-vaginal devices. For example, dampening can be used in devices configured for insertion into other body cavities which are configured to expand upon insertion.

Insertion and/or Removal Tools

As described above, it can be difficult for a user to deform a device into a collapsed position for insertion and/or removal. Additionally, a user can prefer to insert a device while avoiding direct contact with her hands, as manual insertion can be difficult for users with conditions such as arthritis and can cause bodily fluids or lubrication to get on the hands. This is especially true for a device that, when collapsed, exerts outward forces which need to be continuously resisted in order to maintain a folded shape. Furthermore, devices with smooth exterior and curved surfaces can provide additional difficulty. Insertion and removal tools can be used to address these issues and help properly position the device in the vaginal anatomy can In some embodiments, the device can be packed into an applicator tube for insertion. During removal, the device can be pulled back into the same or a different tube. In some embodiments, the tube can be lubricated or constructed from low-friction materials to allow for movement of the device. In some embodiments, the tube comprises tapers and geometry appropriate for retrieving the intra-vaginal device. In some embodiments, the intra-vaginal device comprises a string or other tensile element that can be used to pull the device back into the applicator. In some embodiments, the applicator comprises a hook that can be used for retrieving the device. FIG. 51 illustrates an embodiment of an applicator 5100 comprising a hook feature 5102 and an intra-vaginal device 5104 comprising a cord 5106 or other tensile element extending across the device frame. The hook feature 5102 can be hooked onto the device 5104 and then pulled toward the applicator 5100. Pulling on the cord 5106 can cause the device to collapse. FIG. 51B illustrates an embodiment of the collapsed device 5104 being pulled into the applicator tube 5100.

FIGS. 52A and B illustrate an embodiment of an applicator 5200. The applicator 5200 comprises a rotating linkage 5202 connected to a translating component 5204. In the position shown in FIG. 52A, the linkage 5202 maintains hold of the device 5206. Upon moving the translating component 5204 to the right, as shown in FIG. 52B, the linkage rotates in a counter-clockwise position and releases hold of the device 5206.

FIGS. 53A and B illustrate an embodiment of an insertion and removal tool 5300 comprising arms 5302. The arms 5302 are biased in a position separate from one another, as shown in FIG. 53A. When the arms 5302 are in this separate position, they hold the device frame 5306 in an open configuration. Upon translation of a sheath 5304 over the arms 5302, however, the arms 5302 move closer to one another, collapsing the device frame 5306. Such a tool 5300 can be inserted into the vagina with the sheath 5304 holding the arms 5302 in a close position. Once the device frame 5306 is positioned, the sheath 5304 can be retracted to open the device frame 5306. In some embodiments, the tool 5300 comprises more than two arms. For example, a third arm can be used to pull back on the center of the device.

Figure 54C:
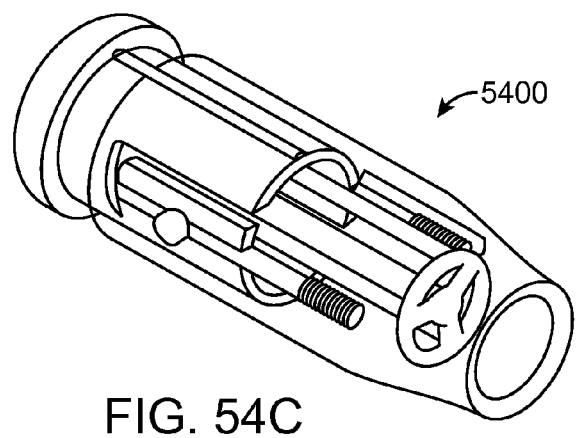
Figures 55A, 55B:
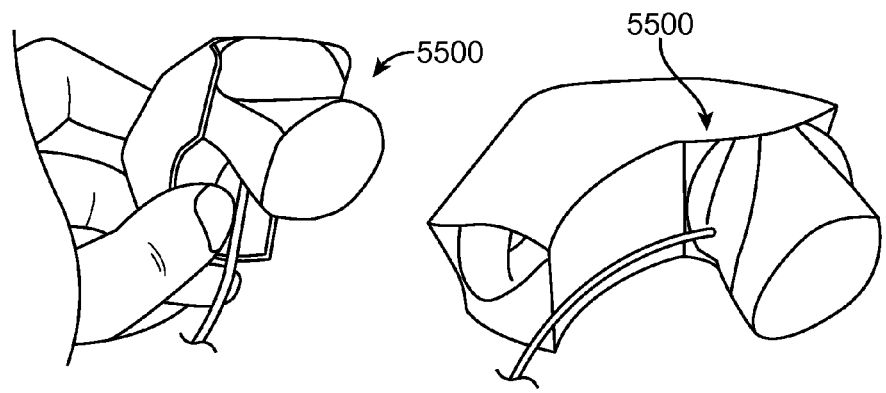
FIGS. 55A-B illustrate an embodiment of an applicator for an intra-vaginal device.

In some embodiments, plunger type applicators can be used. In a plunger-type applicator, the device is held in a compartment of an applicator and another portion of the applicator is actuated to push the device out. FIGS. 54A-B illustrate a plunger-type applicator 5400. The applicator comprises an applicator tube 5402 and a pusher 5404 for pushing the device 5406 out of the applicator tube 5402. The device 5406 shown in FIGS. 54A and B folds down into a curved shape. The applicator tube 5402 includes a slot 5408 to accommodate the end of the curved device 5406. FIG. 54B depicts the device 5406 being pushed out of the applicator 5400. FIG. 54C illustrates an applicator 5400 similar to the applicator of FIGS. 54A and B, but comprising a different shape. FIGS. 55A and B illustrate another plunger type applicator 5500 configured to accommodate a device that is curved when folded. The applicator 5500 comprises a curved shape.

Figures 56A, 56B, 56C:
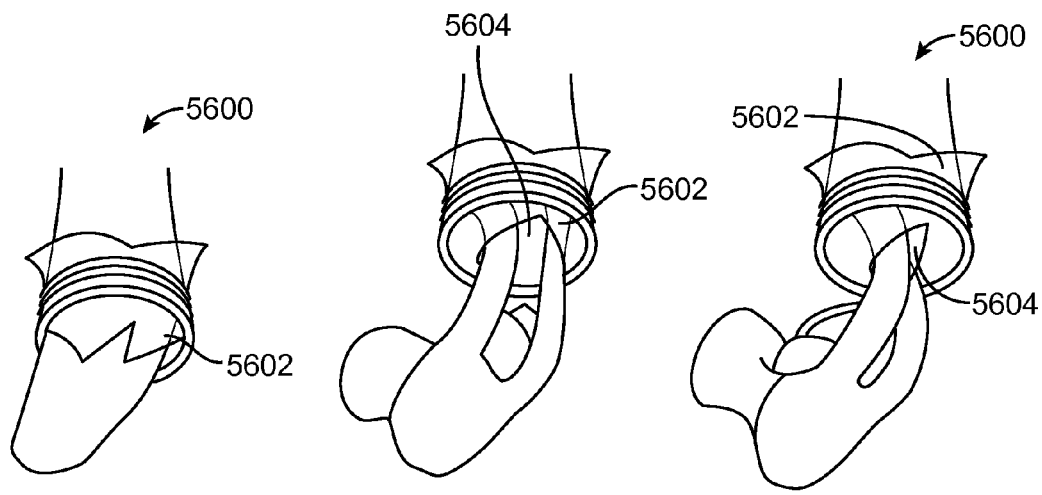
FIGS. 56A-C illustrate an embodiment of an applicator for an intra-vaginal device.

In some embodiments, the applicator opening can include projections configured to control the device ejection. The projections can include soft teeth or O-rings. FIGS. 56A-C illustrate a device being ejected from an applicator 5600 comprising a sheet of material 5602 (e.g., elastomer) comprising a slit 5604 over the opening of the applicator 5600. Such projections over the opening can resist the device ejection, slowing the release of the device.

Figure 57A:
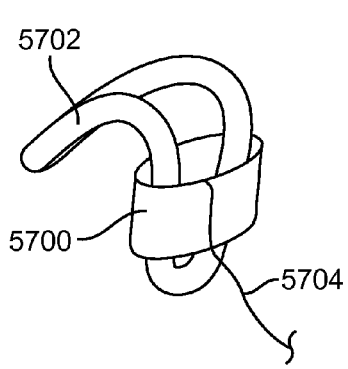
FIGS. 57A-C illustrate an embodiment of tearable sheath for use during intra-vaginal device insertion.
Figure 57B:
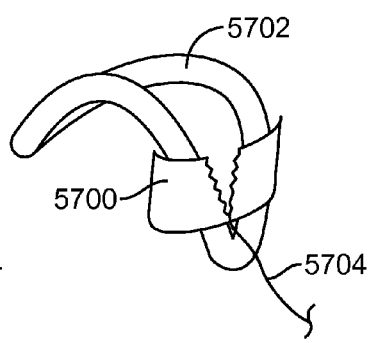
Figure 57C:
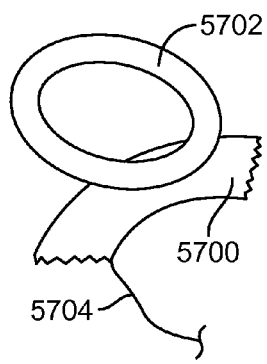

In some embodiments, external components can be used with or without tools to aid in insertion and/or removal of the intra-vaginal device. FIGS. 57A-C illustrate an embodiment of a sheath 5700 that can be used to hold the device 5702 together for insertion. The sheath 5700 can be configured to be tearable or releasable. A string 5704, shown in FIG. 57A, can be configured to tear the sheath 5700. FIG. 57B illustrates the string 5704 tearing the sheath 5700, causing the device 5702 to begin to open. FIG. 57C illustrates the sheath 5700 fully torn, causing the device 5702 to be fully open. In some embodiments, the sheath can be held together by rapidly dissolvable materials for insertion. Exposure to liquids such as lubrication, water, or vaginal fluids can cause the sheath to soften or break.

Figure 58A:
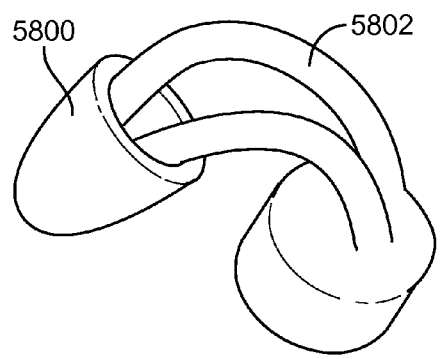
FIGS. 58A-B illustrate an embodiment of a cap that can be used for intra-vaginal device handling and insertion.
Figure 58B:
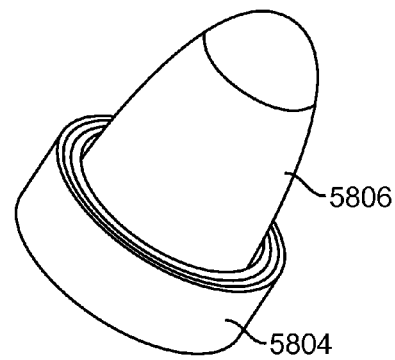

FIG. 58A illustrates an embodiment of a cap feature 5800 that can be used to hold a folded device 5802. The cap 5800 can be used to keep the device 5802 in a folded configuration and can also keep the hands of the user clean. The cap 5800 can be rigid and be removed by pulling. In some embodiments, the cap 5800 can have a rigid ring 5804 with a soft center 5806, as shown in FIG. 58B. The soft center 5806 can be used to eject the device. In some embodiments the cap can use a plunger or other internal mechanism to eject the device.

Figure 59A:
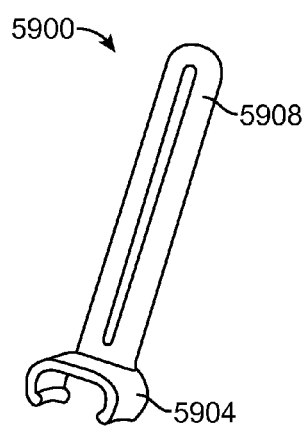
Figure 59B:
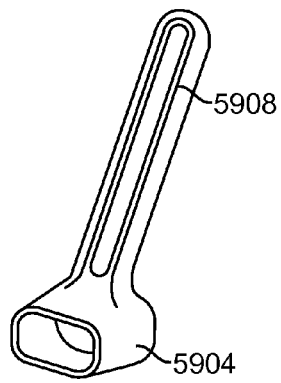
Figure 59C:
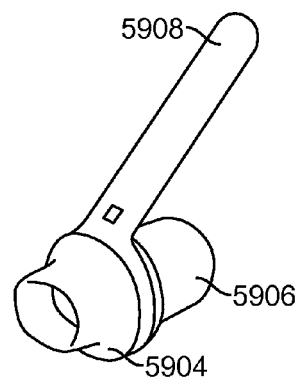

FIGS. 59A-C illustrate a tool 5900 that can be used to control the device for positioning at or within the vagina. The tool comprises a shaft 5908 and a retaining portion 5904. The tool 5900 can have an open retaining portion 5904 for holding the folded device, as shown in FIG. 59A. Alternatively, the tool 5900 can have a closed retaining portion 5904 for holding the device, as shown in FIG. 59B. FIG. 59C illustrates a tool 5900 with a closed retaining portion 5904 and a soft center 5906 allowing for device ejection. FIG. 59D illustrates a device 5902 positioned within the retaining portion 5904. FIG. 59E illustrates the device 5902 being ejected from the tool 5900 using a finger.

FIGS. 60A and B illustrate a snare tool 6000. The snare tool 6000 comprises a loop 6002 extending from a channel or opening on the tool 6000. The snare tool 6000 can be used to position the loop 6002 around the device 6004 to hold it in a folded configuration, as shown in FIG. 60A. FIG. 60B illustrates the loop 6002 being loosened, allowing the device 6004 to open.

FIG. 60C illustrates a snare tool with a ribbon-like loop 6006 with a cross-section having a major axis twice as large as the minor. The flatter material increasing grip without significantly increasing the tool profile, and can allow for better control of the device.

Figure 61A:
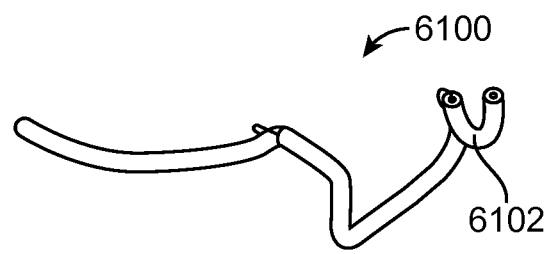
FIGS. 61A-B illustrate an embodiment of a mechanism for holding an intra-vaginal device.
Figure 61B:
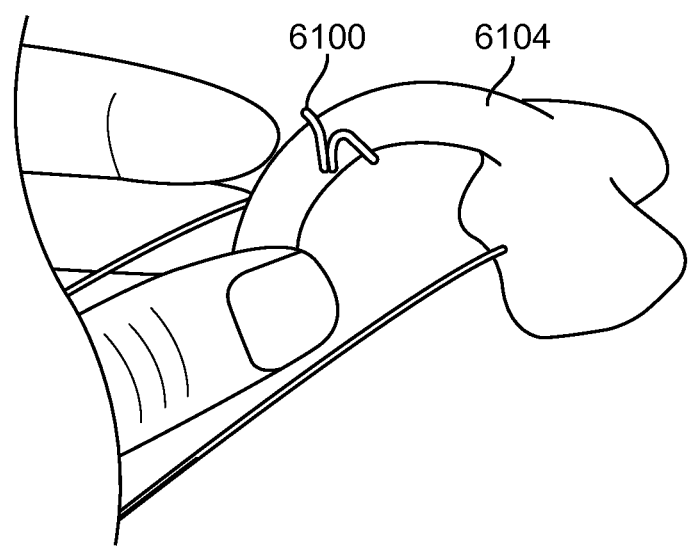

FIG. 61A illustrates a mechanism 6100 for holding a folded device using a resilient shape. The design 6100 includes a bent portion on which the stabilizing body is supported, and a clasp 6102 shaped so that it can retain the stabilizing body during insertion. Once inserted, the handle can be rotated relative to the device, allowing the clasp 6102 to release the stabilizing body. FIG. 61B illustrates an embodiment of a device 6104 being held in a folded configuration by the mechanism 6100.

Figure 62A:
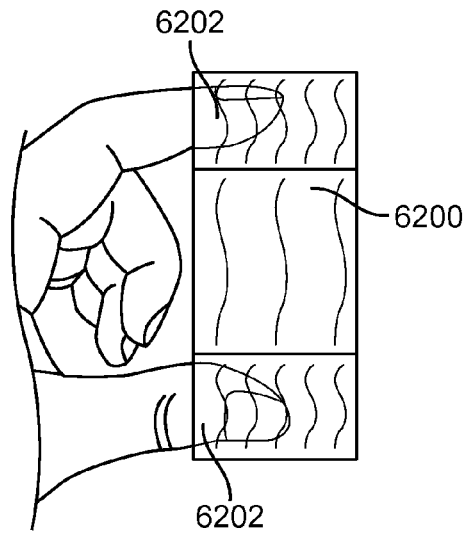
FIGS. 62A-C illustrate an embodiment of a sheet that can be used for holding an intra-vaginal device.
Figure 62B:
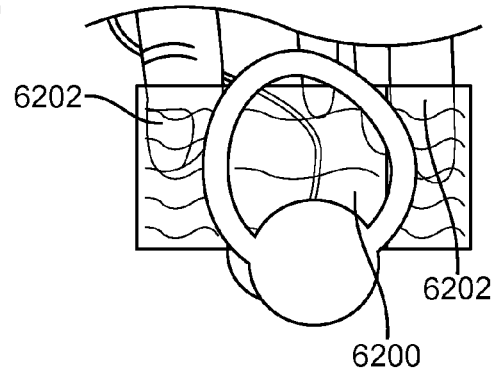
Figure 62C:
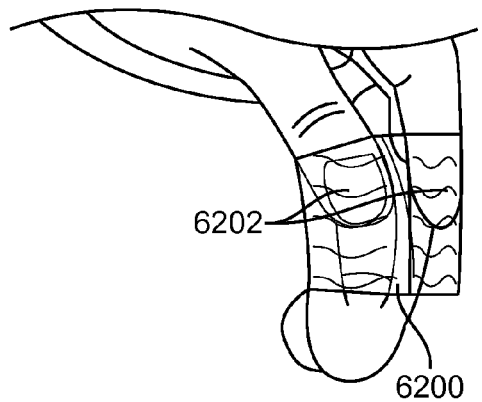

FIG. 62A illustrates a sheet of flexible material 6200 (e.g., polymeric or elastomeric) comprising openings 6202 for receiving user fingers. The sheet 6200 can be wrapped around the device 6204 as shown in FIGS. 62B and C. The sheet 6200 can help to improve grip and cleanliness during insertion and/or removal.

Figure 63A:
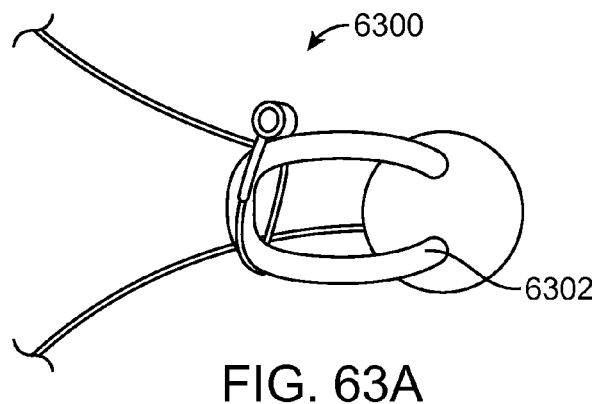
FIGS. 63A-B illustrate an embodiment of a sheet that can be used for holding an intra-vaginal device.
Figure 63B:
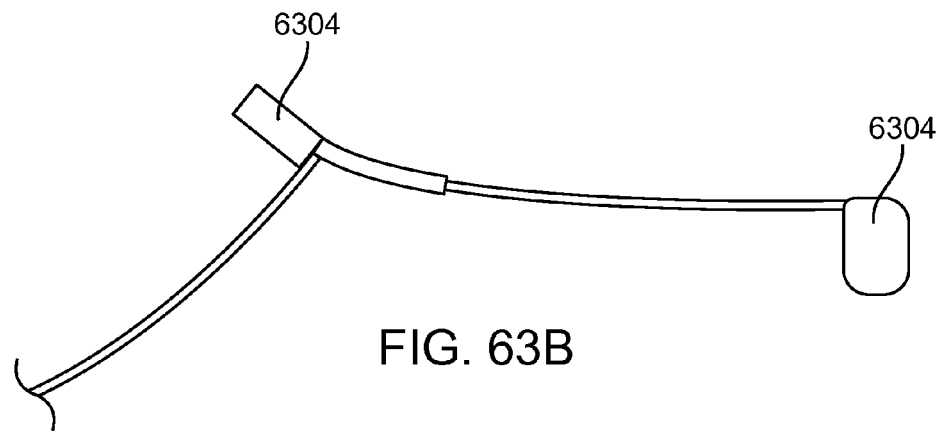

FIGS. 63A and B illustrate a mechanism 6300 than can be used to hold a device 6302 in a folded configuration. The mechanism comprises press-fit features 6304 on a cord 6306 or strap. When the cord 6306 or strap is pulled, the press-fit features 6304 release, as shown in FIG. 63B, allowing the device 6302 to open. In another embodiment, the cord can be adjusted in length between the press fit features to accommodate different device sizes.

The applicators and external components described herein can be used in combination with other embodiments described herein. For example, the applicators can be configured to facilitate locking of frames including locking mechanisms by including a pusher feature configured to push on the device base during insertion. Such a feature could be located at the tip of the tool or along the length of the tool.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" (or primary and secondary) may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An intravaginal device for the control of stool passage, the device comprising:
    a collapsible stabilizing body including a plurality of segments interconnected by joints and configured to modulate between an open state and a collapsed state by movement of the segments about the joints,
    an expandable body positioned above the stabilizing body, the expandable body configured to provide a non-extended state and an extended state, the expandable body configured to push against a recto-vaginal septum of a user in the extended state;
    a locking mechanism configured to maintain the collapsible stabilizing body in the open state upon engagement of the locking mechanism and permit the collapsible stabilizing body to collapse upon disengagement of the locking mechanism; and
    a support structure mounted to the stabilizing body to support a first portion of the expandable body, the support structure being configured to collapse or fold when the stabilizing body moves from the open state to the collapsed state, and the support structure being configured to support the first portion of the expandable body on at least one surface of the support structure when the stabilizing body is in the open state and the expandable body is in the extended state.

2. The device of claim 1, wherein the interconnected segments, in the open state of the stabilizing body, form a loop with a generally oval shape.

3. The device of claim 1, wherein the interconnected segments, in the collapsed state of the stabilizing body, form a loop with multiple generally oval shapes.

4. The device of claim 1, wherein in the collapsed state of the stabilizing body the segments have a lengthwise midpoint that is approximately half-way between a distal joint and proximal joint, wherein a width at this midpoint in the collapsed state of the stabilizing body is narrower than a width of a space spanned by the segments both proximal and distal to the midpoint.

5. The device of claim 4, wherein in the collapsed state of the stabilizing body, the approximate lengthwise midpoint forms a local minimum in the profile of the device.

6. The device of claim 1, wherein the expandable body is configured to protrude into the rectum by pushing against a recto-vaginal septum of a user in the extended state.

7. The device of claim 1, wherein:
in the open state of the stabilizing body, the device has a first width, a first length, and a first height; and
in the collapsed state of the stabilizing body, the device has a second width, a second length, and a second height, the second width being 50% less than the first width, the second length being greater than the first length, and the second height being substantially the same as the first height.

8. The device of claim 1, wherein the stabilizing body is comprised of multiple interconnected segments that are joined together to form a loop.

9. The device of claim 1, wherein the stabilizing body comprises multiple interconnected segments that are joined by joints, wherein at least one of the joints comprises an elastomeric material.

10. The device of claim 1, wherein at least a portion of at least some of the plurality of segments have an arcuate shape.

11. The device of claim 1, wherein the plurality of segments is arranged symmetrically about an axis that extends between the locking mechanism and the expandable body.

12. The device of claim 1, wherein the expandable body is positioned above a joint between interconnected segments.

13. The device of claim 1, wherein the expandable body is positioned above a joint located opposite to the locking mechanism.

14. The device of claim 13, wherein the expandable body is an inflatable balloon, extending from the joint in a generally perpendicular direction from a plane of the interconnected segments, wherein the joint is located between the balloon and a soft cushion material.

15. The device of claim 1, wherein, in the open state of the stabilizing body, a portion of the collapsible stabilizing body has an arcuate shape and a portion of the collapsible stabilizing body has a linear shape.

16. The device of claim 15, wherein, in the open state of the stabilizing body, the expandable body is positioned above the linearly shaped portion of the collapsible stabilizing body.

17. The device of claim 1, wherein the expandable body is attached to a periphery of the intravaginal device.

18. The device of claim 1, wherein the collapsible stabilizing body is configured to provide an interconnected frame forming a structural perimeter of the device.

19. The device of claim 18, wherein the interconnected frame is comprised of metal segments, joined together and surrounded by a soft cushioning material.

20. The device of claim 18, wherein the collapsible stabilizing body comprises at least 3 interconnected joints that are configured to be constrained to one degree of freedom of angular motion.

21. The device of claim 1, wherein the collapsible stabilizing body is configured to resist out-of-plane bending.

22. The device of claim 1, wherein joints of the interconnected segments are configured to constrain the interconnected segments to rotational motion in a plane of the frame.

23. The device of claim 1, wherein the expandable body is coupled to the collapsible stabilizing body by a flexible coupling.

24. The device of claim 1, wherein the expandable body comprises a support member that is connected to the collapsible stabilizing body, wherein the support member spans less than 50% of a distance across a longitudinal span of the stabilizing body in the open state of the stabilizing body.

25. The device of claim 1, wherein:
in the open state of the stabilizing body, the collapsible stabilizing body has a first width and a first length; and
in the collapsed state of the stabilizing body, the collapsible stabilizing body has a second width and a second length, the second width being less than the first width and the second length being greater than the first length.

26. The device of claim 1, wherein the plurality of segments comprises at least six segments.

27. The device of claim 1, wherein the plurality of segments comprises at least four segments.

28. The device of claim 1, wherein the device has an outer profile, and wherein the interconnected segments deviate from the outer profile at a proximal portion of the stabilizing body.

29. The device of claim 1, further comprising an encapsulating material disposed around the collapsible stabilizing body, the encapsulating material having a first thickness between the interconnected segments and an exterior surface of the stabilizing body in regions disposed away from the expandable body and a second thickness between the interconnected segments and an exterior surface of the stabilizing body in regions disposed proximate to the expandable body, the second thickness being greater than the first thickness.

30. The device of claim 1, further comprising a tensile element attached to the locking mechanism, the tensile element configured to permit disengagement of the locking mechanism via application of force to the tensile element.

31. The device of claim 30, wherein the tensile element is operatively connected to an inflation lumen that communicates with the expandable body.

32. The device of claim 30, wherein the tensile element comprises a string, tube, cable, wire, or cord.

33. The device of claim 1, wherein the plurality of segments includes:
a first arcuate segment;
a second arcuate segment moveably connected to the first arcuate segment;
a third segment having an arcuate portion and a linear portion, the third segment being moveably connected to the first segment; and
a fourth segment having an arcuate portion and a linear portion, the fourth segment being moveably connected to both the third segment and the second segment.

34. The device of claim 1, wherein the plurality of segments includes:
   a first arcuate segment;
   a second arcuate segment moveably connected to the first arcuate segment and disposed opposite to the first arcuate segment along an axis;
   a third arcuate segment moveably connected to the first arcuate segment;
   a fourth arcuate segment moveably connected to the second arcuate segment and disposed opposite to the third arcuate segment along the axis;
   a fifth linear segment moveably connected to the third arcuate segment; and
   a sixth linear segment moveably connected to the fourth arcuate segment and disposed opposite to the fifth linear segment along the axis.

35. The device of claim 1, wherein the plurality of segments comprises lateral arms with midpoints, wherein the midpoints can be moved from the open state to a collapsed state wherein in the collapsed state the distance between opposing midpoints is reduced by ≥50%.

36. The device of claim 1, wherein the stabilizing body and the support structure are configured to collapse in a common plane.

37. The device of claim 1, wherein the support structure defines a slot in which a post extending from the stabilizing body is positioned to cause the support structure to collapse as the stabilizing body collapses.

38. The device of claim 1, wherein the support structure covers an entire area of one side of the expandable body.

39. A method of controlling stool passage in a user, the method comprising
   inserting an intra-vaginal device in the user's vagina, the device comprising a collapsible stabilizing body including a plurality of segments interconnected by joints, a support structure mounted to the stabilizing body, and an expandable body, the collapsible stabilizing body being in a collapsed state during insertion, and the support structure being in a collapsed or folded state during insertion;
   moving the interconnected segments about the joints to modulate the collapsible stabilizing body from the collapsed state to an open state and to move the support structure from the collapsed or folded state to an expanded state;
   locking the collapsible stabilizing body in the open state;
   extending the expandable body against a recto-vaginal septum of the vagina to at least partially occlude the user's rectum, the support structure being in the expanded state and supporting a first portion of the extended expandable body on at least one surface of the support structure; and
   retracting the expandable body while the stabilizing body is open to permit stool to pass through the rectum.

40. The method of claim 39, further comprising applying force to a tensile element attached to the locking mechanism, unlocking the collapsible stabilizing body from the open state.

41. The method of claim 40, wherein tensile element is part of an inflation tube.

42. The method of claim 39, wherein the interconnected segments and the support structure move in a common plane when the interconnected segments and the support structure move to their open and expanded states, respectively.

43. The method of claim 39, wherein the support structure defines a slot in which a post extending from the stabilizing body is positioned to cause the support structure to move into the expanded state as the stabilizing body moves to the open state.

44. The method of claim 39, wherein the support structure covers an entire area of one side of the expandable body.

45. An intravaginal device for the control of stool passage of an adult human female user, the device comprising,
   an expandable body;
   an intravaginal stabilizing body supporting the expandable body to maintain position and stability of the expandable body in the user's vagina during repeated expansions of the expandable body in an extension direction to contact the user's rectovaginal septum to at least partially occlude the rectum, the stabilizing body comprising a locking mechanism, the stabilizing body having a collapsed configuration and a stable open configuration in which the stabilizing body is held open by the locking mechanism; and
   a support structure mounted to the stabilizing body to support a first portion of the expandable body, the support structure being configured to collapse or fold when the stabilizing body moves from the open configuration to the collapsed configuration, and the support structure being configured to support the first portion of the expandable body on at least one surface of the support structure when the stabilizing body is in the open configuration and the expandable body is expanded.

46. The device of claim 45, wherein the stabilizing body comprises a plurality of arms connected to form a loop.

47. The device of claim 46, wherein the stabilizing body comprises 4 arms.

48. The device of claim 40, wherein the stabilizing body has a generally ovular shape.

49. The device of claim 46, wherein the stabilizing body is configured to collapse along its length as it moves from the open configuration to the collapsed configuration.

50. The device of claim 45, wherein, in the open configuration, the expandable body is disposed at a location of the stabilizing body having a width less than the maximum width of the stabilizing body.

51. The device of claim 45, wherein a thickness of the stabilizing body in the extension direction is less than the length of the expandable body in the extension direction.

52. The device of claim 45, wherein, in the collapsed configuration of the stabilizing body, the expandable body is supported so that it is disposed in a space between portions of the stabilizing body.

53. The device of claim 45, wherein the stabilizing body comprises two arms connected by a hinge, the locking mechanism configured to prevent or permit movement of the hinge.

54. The device of claim 53, wherein the locking mechanism comprises a latch that is configured to move into and out of a pocket positioned proximate to the hinge between two arms, wherein the latch being positioned in the pocket prevents the two arms from moving relative to one another.

55. The device of claim 54, wherein the hinge and the latch are configured to rotate about a same point.

56. The device of claim 54, wherein the latch is connected to the stabilizing body by a pin joint and is configured to rotate into the pocket.

57. The device of claim 45, wherein the locking mechanism comprises a rotatable joint positioned between two arms configured to allow the opening or closing of the stabilizing body upon rotation of the joint.

58. The device of claim 45, wherein the locking mechanism comprises at least one resilient member extending across the stabilizing body, holding the stabilizing body open when the resilient member is in a resting state.

59. The device of claim 58, wherein, in the resting state, the resilient member is configured to hold the stabilizing body open to a degree greater than a degree to which the stabilizing body is open when the device is inserted in the patient's vaginal cavity.

60. The device of claim 45, wherein the locking mechanism comprises a detent on an end of a first arm configured to catch on a feature of an end of a second arm.

61. The device of claim 60, wherein the detent comprises at least one of a spring loaded ball or a leaf spring.

62. The device of claim 60, wherein the feature comprises at least one of an edge of the second arm or a feature shaped to mate with the detent.

63. The device of claim 45, wherein the device comprises a stable collapsed configuration and a stable open configuration.

64. The device of claim 63, wherein the stabilizing body comprises a plurality of arms, and at least two of the plurality of arms have a first configuration in which the at least two arms extend inwardly towards a center of the stabilizing body and a second configuration in which the at least two arms extend outwardly away from the center of the stabilizing body.

65. The device of claim 45, wherein the locking mechanism comprises a bistable component extending between a first arm and a second arm of the stabilizing body.

66. The device of claim 65, wherein the bistable component comprises a hinge connecting the first arm and the second arm.

67. The device of claim 66, wherein a resilient member extends between a first end of the first arm and a second end of the second arm, the resilient member configured to be in a first tensioned state when the stabilizing body is in the open configuration or the collapsed configuration and a second tensioned state when moving between the open and collapsed configurations, wherein the second tensioned state is higher than the first tensioned state.

68. The device of claim 45, wherein the device is configured to collapse into two sections in the collapsed configuration.

69. The device of claim 45, wherein the device is configured to collapse into more than two sections in the collapsed configuration.

70. The device of claim 45, wherein the locking mechanism comprises an opening on a first end of a first arm configured to catch an extension on a second end of a second arm.

71. The device of claim 45, wherein the stabilizing body is configured to collapse by folding together.

72. The device of claim 45, wherein the stabilizing body comprises two hinges configured to allow the stabilizing body to fold.

73. The device of claim 72, wherein the stabilizing body comprises two additional hinges configured to allow the folded stabilizing body to straighten.

74. The device of claim 73, wherein the two additional hinges are joints, rotatable to allow folding of the stabilizing body.

75. The device of claim 45, wherein the stabilizing body comprises a shape memory alloy comprising a transition temperature other than body temperature.

76. The device of claim 75, wherein the shape memory alloy is configured to change shape upon application of temperature or current.

77. The device of claim 45, wherein the locking mechanism comprises at least two internal structures with flexible portions, movable relative to one another, configured to facilitate device collapse upon alignment of the flexible portions.

78. The device of claim 45, wherein the stabilizing body comprises multiple frame segments with a tensile member passed through the frame segments.

79. The device of claim 45, wherein the locking mechanism comprises a hinge with a sheath movable to cover or expose the hinge.

80. The device of claim 79, wherein the sheath is configured to prevent motion of the hinge when the sheath covers the hinge.

81. The device of claim 45, further comprising a triggering mechanism configured to transition the stabilizing body to the collapsible state.

82. The device of claim 81, wherein the triggering mechanism is located proximate to an inflation lumen connected to the expandable body.

83. The device of claim 82, wherein the triggering mechanism is coupled to the inflation lumen.

84. The device of claim 81, wherein the device comprises an elastomeric portion distal to the triggering mechanism.

85. The device of claim 45, wherein the stabilizing body and the support structure are configured to collapse in a common plane.

86. The device of claim 45, wherein the support structure defines a slot in which a post extending from the stabilizing body is positioned to cause the support structure to collapse as the stabilizing body collapses.

87. The device of claim 45, wherein the support structure covers an entire area of one side of the expandable body.

88. A method of selectively occluding a rectum to inhibit stool passage in a female user, the method comprising
   inserting an intravaginal device into the user's vagina, the device comprising a stabilizing body, a support structure mounted to the stabilizing body, and an expandable body, the stabilizing body being in a collapsed configuration during insertion, and the support structure being in a collapsed or folded state during insertion;
   moving the stabilizing body from the collapsed configuration to an open configuration such that the support structure moves from the collapsed or folded state to an expanded state;
   engaging vaginal anatomy with the stabilizing body in the open configuration to stably support the expandable body;
   locking the stabilizing body in the open configuration;
   extending the expandable body against a recto-vaginal septum of the vagina body during the engaging step to at least partially occlude the user's rectum, the support structure being in the expanded state and supporting a first portion of the extended expandable body on at least one surface of the support structure; and
   retracting the expandable body while the stabilizing body is in the open configuration to permit stool to pass through the rectum.

89. The method of claim 88, further comprising pulling on a distal portion of the intravaginal device, thereby causing the stabilizing body to collapse from the open configuration to the collapsed configuration.

90. The method of claim 89, further comprising removing the device from the user's vagina.

91. The method of claim 89, wherein pulling on a distal portion of the intravaginal device comprises pulling on a tensile element attached to a distal portion of the device.

92. The method of claim 91, wherein the tensile element comprises a string, cord, or reinforced tube.

93. The method of claim 88, wherein the extending step comprises inflating the expandable body to a pressure of 40-150 mm Hg.

94. The method of claim 88, wherein the engaging step comprises engaging internal vaginal anatomy to stably support the expandable body proximal to the vagina's perineal body while maintaining slack in the vagina wall.

95. The method of claim 88, wherein the engaging step comprises distending lateral walls of the vagina proximate to the expandable body less than in areas not proximate to the expandable body.

96. The method of claim 88, wherein the stabilizing body and the support structure move in a common plane when the stabilizing body and the support structure move to their open configuration and expanded state, respectively.

97. The method of claim 88, wherein the support structure defines a slot in which a post extending from the stabilizing body is positioned to cause the support structure to move into the expanded state as the stabilizing body moves to the open configuration.

98. The method of claim 88, wherein the support structure covers an entire area of one side of the expandable body.

\* \* \* \* \*

UNITED STATES PATENT AND TRADEMARK OFFICE
CERTIFICATE OF CORRECTION

| | | |
|---|---|---|
| PATENT NO. | : 9,974,635 B2 | Page 1 of 1 |
| APPLICATION NO. | : 14/181576 | |
| DATED | : May 22, 2018 | |
| INVENTOR(S) | : Miles Harris Rosen et al. | |

It is certified that error appears in the above-identified patent and that said Letters Patent is hereby corrected as shown below:

In the Claims

Column 50, Line 34, Claim 48, delete "claim 40," and insert --claim 46,--.

Signed and Sealed this
Tenth Day of July, 2018

Andrei Iancu
*Director of the United States Patent and Trademark Office*